United States Patent
Lux et al.

(10) Patent No.: US 9,624,274 B2
(45) Date of Patent: Apr. 18, 2017

(54) MUTATED STRUCTURAL PROTEIN OF A PARVOVIRUS

(71) Applicant: MediGene AG, Planegg/Martinsried (DE)

(72) Inventors: Kerstin Lux, Munich (DE); Hildegard Buening, Cologne (DE); John Nieland, Aarhus-C (DK); Jorge Boucas, Cologne (DE); Mirko Ritter, Planegg (DE); Markus Hoerer, Planegg (DE); Luca Perabo, Cologne (DE); Michael Hallek, Cologne (DE)

(73) Assignees: Medigene AG, Planegg/Martinsried (DE); Ludwig-Maximilians-Universitaet, Munich (DE); Universitaet zu Koeln, Cologne (DE)

( * ) Notice: Subject to any disclaimer, the term of this patent is extended or adjusted under 35 U.S.C. 154(b) by 0 days.

(21) Appl. No.: 13/649,771

(22) Filed: Oct. 11, 2012

(65) Prior Publication Data
US 2013/0108658 A1 May 2, 2013

Related U.S. Application Data

(63) Continuation of application No. 12/601,651, filed as application No. PCT/EP2008/004365 on Jun. 2, 2008, now abandoned.

(60) Provisional application No. 60/932,410, filed on May 31, 2007.

(51) Int. Cl.
| | |
|---|---|
| *C07K 14/015* | (2006.01) |
| *C12N 7/00* | (2006.01) |
| *C07K 14/005* | (2006.01) |
| *C12N 15/86* | (2006.01) |
| *A61K 39/00* | (2006.01) |

(52) U.S. Cl.
CPC .......... *C07K 14/015* (2013.01); *C07K 14/005* (2013.01); *C12N 7/00* (2013.01); *C12N 15/86* (2013.01); *A61K 2039/5256* (2013.01); *A61K 2039/5258* (2013.01); *C07K 2319/40* (2013.01); *C12N 2750/14121* (2013.01); *C12N 2750/14122* (2013.01); *C12N 2750/14143* (2013.01); *C12N 2750/14145* (2013.01); *C12N 2810/405* (2013.01)

(58) Field of Classification Search
None
See application file for complete search history.

(56) References Cited

U.S. PATENT DOCUMENTS

| | | | |
|---|---|---|---|
| 6,719,978 B2 * | 4/2004 | Schiller et al. ............ | 424/199.1 |
| 2004/0053410 A1 | 3/2004 | Horer et al. | |
| 2004/0228798 A1 | 11/2004 | Schiller et al. | |

FOREIGN PATENT DOCUMENTS

| | | | |
|---|---|---|---|
| WO | WO-96/02555 A1 | 2/1996 | |
| WO | WO-01/05990 A1 | 1/2001 | |
| WO | WO-01/05991 A1 | 1/2001 | |
| WO | WO-01/54720 A1 | 8/2001 | |
| WO | WO-01/93903 A1 | 12/2001 | |
| WO | WO-01/93905 A1 | 12/2001 | |
| WO | WO-02/13857 A2 | 2/2002 | |
| WO | WO-02/32451 A1 | 4/2002 | |
| WO | WO-02/095027 A2 | 11/2002 | |
| WO | 03/054197 * | 7/2003 | ............ C12N 15/33 |
| WO | WO-03/054197 A2 | 7/2003 | |

OTHER PUBLICATIONS

Grifman et al (Molecular Therapy 3:964-975, 2001; in IDS).*
Rueda et al (Virology 263:89-99, 1999).*
Chapman et al (Virology 194:491-508, 1993).*
Wu et al., Journal of Virology, 2006, 80(22):11393-11397.*
Arnold et al., "Metabolic Biotinylation Provides a Unique Platform for the Purification and Targeting of Multiple AAV Vector Serotypes," Mol Ther. 14(1):97-106 (2006).
Asokan et al., "AAV Does the Shuffle," Nat Biotechnol. 24(2):158-60 (2006).
Asquith et al., "Emerging Cytokine Targets in Rheumatoid Arthritis," Curr Opin Rheumatol. 19(3):246-51 (2007).
Aumailley et al., "Identification of the Arg-Gly-Asp Sequence in Laminin A Chain as a Latent Cell-Binding Site Being Exposed in Fragment P1," FEBS Lett. 262(1):82-6 (1990).
Barassi et al., "Induction of Murine Mucosal CCR5-Reactive Antibodies as an Anti-Human Immunodeficiency Virus Strategy," J Virol. 79(11):6848-58 (2005).
Bloom and Young, "Paroviruses" in Fields Virology, 4th edition 2001, vol. 2, Chapter 70, Lippincott Williams Wilkins, Philadelphia, pp. 2359-2379 (2001).
Bousquet et al., "The Effect of treatment with Omalizumab, an Anti-IgE antibody, on Asthma Exacerbations and Emergency Medical Visits in Patients with Severe Persistent Asthma," Allergy. 60(3):302-8 (2005).
Chackerian et al., "Conjugation of a Self-Antigen to Papillomavirus-Like Particles Allows for Efficient Induction of Protective Autoanibodies," J Clin Invest. 108(3):415-23 (2001).
Chackerian et al., "Induction of Autoantibodies to Mouse CCr5 with Recombinant Papillomavirus Particles," Proc Natl Acad Sci U S A. 96(5):2373-8 (1999).
Chapman et al., "Structure, sequence, and function correlations among parvoviruses," Virology. 194(2):491-508 (1993).

(Continued)

*Primary Examiner* — Stacy B Chen
(74) *Attorney, Agent, or Firm* — Clark & Elbing LLP

(57) ABSTRACT

The present invention is related to a structural protein of a parvovirus with an amino acid insertion at the insertion site I-453, a library comprising the protein, a multimeric structure comprising the protein, a nucleic acid encoding the protein, a vector, virus, or cell comprising the nucleic acid, a process for the preparation of the protein, a medicament comprising the protein, nucleic acid, or multimeric structure as well as methods and uses involving the protein, nucleic acid, or multimeric structure.

16 Claims, 19 Drawing Sheets

(56) References Cited

OTHER PUBLICATIONS

Figure 1:
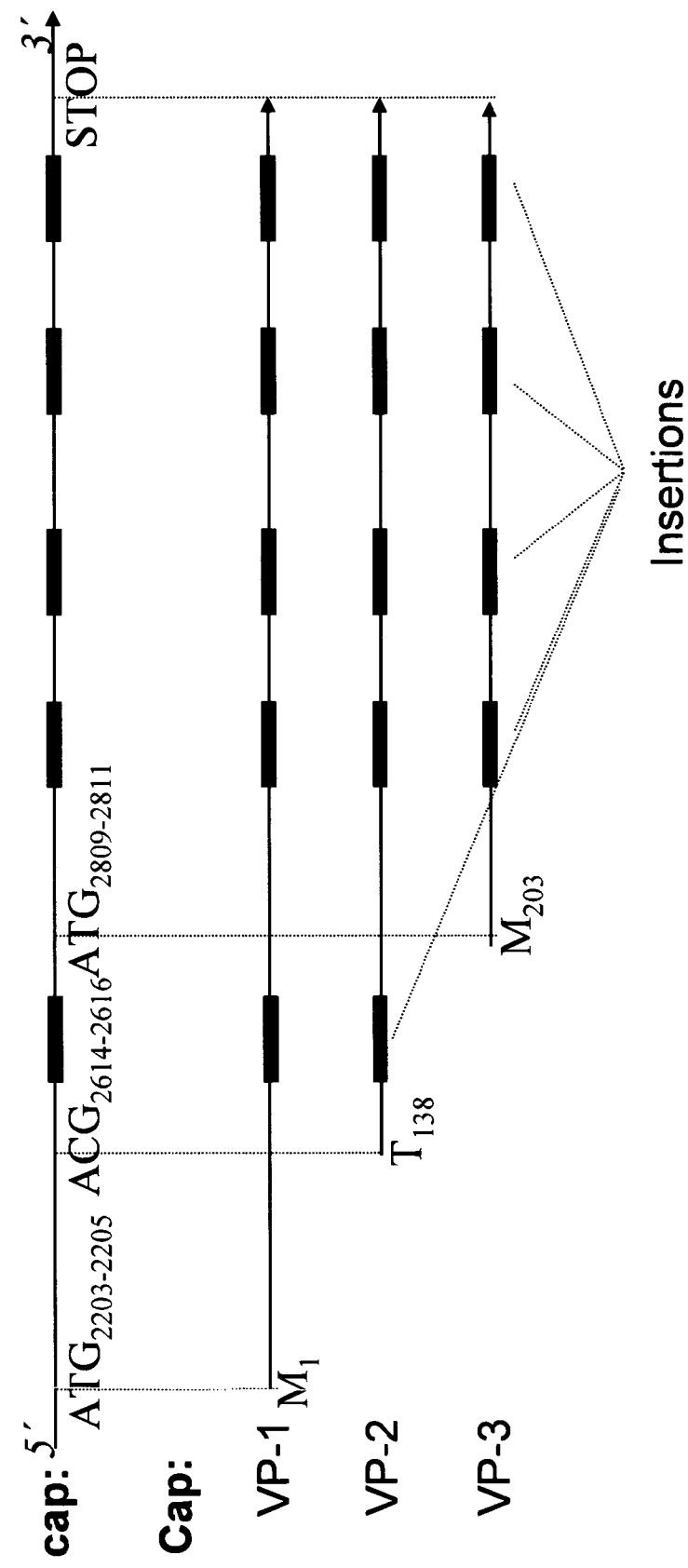

Chatterjee et al., "Idiotypic Antibody Immunotherapy of Cancer," Cancer Immunol Immunother. 38(2):75-82 (1994).
Cook et al., "Identification of Contact Residues in the IgE Binding Site of Human FcepsilonRIalpha," Biochemistry. 36(50):15579-88 (1997).
Corpet, "Multiple sequence alignment with hierarchical clustering," Nucleic Acids Res. 16(22):10881-90 (1988).
Dean et al., "Nuclear Entry of Nonviral Vectors," Gene Ther. 12(11):881-90 (2005).
Gamsjaeger et al., "Sticky Fingers: Zinc-Fingers as Protein-Recognition Motifs," Trends Biochem Sci. 32(2):63-70 (2007).
Garman et al., "Structure of the Fc Fragment of Human IgE Bound to its High-Affinity Receptor Fc EpsilonRI Alpha," Nature. 406(6793):259-66 (2000).
Girod et al., "Genetic Capsid Modifications Allow Efficient re-Targeting of Adeno-Associated Virus Type 2," Nat Med. 5(9):1052-6, 1438 (errata included) (1999).
Grifman et al., "Incorporation of Tumor-Targeting Peptides into Recombinant Adeno-Associated Virus Capsids," Mol Ther. 3(6):964-75 (2001).
Helm et al., The Mast Cell Binding Site on Human Immunoglobulin E. Nature 331(6152):180-3 (1988).
Helm et al., "Blocking of Passive Sensitization of Human Mast Cells and Basophil Granulocytes with IgE Antibodies by a Recombinant Human Epsilon-Chain Fragment of 76 Amino Acids," Proc Natl Acad Sci U S A. 86(23):9465-9 (1989).
Huttner et al., "Genetic modifications of the adeno-associated virus type 2 capsid reduce the affinity and the neutralizing effects of human serum antibodies," Gene Ther. 10(26):2139-47 (2003).
Jefferis, "What is an Idiotype?," Immunol Today. 14(3):119-21 (1993).
Jerne et al., "Recurrent Idiotopes and Internal Images," EMBO J. 1(2):243-7 (1982).
Jerne, "Towards a Network Theory of the Immune System," Ann Immunol (Paris). 125C(1-2):373-89 (1974).
Kay et al., "Viral Vectors for Gene Therapy: The Art of Turning Infectious Agents into Vehicles of Therapeutics," Nat Med. 7(1):33-40 (2001).
Kern et al., "Identification of a Heparin-Binding Motif on Adeno-Associated Virus Type 2 Capsids," J Virol. 77(20):11072-81 (2003).
Klenerman et al., "T Lymphocyte Responses Against Human Parvovirus B19: Small Virus, Big Response," Pathol Biol (Paris). 50(5):317-25 (2002).
Kricek et al., "IgE-Related Peptide Mimotopes. Basic Structures for Anti-Allergy Vaccine Development," Int Arch Aller Immunol. 118(2:4):222-3 (1999).
Laity et al., "Zinc Finger Proteins: New Insights into Structural and Functional Diversity" Curr Opin Struct Biol. 11(1):39-46 (2001).
Laughlin et al., "Cloning of Infectious Adeno-Associated Virus Genomes in Bacterial Plasmids," Gene. 23(1):65-73 (1983).
Levy et al., "Healthy IgE-Deficient Person," N Engl J Med. 283(10):541-2 (1970).
Li et al., "Overcoming Antigen Masking of Anti-Amyloidbeta Antibodies Reveals Breaking of B Cell Tolerance by Virus-Like Particles in Amyloidbeta Immunized Amyloid Precursor Protein Transgenic Mice," BMC Neurosci. 5:21 (2004).
Lieber, "AAV Display-Homing in on the Target," Nat Biotechnol. 21(9):1011-3 (2003).
Lux et al., "Green Fluorescent Protein-Tagged Adeno-Associated Virus Particles Allow the Study of CytoSolic and Nuclear Trafficking," J Virol. 79(18):11776-87 (2005).
Maheshri et al. "Directed Evolution of Adeno-Associated Virus Yields Enhanced Gene Delivery Vectors," Nat Biotechnol. 24(2):198-204 (2006).
Misumi et al., "Effects of Immunization with CCR5 Based Cycloimmunogen on Simian/HIVSF162P3 Challenge," J Immunol. 176(1):463-71 (2006).
Moskalenko et al., "Epitope mapping of human anti-adeno-associated virus type 2 neutralizing antibodies: implications for gene therapy and virus structure," J Virol. 74(4):1761-6 (2000).
Mueller et al., "Random Peptide Libraries Displayed on Adeno-Associated Virus to Select for Targeted Gene Therapy Vectors," Nat Biotechnol. 21(9):1040-6 (2003).
Muzyczka et al., "Paroviridae: The Viruses and Their Replication" in Fields Virology, 4th Edition 2001, vol. 2, Chapter 69, Lippincott Williams Wilkins, Philadelphia, pp. 2327-2359 (2001).
Nicklin et al., "Efficient and Selective AAV2-Mediated Gene Transfer Directed to Human Vascular Endothelial Cells," Mol Ther. 4(3):174-81 (2001).
Nygren et al., "Binding Proteins from Alternative Scaffolds," J Immunol Methods. 290(1-2):3-28 (2004).
Opie et al., "Identification of Amino Acid Residues in the Capsid Proteins of Adeno-Associated Virus Type 2 that Contribute to Heparan Sulfate Proteoglycan Binding," J Virol. 77(12):6995-7006 (2003).
Parker et al., "Scheme for Ranking Potential HLA-A2 Binding Peptides Based on Independent Binding of Individual Peptide Side-Chains," J Immunol. 152(1):163-175 (1994).
Perabo, "In Vitro Selection of Viral Vectors with Modified Tropism: The Adeno-Associated Virus Display," Mol Ther. 8(1):151-7 (2003).
Perabo et al., "Adeno-Associated Virus Display: In Vitro Evolution of AAV Retargeted Vectros," *Institut für Biochemie*. München, Ludwig-Maximilians-Universität, pp. 1-121 (2003).
Perabo et al., "Combinatorial Engineering of a Gene Therapy Vector: Directed Evolution of Adeno-Associated Associated Virus," J Gene Med. 8(2):155-162 (2006).
Perabo et al., "Heparan Sulfate Proteoglycan Binding Properties of Adeno-Associated Virus Retargeting Mutants and Consequences for Their In Vivo Tropism," J Virol. 80(14):7265-9 (2006).
Pfeifer et al., "Gene Therapy: Promises and Problems," Annu Rev Genomics Hum Genet 2:177-211 (2001).
Presta et al., "The Binding Site on Human Immunoglobulin E for its High Affinity Receptor," J Biol Chem. 269(42):26368-73 (1994).
Rabinowitz et al., "Insertional mutagenesis of AAV2 capsid and the production of recombinant virus," Virology. 265(2):274-85 (1999).
Ried et al., "Adeno-associated virus capsids displaying immunoglobulin-binding domains permit antibody-mediated vector retargeting to specific cell surface receptors," J Virol. 76(9):4559-66 (2002).
Riemer et al., "Active Induction of Tumor Specific IgE Antibodies by Oral Mimotope Vaccination," Cancer Res. 67(7):3406-11 (2007).
Rittershaus et al., "Vaccine-Induced Antibodies Inhibit CETP Activity In Vivo and Reduce Aortic Lesions in a Rabbit Model of Atherosclerosis," Arterioscler Thromb Vasc Biol. 20(9):2106-12 (2000).
Rudolf et al., "Epitone-Specific Antibody Response to IgE by Mimotope Immunization," J Immunol. 160(7):3315-21 (1998).
Rudolf et al., "Molecular Basis for Nonanaphylactogenicity of a Monoclonal Anti-IgE Antibody," J Immunol. 165(2):813-9 (2000).
Rueda et al., "Minor displacements in the insertion site provoke major differences in the induction of antibody responses by chimeric parvovirus-like particles," Virology. 263(1):89-99 (1999).
Ruffing et al., "Mutations in the Carboxy Terminus of Adeno-Associated Virus 2 Capsid Proteins Affect Viral Infectivity: Lack of an RGD Integrin-Binding Motif," J Gen Virol. 75 ( Pt 12):3385-92 (1994).
Shi et al., "RGD Inclusion in VP3 Provides Adeno-Associated Virus Type 2 (AAV2)-Based Vectors with a Heparan Sulfate-Independent Cell Entry Mechanism," Mol Ther. 7(4):515-25 (2003).
Shi et al., "Insertional Mutagenesis of the Adeno-Associated Virus Type 2 (AAV2) Capsid Gene and Generation of AAV2 Vectors Targeted to Alternative Cell-Surface Receptors," Hum Gene Ther. 12(14):1697-711 (2001).
Shi et al., "Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism," Hum Gene Ther. 17(3):353-61 (2006).
Smolen et al., "Therapeutic Strategies for Rheumatoid Arthritis," Nat Rev Drug Discov. 2(6):473-88 (2003).

(56) References Cited

OTHER PUBLICATIONS

Stachler et al., "Mosaic vectors comprised of modified AAV1 capsid proteins for efficient vector purification and targeting to vascular endothelial cells," Gene Ther. 13(11):926-31 (2006).

Stadler et al., "Mimotope and Anti-Idiotypic Vaccines to Induce an Anti-IgE Response," Int Arch Allergy Immunol. 118(2-4):119-21 (1999).

Summerford et al., "AlphaVbeta5 Integrin: A Co-Receptor for Adeno-Associated Virus Type 2 Infection," Nat Med. 5(1):78-82 (1999).

Theiss et al., "Enhancement of Gene Transfer with Recombinant Adeno-Associated Virus (rAAV) Vectors into Primary B-Cell Chronic Lymphocytic Leukemia Cells by CpG-oligodeoxynucleotides," Exp Hematol 31:1223-9 (2003).

Wu et al., "Mutational Analysis of the Adeno-Associated Virus Type 2 (AAV2) Capsid Gene and Construction of AAV2 Vectors with Altered Tropism," J Virol. 74(18):8635-47 (2000).

International Committee on Taxonomy of Viruses, "00.050. Parvoviridae—ICTVdB Index of Viruses," <http://www.ncbi.nlm.nih.gov/ICTVdb/Ictv/fs_parvo.htm#SubFamily1>, retreived on Mar. 12, 2007 (8 pages).

Mathakia, "The Paovirus Family," <http://virus.stanford.edu/parvo/parvovirus.html>, retrieved on Mar. 12, 2007 (5 pages).

Ruffing, Major Coat Protein VP1 [Adeno-associated Virus-2], Genpept Accession No. 2906023, retreived on Jun. 8, 2010 (1 page).

\* cited by examiner

Fig. 2

```
AAV-2    IDQYLYYLSRTN-TPSGTTTQSRLQFSQAGAS
AAV-5    LVDQYLYRFVSTN-NTGGVQFNKNLAGRYANT
AAV-1    IDQYLYYLNRTQ-NQSGSAQNKDLLFSRGSPA
AAV-6    IDQYLYYLNRTQ-NQSGSAQNKDLLFSRGSPA
AAV-8    IDQYLYYLSRTQ-TTGGTANTQTLGFSQGGPN
AAV-10   IDQYLYYLSRTQ-STGGTQGTQQLLFSQAGPA              ← I-453
AAV-3B   DQYLYYLNRTQGTTSGTTNQSRLLFSQAGPQ
AAV-7    DQYLYYLARTQSNPGGTAGNRELQFYQGGPS
AAV-4    PLIDQYLWGL---QSTTTGTTLNAGTATTNFTKL
AAV-11   PLLDQYLWHL---QSTTSGETLNQGNAATTFGKI
b-AAV    PLLDQYLWEL---QSTTSGGTLNQGNSATNFAKL
FPV      PFLNSLPQSEGATNFGDIGVQQDKRRGVTQMGNT
CPV      PFLNSLPQSEGATNFGDIGVQQDKRRGVTQMGNT
B19      NPLYGSRLGVPDTLGGDP-KFRSLTHEDHAIQ
GPV      LKDRQYLLQPGPVSATYTEGEASSLPAQNIL
MVM      QPPLL-STFP-EADTDAGTLTAQG-SRHGATQMEVNW

Consensus ....dqyly.l..tq..g........q....
```

Fig. 3-1

```
             1                                                           50
    AAV-1    MAADGYLPDW  LEDNLSEGIR  EWWDLKPGAP  KPKANQQKQD  DGRGLVLPGY
    AAV-6    MAADGYLPDW  LEDNLSEGIR  EWWDLKPGAP  KPKANQQKQD  DGRGLVLPGY
    AAV-2    MAADGYLPDW  LEDTLSEGIR  QWWKLKPGPP  PPKPAERHKD  DSRGLVLPGY
    AAV-3B   MAADGYLPDW  LEDNLSEGIR  EWWALKPGVP  QPKANQQHQD  NRRGLVLPGY
    AAV-7    MAADGYLPDW  LEDNLSEGIR  EWWDLKPGAP  KPKANQQKQD  NGRGLVLPGY
    AAV-8    MAADGYLPDW  LEDNLSEGIR  EWWALKPGAP  KPKANQQKQD  DGRGLVLPGY
    AAV-10   MAADGYLPDW  LEDNLSEGIR  EWWDLKPGAP  KPKANQQKQD  DGRGLVLPGY
    AAV-4     MTDGYLPDW  LEDNLSEGVR  EWWALQPGAP  KPKANQQHQD  NARGLVLPGY
    AAV-11   MAADGYLPDW  LEDNLSEGIR  EWWDLKPGAP  KPKANQQKQD  DGRGLVLPGY
    b-AAV    MSFVDHPPDW  LE-SIGDGFR  EFLGLEAGPP  KPKANQQKQD  NARGLVLPGY
    AAV-5    MSFVDHPPDW  LEE-VGEGLR  EFLGLEAGPP  KPKPNQQHQD  QARGLVLPGY
    GPV
    B19
    MVM
    FPV
    CPV
Consensus    ..........  ..........  ..........  ..........  ..........

51                                                          100
    AAV-1    KYLGPFNGLD  KGEPVNAADA  AALEHDKAYD  QQLKAGDNPY  LRYNHADAEF
    AAV-6    KYLGPFNGLD  KGEPVNAADA  AALEHDKAYD  QQLDSGDNPY  LRYNHADAEF
    AAV-2    KYLGPFNGLD  KGEPVNEADA  AALEHDKAYD  RQLDSGDNPY  LKYNHADAEF
    AAV-3B   KYLGPGNGLD  KGEPVNEADA  AALEHDKAYD  QQLKAGDNPY  LKYNHADAEF
    AAV-7    KYLGPFNGLD  KGEPVNAADA  AALEHDKAYD  QQLKAGDNPY  LRYNHADAEF
    AAV-8    KYLGPFNGLD  KGEPVNAADA  AALEHDKAYD  QQLQAGDNPY  LRYNHADAEF
    AAV-10   KYLGPFNGLD  KGEPVNAADA  AALEHDKAYD  QQLKAGDNPY  LRYNHADAEF
    AAV-4    KYLGPGNGLD  KGEPVNAADA  AALEHDKAYD  QQLKAGDNPY  LKYNHADAEF
    AAV-11   KYLGPFNGLD  KGEPVNAADA  AALEHDKAYD  QQLKAGDNPY  LRYNHADAEF
    b-AAV    KYLGPGNGLD  KGDPVNFADE  VAREHDLSYQ  KQLEAGDNPY  LKYNHADAEF
    AAV-5    NYLGPGNGLD  RGEPVNRADE  VAREHDISYN  EQLEAGDNPY  LKYNHADAEF
    GPV
    B19
    MVM
    FPV
    CPV
Consensus    ..........  ..........  ..........  ..........  ..........

101                                                         150
    AAV-1    QERLQEDTSF  GGNLGRAVFQ  AKKRVLEPLG  LVEEGAKTAP  G-KKRPVEQS
    AAV-6    QERLQEDTSF  GGNLGRAVFQ  AKKRVLEPFG  LVEEGAKTAP  G-KKRPVEQS
    AAV-2    QERLKEDTSF  GGNLGRAVFQ  AKKRVLEPLG  LVEEPVKTAP  G-KKRPVEHS
    AAV-3B   QERLQEDTSF  GGNLGRAVFQ  AKKRILEPLG  LVEEAAKTAP  G-KKRPVDQS
    AAV-7    QERLQEDTSF  GGNLGRAVFQ  AKKRVLEPLG  LVEEGAKTAP  A-KKRPVEPS
    AAV-8    QERLQEDTSF  GGNLGRAVFQ  AKKRVLEPLG  LVEEGAKTAP  G-KKRPVEPS
    AAV-10   QERLQEDTSF  GGNLGRAVFQ  AKKRVLEPLG  LVEEAAKTAP  G-KKRPVEPS
    AAV-4    QQRLQGDTSF  GGNLGRAVFQ  AKKRVLEPLG  LVEQAGETAP  G-KKRPLIES
    AAV-11   QERLQEDTSF  GGNLGRAVFQ  AKKRVLEPLG  LVEEGAKTAP  G-KKRPL-ES
    b-AAV    QEKLASDTSF  GGNLGKAVFQ  AKKRILEPLG  LVETPDKTAP  AAKKRPLEQS
    AAV-5    QEKLADDTSF  GGNLGKAVFQ  AKKRVLEPFG  LVEEGAKTAP  TGKR-----I
    GPV
    B19
    MVM
    FPV
    CPV
Consensus    ..........  ..........  ..........  ..........  ..........
```

Fig. 3-2

```
             151                                                              200
    AAV-1    PQE-PDSSSG  IGKTGQQPAK  KRLNFGQTGD  SESVPDPQPL  GEPPATPAAV
    AAV-6    PQE-PDSSSG  IGKTGQQPAK  KRLNFGQTGD  SESVPDPQPL  GEPPATPAAV
    AAV-2    PVE-PDSSSG  TGKAGQQPAR  KRLNFGQTGD  ADSVPDPQPL  GQPPAAPSGL
   AAV-3B    PQE-PDSSSG  VGKSGKQPAR  KRLNFGQTGD  SESVPDPQPL  GEPPAAPTSL
    AAV-7    PQRSPDSSTG  IGKKGQQPAR  KRLNFGQTGD  SESVPDPQPL  GEPPAAPSSV
    AAV-8    PQRSPDSSTG  IGKKGQQPAR  KRLNFGQTGD  SESVPDPQPL  GEPPAAPSGV
   AAV-10    PQRSPDSSTG  IGKKGQQPAK  KRLNFGQTGE  SESVPDPQPI  GEPPAGPSGL
    AAV-4    PQQ-PDSSTG  IGKKGKQPAK  KKLVF----E  DETGAGDGPP  -EGSTSGAMS
   AAV-11    PQE-PDSSSG  IGKKGKQPAR  KRLNF----E  EDTGAGDGPP  -EGSDTSAMS
    b-AAV    PQE-PDSSSG  VGKKGKQPAR  KRLNF----D  DEPGAGDGPP  PEGPSSGAMS
    AAV-5    DDHFPKRKKA  RTEEDSKPST  SS-------D  AEAGPSGSQQ  LQIPAQPASS
      GPV
      B19
      MVM                                        MSDGTSQPD   GGNAVHSAAR
      FPV                                        MSDGAVQPD   GGQP---AVR
      CPV
Consensus    ..........  ..........  ..........  .........p.  ..........

201                                                              250
    AAV-1    -GPTTMASGG  GAPMADNNEG  ADGVGNASGN  WHCDSTWLGD  RVITTSTRTW
    AAV-6    -GPTTMASGG  GAPMADNNEG  ADGVGNASGN  WHCDSTWLGD  RVITTSTRTW
    AAV-2    -GTNTMATGS  GAPMADNNEG  ADGVGNSSGN  WHCDSTWMGD  RVITTSTRTW
   AAV-3B    -GSNTMASGG  GAPMADNNEG  ADGVGNSSGN  WHCDSQWLGD  RVITTSTRTW
    AAV-7    -GSGTVAAGG  GAPMADNNEG  ADGVGNASGN  WHCDSTWLGD  RVITTSTRTW
    AAV-8    -GPNTMAAGG  GAPMADNNEG  ADGVGSSSGN  WHCDSTWLGD  RVITTSTRTW
   AAV-10    -GSGTMAAGG  GAPMADNNEG  ADGVGSSSGN  WHCDSTWLGD  RVITTSTRTW
    AAV-4    -DDSEMRAAA  GGAAVEGGQG  ADGVGNASGD  WHCDSTWSEG  HVTTTSTRTW
   AAV-11    -SDIEMRAAP  GGNAVDAGQG  SDGVGNASGD  WHCDSTWSEG  KVTTTSTRTW
    b-AAV    -TETEMRAAA  GGNGGDAGQG  AEGVGNASGD  WHCDSTWSES  HVTTTSTRTW
    AAV-5    LGADTMSAGG  GGPLGDNNQG  ADGVGNASGD  WHCDSTWMGD  RVVTKSTRTW
      GPV         MAEGG  GGAMGDSSGG  ADGVGNASGN  WHCDSQWMGN  TVITKTTRTW
      B19         MTSV   NSAEASTGAG  GGGSNPVKSM  WSEGATFSAN  SVTCTFSRQF
      MVM    VERAADGPGG  SGGGGSGG-G  GVGVSTGSYD  NQTHYRFLGD  GWVEITALAT
      FPV    NERATGSGNG  SGGGGGGGSG  GVGISTGTFN  NQTEFKFLEN  GWVEITANSS
      CPV                            GVGISTGTFN  NQTEFKFLEN  GWVEITANSS
Consensus    ........gg  gg.....g.g  ..Gvg..sg.  whcdstw.g.  .v.t..trtw 251                                                              300
    AAV-1    ALPTYNNHLY  KQISSASTG-  ASND------  ---NHYFGYS  TPWGYFDFNR
    AAV-6    ALPTYNNHLY  KQISSASTG-  ASND------  ---NHYFGYS  TPWGYFDFNR
    AAV-2    ALPTYNNHLY  KQISSQS-G-  ASND------  ---NHYFGYS  TPWGYFDFNR
   AAV-3B    ALPTYNNHLY  KQISSQS-G-  ASND------  ---NHYFGYS  TPWGYFDFNR
    AAV-7    ALPTYNNHLY  KQISSETAG-  STND------  ---NTYFGYS  TPWGYFDFNR
    AAV-8    ALPTYNNHLY  KQISNGTSGG  ATND------  ---NTYFGYS  TPWGYFDFNR
   AAV-10    ALPTYNNHLY  KQISNGTSGG  STND------  ---NTYFGYS  TPWGYFDFNR
    AAV-4    VLPTYNNHLY  KRLGE-----  SLQS------  ---NTYNGFS  TPWGYFDFNR
   AAV-11    VLPTYNNHLY  LRLGT-----  TSSS------  ---NTYNGFS  TPWGYFDFNR
    b-AAV    VLPTYNNHLY  LRLGS-----  SNAS------  ---DTFNGFS  TPWGYFDFNR
    AAV-5    VLPSYNNHQY  REIKSGSVD-  GSNA------  ---NAYFGYS  TPWGYFDFNR
      GPV    VLPSYNNHIY  KAITSGTS--  QDAN------  ---VQYAGYS  TPWGYFDFNR
      B19    LIPYDPEHHY  KVFSPAASSC  HNASGKEAKV  CTISPIMGYS  TPWRYLDFNA
      MVM    RLVHLNMPKS  ENYCRIRVHN  TTDTSVKGNM  AKDDAHEQIW  TPWSLVDANA
      FPV    RLVHLNMPES  ENYKRVVVNN  MDKTAVKGNM  ALDDIHVEIV  TPWSLVDANA
      CPV    RLVHLNMPES  ENYRRVVVNN  MDKTAVNGNM  ALDDIHAQIV  TPWSLVDANA
Consensus    .lp.ynnh.y  ..........  ..........  .......gys  TPWgyfDfNr
```

Fig. 3-3

```
                301                                                           350
    AAV-1   FHCHFSPRDW QRLINNNWGF RPKRLNFKLF NIQVKEVTTN DGV-TT---I
    AAV-6   FHCHFSPRDW QRLINNNWGF RPKRLNFKLF NIQVKEVTTN DGV-TT---I
    AAV-2   FHCHFSPRDW QRLINNNWGF RPKRLNFKLF NIQVKEVTQN DGT-TT---I
   AAV-3B   FHCHFSPRDW QRLINNNWGF RPKKLSFKLF NIQVKEVTQN DGT-TT---I
    AAV-7   FHCHFSPRDW QRLINNNWGF RPKKLRFKLF NIQVKEVTTN DGV-TT---I
    AAV-8   FHCHFSPRDW QRLINNNWGF RPKRLSFKLF NIQVKEVTQN EGT-KT---I
   AAV-10   FHCHFSPRDW QRLINNNWGF RPKRLSFKLF NIQVKEVTQN EGT-KT---I
    AAV-4   FHCHFSPRDW QRLINNNWGM RPKAMRVKIF NIQVKEVTTS NGE-TT---V
   AAV-11   FHCHFSPRDW QRLINNNWGL RPKAMRVKIF NIQVKEVTTS NGE-TT---V
    b-AAV   FHCHFSPRDW QRLINNHWGL RPKSMQVRIF NIQVKEVTTS NGE-TT---V
    AAV-5   FHSHWSPRDW QRLINNYWGF RPRSLRVKIF NIQVKEVTVQ DST-TT---I
      GPV   FHCHFSPRDW QRLINNHWGI RPKSLKFKIF NVQVKEVTTQ DQT-KT---I
      B19   LNLFFSPLEF QHLIENYGSI APDALTVTIS EIAVKDVTDK TGGGVQ---V
      MVM   WGVWLQPSDW QYICNTMSQL NLVSLDQEIF NVVLKTVTEQ DSGGQAIKIY
      FPV   WGVWFNPGDW QLIVNTMSEL HLVSFEQEIF NVVLKTVSES ATQPPT-KVY
      CPV   WGVWFNPGDW QLIVNTMSEL HLVSFEQEIF NVVLKTVSES ATQPPT-KVY
Consensus   fh.hfsPr#w Qrli#n.wg. rp.sl...if #!qvKeVt.. .....t....

351                                                           400
    AAV-1   ANNLTSTVQV FSDSEYQLPY VLGSAHQGCL PPFPADVFMI PQYGYLTLN-
    AAV-6   ANNLTSTVQV FSDSEYQLPY VLGSAHQGCL PPFPADVFMI PQYGYLTLN-
    AAV-2   ANNLTSTVQV FTDSEYQLPY VLGSAHQGCL PPFPADVFMV PQYGYLTLN-
   AAV-3B   ANNLTSTVQV FTDSEYQLPY VLGSAHQGCL PPFPADVFMV PQYGYLTLN-
    AAV-7   ANNLTSTIQV FSDSEYQLPY VLGSAHQGCL PPFPADVFMI PQYGYLTLN-
    AAV-8   ANNLTSTIQV FTDSEYQLPY VLGSAHQGCL PPFPADVFMI PQYGYLTLN-
   AAV-10   ANNLTSTIQV FTDSEYQLPY VLGSAHQGCL PPFPADVFMI PQYGYLTLN-
    AAV-4   ANNLTSTVQI FADSSYELPY VMDAGQEGSL PPFPNDVFMV PQYGYCGLV-
   AAV-11   ANNLTSTVQI FADSSYELPY VMDAGQEGSL PPFPNDVFMV PQYGYCGIV-
    b-AAV   SNNLTSTVQI FADSTYELPY VMDAGQEGSL PPFPNDVFMV PQYGYCGLV-
    AAV-5   ANNLTSTVQV FTDDDYQLPY VVGNGTEGCL PAFPPQVFTL PQYGYATLN-
      GPV   ANNLTSTIQV FTDDEHQLPY VLGSATEGTM PPFPSDVYAL PQYGYCTMH-
      B19   TDSTTGRLCM LVDHEYKYPY VLGQGQDTLA PELPIWVYFP PQYAYLTVGD
      MVM   NNDLTACMMV AVDSNNILPY TPAANSMETL GFYPWKPTIA SPYRYYFCVD
      FPV   NNDLTASLMV ALDSNNTMPF TPAAMRSETL GFYPWKPTIP TPWRYYFQWD
      CPV   NNDLTASLMV ALDSNNTMPF TPAAMRSETL GFYPWKPTIP TPWRYYFQWD
Consensus   .#nlTst.qv f.Ds.y.lP% v.g....g.l p.fP...v... pqygY.t...

401                                                           450
    AAV-1   ------NGS- --QAVG---- -----RSSFY CLEYF-PSQM LRTGNNF-TF
    AAV-6   ------NGS- --QAVG---- -----RSSFY CLEYF-PSQM LRTGNNF-TF
    AAV-2   ------NGS- --QAVG---- -----RSSFY CLEYF-PSQM LRTGNNF-TF
   AAV-3B   ------NGS- --QAVG---- -----RSSFY CLEYF-PSQM LRTGNNF-QF
    AAV-7   ------NGS- --QSVG---- -----RSSFY CLEYF-PSQM LRTGNNF-EF
    AAV-8   ------NGS- --QAVG---- -----RSSFY CLEYF-PSQM LRTGNNF-QF
   AAV-10   ------NGS- --QAVG---- -----RSSFY CLEYF-PSQM LRTGNNF-EF
    AAV-4   ------TGNT SQQQTD---- -----RNAFY CLEYF-PSQM LRTGNNF-EI
   AAV-11   ------TGE- NQNQTD---- -----RNAFY CLEYF-PSQM LRTGNNF-EM
    b-AAV   ------TGGS SQNQTD---- -----RNAFY CLEYF-PSQM LRTGNNF-EM
    AAV-5   ------RDN- TENPTE---- -----RSSFF CLEYF-PSKM LRTGNNF-EF
      GPV   ------TNQN GARFND---- -----RSAFY CLEYF-PSQM LRTGNNF-EF
      B19   VNTQGISGDS KKLASE---- -----ESAFY VLEHS-SFQL LGTGGTA-TM
      MVM   RDLSVTYENQ EGTIEHNVMG TPKGMNSQFF TIENTQQITL LRTGDEFATG
      FPV   RTLIPSHTGT SGTPTNVYHG TDPD-DVQFY TIENSVPVHL LRTGDEFATG
      CPV   RTLIPSHTGT SGTPTNIYHG TDPD-DVQFY TIENSVPVHL LRTGDEFATG
Consensus   .......... .......... .....rs.F% clEyf.psq$ LrTGnnf.t.
```

Fig. 3-4

```
                451                                                     500
     AAV-1  SYTFEEVPFH  SSYAHSQSLD  RLMNPLIDQY  LYYLNRTQ-N  QSGSAQNKDL
     AAV-6  SYTFEDVPFH  SSYAHSQSLD  RLMNPLIDQY  LYYLNRTQ-N  QSGSAQNKDL
     AAV-2  SYTFEDVPFH  SSYAHSQSLD  RLMNPLIDQY  LYYLSRTN-T  PSGTTTQSRL
    AAV-3B  SYTFEDVPFH  SSYAHSQSLD  RLMNPLIDQY  LYYLNRTQGT  TSGTTNQSRL
     AAV-7  SYSFEDVPFH  SSYAHSQSLD  RLMNPLIDQY  LYYLARTQSN  PGGTAGNREL
     AAV-8  TYTFEDVPFH  SSYAHSQSLD  RLMNPLIDQY  LYYLSRTQTT  -GGTANTQTL
    AAV-10  SYTFEDVPFH  SSYAHSQSLD  RLMNPLIDQY  LYYLSRTQST  -GGTQGTQQL
     AAV-4  TYSFEKVPFH  SMYAHSQSLD  RLMNPLIDQY  LWGLQSTTTG  TTLNAGTATT
    AAV-11  AYNFEKVPFH  SMYAHSQSLD  RLMNPLLDQY  LWHLQSTTSG  ETLNQGNAAT
     b-AAV  VYKFENVPFH  SMYAHSQSLD  RLMNPLLDQY  LWELQSTTSG  GTLNQGNSAT
     AAV-5  TYNFEEVPFH  SSFAPSQNLF  KLANPLVDQY  LYRFVSTN--  -----NTGGV
       GPV  TFDFEEVPFH  SMFAHSQDLD  RLMNPLVDQY  LWNFNEVD--  -----SSRNA
       B19  SYKFPPVPPE  NLEGCSQHFY  EMYNPLYGSR  LGVPDTL---  ------GGDP
       MVM  TYYFDTNPVK  LTHTWQTNRQ  LGQPPLLSTF  PEAD--TDAG  TL-TAQGSRH
       FPV  TFFFDCKPCR  LTHTWQTNRA  LGLPPFLNSL  PQSEGATNFG  DIGVQQDKRR
       CPV  TFFFDCKPCR  LTHTWQTNRA  LGLPPFLNSL  PQSEGATNFG  DIGVQQDKRR
 Consensus  t%.Fe.vPfh  s...a.sq.l. .l.nPl.dqy  l.....t...  ..........

501                                                     550
     AAV-1  LFSRGSPAGM  SVQPKNWLPG  PCYRQQRVSK  TKTDN-----  NNSNFTWTGA
     AAV-6  LFSRGSPAGM  SVQPKNWLPG  PCYRQQRVSK  TKTDN-----  NNSNFTWTGA
     AAV-2  QFSQAGASDI  RDQSRNWLPG  PCYRQQRVSK  TSADN-----  NNSEYSWTGA
    AAV-3B  LFSQAGPQSM  SLQARNWLPG  PCYRQQRLSK  TANDN-----  NNSNFPWTAA
     AAV-7  QFYQGGPSTM  AEQAKNWLPG  PCFRQQRVSK  TLDQN-----  NNSNFAWTGA
     AAV-8  GFSQGGPNTM  ANQAKNWLPG  PCYRQQRVST  TTGQN-----  NNSNFAWTAG
    AAV-10  LFSQAGPANM  SAQAKNWLPG  PCYRQQRVST  TLSQN-----  NNSNFAWTGA
     AAV-4  NFTKLRPTNF  SNFKKNWLPG  PSIKQQGFSK  TANQNYKIPA  TGSDSLIKYE
    AAV-11  TFGKIRSGDF  AFYRKNWLPG  PCVKQQRFSK  TASQNYKIPA  SGGNALLKYD
     b-AAV  NFAKLTKTNF  SGYRKNWLPG  PMMKQQRFSK  TASQNYKIPQ  GRNNSLLHYE
     AAV-5  QFNKNLAGRY  ANTYKNWFPG  PMGRTQGWNL  GSGVN-----  RASVSAFATT
       GPV  QFKKAVKGAY  GTMGRNWLPG  PKFLDQRVRA  YTGGT---DN  YANWNIWSNG
       B19  KFRSLTHEDH  AIQPQNFMPG  PLVNSVSTKE  GDSFN-----  TGAGKALTGL
       MVM  GATQM-EVNW  VSEAIRTRPA  QVGFCQPHND  FEASR-----  AGPFAAPKVP
       FPV  GVTQMGNTDY  ITEATIMRPA  EVGYSAPYYS  FEAST-----  QGPFKTPIAA
       CPV  GVTQMGNTNY  ITEATIMRPA  EVGYSAPYYS  FEAST-----  QGPFKTPIAA
 Consensus  .f........  .....nw.Pg  p....q....  ....n.....  .g........

551                                                     600
     AAV-1  SKYNLNGRES  IINPGTAMAS  HKD-DEDKFF  PMSGVMIFGK  ESAGASNTAL
     AAV-6  SKYNLNGRES  IINPGTAMAS  HKD-DKDKFF  PMSGVMIFGK  ESAGASNTAL
     AAV-2  TKYHLNGRDS  LVNPGPAMAS  HKD-DEEKFF  PQSGVLIFGK  QGSEKTNVDI
    AAV-3B  SKYHLNGRDS  LVNPGPAMAS  HKD-DEEKFF  PMHGNLIFGK  EGTTASNAEL
     AAV-7  TKYHLNGRNS  LVNPGVAMAT  HKD-DEDRFF  PSSGVLIFGK  TGAT-NKTTL
     AAV-8  TKYHLNGRNS  LANPGIAMAT  HKD-DEERFF  PSNGILIFGK  QNAARDNADY
    AAV-10  TKYHLNGRDS  LVNPGVAMAT  HKD-DEERFF  PSSGVLMFGK  QGAGRDNVDY
     AAV-4  THSTLDGRWS  ALTPGPPMAT  AGP-ADSKF-  SNSQLIFAGP  KQNGNTATVP
    AAV-11  THYTLNNRWS  NIAPGPPMAT  AGP-SDGDF-  SNAQLIFPGP  SVTGNTTTSA
     b-AAV  TRTTLDGRWS  NFAPGTAMAT  AAN-DATDF-  SQAQLIFAGP  NITGNTTTDA
     AAV-5  NRMELEGASY  QVPPQPNGMT  NNL-QGSNTY  ALENTMIFNS  QPANPGTTAT
       GPV  NKVNLKDRQY  LLQPGPVSAT  YTE-GEASSL  PAQNILGIAK  DPYRSGSTTA
       B19  STGTSQNTRI  SLRPGPVSQP  YHHWDTDKYV  TGINAISHGQ  TTYGNAEDKE
       MVM  ADVTQGMDRE  --ANGSVRYS  YGKQHGENWA  AHGPAPERYT  WDETNFGSGR
       FPV  GRGGAQTDEN  QAADGDPRYA  FGRQHGQKTT  TTGETPERFT  YI-AHQDTGR
       CPV  GRGGAQTDEN  QAADGNPRYA  FGRQHGQKTT  TTGETPERFT  YI-AHQDTGR
 Consensus  ....l.....  ...pGp....  ..........  ..........  .......t..
```

Fig. 3-5

```
                                                           I-587
              601                                                      650
     AAV-1    ---DNVMITD EEEIKATNPV ATERFGTVAV NFQSSSTDPA TGDVHAMGAL
     AAV-6    ---DNVMITD EEEIKATNPV ATERFGTVAV NLQSSSTDPA TGDVHVMGAL
     AAV-2    ---EKVMITD EEEIRTTNPV ATEQYGSVST NLQRGNRQAA TADVNTQGVL
     AAV-3B   ---DNVMITD EEEIRTTNPV ATEQYGTVAN NLQSSNTAPT TRTVNDQGAL
     AAV-7    ---ENVLMTN EEEIRPTNPV ATEEYGIVSS NLQAANTAAQ TQVVNNQGAL
     AAV-8    ---SDVMLTS EEEIKTTNPV ATEEYGIVAD NLQQQNTAPQ IGTVNSQGAL
     AAV-10   ---SSVMLTS EEEIKTTNPV ATEQYGVVAD NLQQANTGPI VGNVNSQGAL
     AAV-4    ---GTLIFTS EEELAATNAT DTDMWGNLPG GDQSNSNLPT VDRLTALGAV
     AAV-11   ---NNLLFTS EEEIAATNPR DTDMFGQIAD NNQNATTAPI TGNVTAMGVL
     b-AAV    ---NNLMFTS EDELRATNPR DTDLFGHLAT NQQNATVPT VDDVDGVGVY
     AAV-5    YLEGNMLITS ESETQPVNRV AYNVGGQMAT NNQSSTAPA TGTYNLQEIV
     GPV      GI-SDIMVTE EQEVAPTNGV GWKPYGRTVT NEQNTTAPT SSDLDVLGAL
     B19      YQQGVGRFPN EKE-----QL KQLQGLNMHT YFPNKGTQQY TDQIE-RPLM
     MVM      DTRDGFIQSA PLVV----PP PLNGILTNAN PIGTKNDIHF SNVFNSYGPL
     FPV      YPEGDWIQNI NFNL----PV TNDNVLLPTD PIGGKTGINY TNIFNTYGPL
     CPV      YPEGDWIQNI NFNL----PV TNDNVLLPTD PIGGKTGINY TNIFNTYGPL
   Consensus  ........t. e.e....npv .....g.... ..q..tt... t...n..g.l 651                                                      700
     AAV-1    PGMVWQDRDV YLQGPIWAKI PHTDGHFHPS -PLMGGFGLK NPPPQILIKN
     AAV-6    PGMVWQDRDV YLQGPIWAKI PHTDGHFHPS -PLMGGFGLK HPPPQILIKN
     AAV-2    PGMVWQDRDV YLQGPIWAKI PHTDGHFHPS -PLMGGFGLK HPPPQILIKN
     AAV-3B   PGMVWQDRDV YLQGPIWAKI PHTDGHFHPS -PLMGGFGLK HPPPQIMIKN
     AAV-7    PGMVWQNRDV YLQGPIWAKI PHTDGNFHPS -PLMGGFGLK HPPPQILIKN
     AAV-8    PGMVWQNRDV YLQGPIWAKI PHTDGNFHPS -PLMGGFGLK HPPPQILIKN
     AAV-10   PGMVWQNRDV YLQGPIWAKI PHTDGNFHPS -PLMGGFGLK HPPPQILIKN
     AAV-4    PGMVWQNRDI YYQGPIWAKI PHTDGHFHPS -PLIGGFGLK HPPPQIFIKN
     AAV-11   PGMVWQNRDI YYQGPIWAKI PHADGHFHPS -PLIGGFGLK HPPPQIFIKN
     b-AAV    PGMVWQDRDI YYQGPIWAKI PHTDGHFHPS -PLIGGFGLK SPPPQIFIKN
     AAV-5    PGSVWMERDV YLQGPIWAKI PETGAHFHPS -PAMGGFGLK HPPPMMLIKN
     GPV      PGMVWQNRDI YLQGPIGAKI PKTDGKFHPS -PNLGGFGLH NPPPQVFIKN
     B19      VGSVWNRRAL HYESQLWSKI PNLDDSFKTQ FAALGGWGLH QPPPQIFLKI
     MVM      TTFS-HPSPV YPQGQIWDK- -ELDLEHKPR LHITAPFVCK NNAPGQMLVR
     FPV      TALN-NVPPV YPNGQIWDK- -EFDTDLKPR LHINAPFVCQ NNCPGQLFVK
     CPV      TALN-NVPPV YPNGQIWDK- -EFDTDLKPR LHVNAPFVCQ NNCPGQLFVK
   Consensus  pg.vw..rdv y.#gpiwaKi p..D..fhps .p...ggfglk .ppPq..ikn 701                                                      750
     AAV-1    TPVPANPPAE FSATKFASFI TQYSTGQVSV EIEWEL-QKE NSKRWNPEVQ
     AAV-6    TPVPANPPAE FSATKFASFI TQYSTGQVSV EIEWEL-QKE NSKRWNPEVQ
     AAV-2    TPVPANPSTT FSAAKFASFI TQYSTGQVSV EIEWEL-QKE NSKRWNPEIQ
     AAV-3B   TPVPANPPTT FSPAKFASFI TQYSTGQVSV EIEWEL-QKE NSKRWNPEIQ
     AAV-7    TPVPANPPEV FTPAKFASFI TQYSTGQVSV EIEWEL-QKE NSKRWNPEIQ
     AAV-8    TPVPADPPTT FNQSKLNSFI TQYSTGQVSV EIEWEL-QKE NSKRWNPEIQ
     AAV-10   TPVPADPPTT FSQAKLASFI TQYSTGQVSV EIEWEL-QKE NSKRWNPEIQ
     AAV-4    TPVPANPATT FSSTPVNSFI TQYSTGQVSV QIDWEI-QKE RSKRWNPEVQ
     AAV-11   TPVPANPATT FTAARVDSFI TQYSTGQVAV QIEWEI-EKE RSKRWNPEVQ
     b-AAV    TPVPANPATT FSPARINSFI TQYSTGQVAV KIEWEI-QKE RSKRWNPEVQ
     AAV-5    TPVPGN-ITS FSDVPVSSFI TQYSTGQVTV EMEWEL-KKE NSKRWNPEIQ
     GPV      TPVPADPPVE YVHQKWNSYI TQYSTGQCTV EMVWEL-RKE NSKRWNPEIQ
     B19      --LPQSGPIG GIKSMGITTL VQYAVGIMTV TMTFKLGPRK ATGRWNPQPG
     MVM      LGPNLTDQYD PNG-ATLSRI VTYGTFFWKG KLTMRA-KLR ANTTWNPVYQ
     FPV      VAPNLTNQYD PDASANMSRI VTYSDFWWKG KLVFKA-KLR ASHTWNPIQQ
     CPV      VAPNLTNEYD PDASANMSRI VTYSDFWWKG KLVFKA-KLR ASHTWNPIQQ
   Consensus  tpvp...... ........s.i tqYstgq..v ...wel..ke .skrWNPe.q
```

Fig. 3-6

```
              751                                                           799
    AAV-1   YTSNYAKSAN  V---DFTVDN  NGLYTEPRPI  GTRYLTRPL
    AAV-6   YTSNYAKSAN  V---DFTVDN  NGLYTEPRPI  GTRYLTRPL
    AAV-2   YTSNYNKSVN  V---DFTVDT  NGVYSEPRPI  GTRYLTRNL
   AAV-3B   YTSNYNKSVN  V---DFTVDT  NGVYSEPRPI  GTRYLTRNL
    AAV-7   YTSNFEKQTG  V---DFAVDS  QGVYSEPRPI  GTRYLTRNL
    AAV-8   YTSNYYKSTS  V---DFAVNT  EGVYSEPRPI  GTRYLTRNL
   AAV-10   YTSNYYKSTN  V---DFAVNT  EGTYSEPRPI  GTRYLTRNL
    AAV-4   FTSNYGQQNS  L---LWAPDA  AGKYTEPRAI  GTRYLTHHL
   AAV-11   FTSNYGNQSS  M---LWAPDT  TGKYTEPRVI  GSRYLTNHL
    b-AAV   FTSNYGAQDS  L---LWAPDN  AGAYKEPRAI  GSRYLTNHL
    AAV-5   YTNNYNDPQF  V---DFAPDS  TGEYRTTRPI  GTRYLTRPL
      GPV   FTSNFSNRTS  I---MFAPNE  TGGYVEDRLI  GTRYLTQNL
      B19   VYPPHAAGHL  P---YVLYDP  TATDAKQHHR  HGYEKPEELW  TAKSRVHPL
      MVM   VSVEDNGNSY  MSVTKWLPTA  TGN-MQSVPL  ITRPVARNTY
      FPV   MSINVDNQF-  ----NYVPNN  IGA-MKIVYE  KSQLAPRKLY
      CPV   MSINVDNQF-  ----NYVPSN  IGG-MKIVYE  KSQLAPRKLY
Consensus   .t.n......  .......pd.  tg.y...r.i  gtryltr.l.  .........
```

Fig. 6

Bar chart showing Ratio (αvβ3 / A20) for viruses: wt, A2, RGD4C 453, RGD4C 453 A2, RGD4C 587, RGD4C 587 A2, RGD4C 453 & 587, RGD4C 453 & 587 A2.

Fig. 11

MUTATED STRUCTURAL PROTEIN OF A PARVOVIRUS

CROSS REFERENCE TO RELATED APPLICATIONS

This application is a Continuation of U.S. patent application Ser. No. 12/601,651, filed Mar. 5, 2010, which is the U.S. National Stage of International Application No. PCT/EP2008/004365, filed Jun. 2, 2008, which claims the benefit of U.S. Patent Application No. 60/932,410, filed May 31, 2007, each of which is hereby incorporated by reference.

The present invention is related to a structural protein of a parvovirus with an amino acid insertion at the insertion site I-453, a library comprising the protein, a multimeric structure comprising the protein, a nucleic acid encoding the protein, a vector, virus or cell comprising the nucleic acid, a process for the preparation of the protein, a medicament comprising the protein, nucleic acid or multimeric structure as well as methods and uses involving the protein, nucleic acid or multimeric structure.

Monoclonal antibody therapies have been one of the most successful therapy forms of new drug developments over the last couple of years in therapeutic fields such as oncology, autoimmune and inflammatory diseases. In monoclonal antibody therapies patients are injected with a specific monoclonal antibody that recognizes the antigen involved in the disease. Antibodies recognize their antigen with the variable domain of the antibody which is also referred to as the idiotype of the antibody.

However, monoclonal antibody therapies also have certain drawbacks. It can be observed that, if the concentration of a specific antibody with one particular idiotype is too high, the patient's immune system develops an antibody response against the idiotype of the therapeutic monoclonal antibody and thereby limits its efficacy. This kind of antibody that recognizes an antibody's idiotype is referred to as an anti-idiotypic antibody. In addition, antibodies to monoclonal therapeutic antibodies directed against other parts of the monoclonals often limit efficacy of a passive antibody therapy. Therefore, many of the monoclonal antibody drugs need to be used in combination with the traditional immunosuppression regiments, increasing the overall treatment costs. Furthermore, active suppression of the patient's immune system is detrimental especially; if an intact immune system is required to control the stage of disease such as for oncological indications.

As being a passive vaccination against the target antigen the monoclonal antibody has to be injected frequently depending on the half life of the antibody within the serum of the patient. Therefore, such treatments are expensive and inconvenient for the patients.

An alternative for such monoclonal antibody therapies already exists exemplified by a number of clinical developments using anti-idiotypic antibodies as drugs. Such anti-idiotypic antibody therapies are based on the fact (see above) that the patient's immune system can induce an antibody response against the idiotype of an antibody. If one uses a monoclonal antibody expressing a functional imitation of a target epitope (paratope or mimotope) as an idiotype, the patient's immune system will generate a polyclonal antibody response wherein a subset of these antibodies is able to cross-react with the target epitope in the patient. Such antibody expressing a paratope is referred to as an anti-idiotypic antibody (based on Jerne's network model of idiotypic relationships (Jerne, 1974, Jerne et al., 1982). Thus, selective immunization with an anti-idiotypic antibody can induce a specific immune response directed against the original antigen (Varela and Coutinho, 1991, Jefferis, 1993, Chatterjee et al., 1994).

Therefore, a vaccination with such an anti-idiotypic antibody actively induces a polyclonal antibody response. As a consequence such anti-idiotypic antibody vaccines have a number of advantages over a passive immunization by a standard monoclonal antibody. There is no antibody response towards the anti-idiotypic antibody that limits its efficacy as exactly this immune response is used as the therapeutic principle. Therefore, it is also not necessary to combine the antibody treatment with an immunosuppression regimen. And further, due to the fact that the anti-idiotypic treatment is an active immunization, the drug only has to be injected from time to time to boost the antibody response generated by the patient himself maintaining a continuous titer of specific antibodies. Additionally, anti-idiotypic antibodies induce a polyclonal antibody response against the target antigen that hampers the potential mechanism for resistance to the treatment of e.g. in tumor cells.

However, anti-idiotypic antibody therapies face major disadvantages. The titers of the induced polyclonal antibody response obtained by the vaccination with anti-idiotypic antibodies are often not high enough to establish a beneficial treatment. This is due to the lack of a strong antigen as a vaccine, since antibodies per definition are not very immunogenic. Furthermore, it is difficult to generate specific anti-idiotypic vaccines because of this lack of immunogenicity and technical difficulties to identify anti-idiotypic antibodies.

A series of publications describes that an antigen placed in the context of an ordered surface of a viral particle—here a papilloma virus particle—can induce a B cell response that even can abrogate B cell tolerance to such antigen by direct crosslinking the respective B-cell receptor. Bovine papilloma virus-like particles (VLPs) conjugated to an Aβ peptide through biotin were used to generate an immune response against the self antigen Aβ (Li et al., 2004). Further, this group used bovine papilloma virus-like particles having the murine chemokine receptor mCCR5 inserted into an immunodominant site of the viral L1 protein to immunize mice leading to sera with high anti-CCR5 antibody titers despite the fact that CCR5 is a self-antigen. Further, a macaque L1-CCR5 fusion protein was used to immunize pig tail macaques. 4 of the 5 test animals produced CCR5 specific antibodies. In a further approach TNF-α was joined to VLPs by way of a biotin-streptavidin interaction (Chackerian et al., 2001). These VLPs were successful in generating an auto-antibody response in mice, whereas these antibodies bound native TNF-α. (U.S. Pat. No. 6,719,978).

Therefore, papilloma VLPs have been shown to be a suitable backbone for the presentation of antigens to the immune system in order to generate strong B cell responses, probably because of their dense, ordered and closely packed array of vaccination epitopes. Due do their exceptionally strong B cell induction papilloma VLPs can be especially useful to overcome B cell tolerance to self antigens.

However, linkage of epitopes via biotin is a complicated process step that is difficult to perform under exactly controlled conditions as required by regulatory authorities for an approved drug. Further, the use of a bovine papilloma virus-backbone in humans may generate a dominant immune response against the viral backbone that the generated B-cell response against the inserted epitope is to weak to generate a sufficient priming of B-cells, which is especially important if tolerance has to be broken. Additionally, papilloma viruses are very difficult to manufacture in tissue culture and usually have to get isolated from warts. Therefore, for applications were viruses are necessary that encode a viral genome, papilloma viruses are unsuitable. One such application is the generation of viral libraries of capsid variants that can be used to screen a capsid mutant with certain properties like displaying an epitope matching to a monoclonal antibody of choice or an insert capable of binding to a cellular receptor of choice.

For Adeno-associated virus of type 2 (AAV-2) it was described in the past that the insertion of ligand peptides into structural proteins results in capsids that are able to display the ligand on the surface of the capsid and mediate transduction through the interaction of the ligand with its receptor thereby redirecting viral tropism by genetic capsid modifications (Girod et al., 1999, Grifman et al., 2001, Nicklin et al., 2001, Shi et al., 2001, Wu et al., 2000), which is referred to as hereinafter retargeting. In particular, it has been demonstrated that the insertion of an integrin binding Arg-Gly-Asp (RGD) motif at the insertion site I-587 of the AAV capsid proteins VP-1 enabled AAV particles to transduce cells via $\alpha_v\beta_1$ integrins (Aumailley et al., 1990, Girod et al., 1999). Successful targeting of gene vectors such as AAV-2 is important to increase the efficiency and safety of gene therapy, since it would allow to restrict the gene transfer into the desired tissue, minimize the risk associated with the transfer of potentially dangerous genes into other cell types and increase the concentration of the therapeutic gene product delivered to the ill tissue (Kay et al., 2001, Pfeifer and Verma, 2001). Although other potential insertion sites have been described for AAV-2, I-587 has by far been used most successfully and can be regarded as the best site for capsid modifications.

Further, AAV-2 libraries displaying random peptide inserts at the position I-587 have been reported that were successfully screened for targeting mutants (Perabo et al., 2003, Perabo, 2003, Waterkamp et al., 2006).

A further advantage of parvoviruses in this context is that due to the high structural conservation of parvoviruses knowledge obtained for e.g. AAV-2 can easily be transferred to other parvoviruses. Whenever repeated administration of the product is necessary the switch between different parvovirus backbones displaying the same peptide/epitope can circumvent (neutralizing) antibodies that have been raised in an earlier application.

However, an insertion within I-587—depending on its use—may have certain disadvantages. The insertion of ligand peptides into this site has been reported to ablate binding of heparin sulphate proteoglycan (HSPG), which is AAV-2's primary receptor, in some but not in all mutants (Perabo et al., 2006b). This phenomenon is likely due to the fact that an insertion interferes with at least two of the five positively charged amino acids of the recently identified HSPG binding motif (Kern et al., 2003, Opie et al., 2003), namely $R_{585}$ and $R_{588}$. Inserted peptides containing a net negative charge are prone to confer an HSPG nonbinding phenotype, while positive charges facilitate the interaction with HSPG (Perabo et al., 2006b). Conclusively, the interference of the HSPG binding site with the insertion site I-587 limits its universal applicability.

Generally speaking one can expect a certain interference of an inserted peptide/ligand with its surrounding amino acids of the capsid backbone. Such interference determines which kind of insert is acceptable for the viral capsid at a specific site. If another site is used for insertions, one can expect that the backbone context is different and different peptides can successfully be integrated. Therefore, the "ideal" peptide (e.g. for targeting the virus) may interfere at one site but may perfectly fit at another site.

In case of vaccination purposes HSPG binding might be necessary or at least useful for the capsids to enter predendritic cells, whose activation is needed to exert a $T_{H1}$-response. Consequently, the insertion of a B-cell epitope into I-587 may ablate HSPG binding and therefore would not trigger a $T_{H1}$-response. Additionally, viruses with an intact HSPG binding motif can still be efficiently purified using common heparin affinity chromatography.

Further, the combination of I-587 with a further insertion site would be ideal to increase the density of B-cell epitopes on the surface of the capsid or to display two different epitopes expressed from a single cap gene—in contrast to mosaic capsids generated by co-expressing more than one different cap gene, which is disadvantageous from a regulatory stand point.

Taken together these facts and considerations suggest that AAV and other parvoviruses are suitable backbones for vaccination purposes and/or retargeting approaches in the gene therapy context, but an additional insertion site with equal or improved properties is needed. Therefore, the underlying problem of the present invention is the identification of a further insertion site being an alternative or even superior to I-587, in which peptides can be inserted alone or in combination with insertions into e.g. I-587, which peptides are displayed on the surface of a capsid and which peptides are at least bound by a respective antibody and for the use of retargeting viral vectors can mediate transduction of target cells.

It has now been surprisingly found that the position after amino acid $G_{453}$ of AAV-2 is especially suitable for such insertions.

Accordingly, the major object of the present invention is a structural protein of AAV which comprises an amino acid insertion of one or more amino acids located directly adjacent to amino acid $G_{453}$ in the sequence of AAV-2 or to the corresponding amino acid of an AAV-2 variant or of any other parvovirus. Preferably, the amino acid insertion is directly C-terminal of amino acid $G_{453}$ in the sequence of AAV-2 or the corresponding amino acid of any other parvovirus.

Insertions near, but not exactly at this site have previously been suggested but were only of no or limited success. The insertion of the 14-amino-acid peptide L14 after amino acid $R_{447}$ (I-447) (Girod et al., 1999) led to intact capsids as the conformation-sensitive antibody A20 still reacted with it. Further, an L14-specific antibody specifically recognized the insert in an ELISA. The mutant capsid was further able to specifically bind to cells expressing the L14-specific integrin receptor. However, successful transduction did not occur for the insertion in I-447 in such cells—in contrast to a mutant capsid with the same insertion at I-587. These data show that in principle it is possible to insert peptides at I-447 as capsids are still formed and the inserted peptide is displayed on the surface of the protein, but at least for the L14 peptide such insertion does not lead to a successful transduction suggesting that I-447 is not an ideal candidate for insertions in general.

Also Wu et al. (Wu et al., 2000) report the insertion of a hemagglutinin (HA) peptide at the position I-447. Indeed, the mutated structural protein shows intermediate capsid formation and transduction (table 5, page 8643) but clearly this insertion site is inferior to I-587.

Further, Grifman et al. inserted a Myc epitope between $T_{448}$ and $N_{449}$ (referred to as by the authors 449Myc, see FIG. 3B; and herein I-448) (Grifman et al., 2001). The Myc epitope was accessible to an anti-Myc antibody and was therefore present on the surface of the capsid. Whereas successful retargeting was again reported for the insertion after $N_{587}$ (here the insertion of an NGR motif that mediates binding to CD13), no data on the retargeting using the I-449 site was presented indicating that retargeting was again not successful despite the fact that this site can be used to display inserts on the surface of a capsid.

In another study the insertion of an RGD4C peptide inserted after amino acid $R_{459}$ severely diminished transducing titers, whereas the insertion of the same peptide at positions $A_{139}$, $Q_{584}$ and $R_{588}$ were well tolerated (Shi and Bartlett, 2003).

the invention is not limited to AAV-2 but is also applicable to other parvoviruses as defined below. Additional parvovirus sequences can easily be aligned to the provided alignment (FIG. 2).

Therefore, insertions can be made at the herein defined insertion site I-453, being an insertion located directly N- or C-terminally, preferably C-terminally of one amino acid in the sequence of 5 amino acids N- or C-terminal of the corresponding amino acid to AAV-2's $G_{453}$, preferably 3, more preferably 1, especially directly N- or C-terminal, in particular C-terminal, of the corresponding amino acid to AAV-2's $G_{453}$. This means that the insertion site I-453 corresponds to the amino acids listed in Table 1.

TABLE 1

| | | I-453 | |
|---|---|---|---|
| Parvovirus | Amino acid no. | Amino acid seq. | SEQ ID NO: |
| AAV-2 | $G_{453}$ | N T P S G ▼ T T T Q S | SEQ ID NO: 1 |
| AAV-5 | $G_{446}$ | N N T G G ▼ V Q F N K | SEQ ID NO: 2 |
| AAV-1 | $G_{454}$ | Q N Q S G ▼ S A Q N K | SEQ ID NO: 3 |
| AAV-6 | $G_{454}$ | Q N Q S G ▼ S A Q N K | SEQ ID NO: 4 |
| AAV-8 | $G_{456}$ | Q T T G G ▼ T A N T Q | SEQ ID NO: 5 |
| AAV-10 | $G_{456}$ | Q S T G G ▼ T Q G T Q | SEQ ID NO: 6 |
| AAV-3b | $G_{454}$ | G T T S G ▼ T T N Q S | SEQ ID NO: 7 |
| AAV-7 | $G_{456}$ | S N P G G ▼ T A G N R | SEQ ID NO: 8 |
| AAV-4 | $G_{445}$ | S T T T G ▼ T T L N A | SEQ ID NO: 9 |
| AAV-11 | $G_{444}$ | S T T S G ▼ E T L N Q | SEQ ID NO: 10 |
| b-AAV | $G_{447}$ | S T T S G ▼ G T L N Q | SEQ ID NO: 11 |
| FPV | $G_{307}$ | F G D I G ▼ V Q Q D K | SEQ ID NO: 12 |
| CPV | $G_{271}$ | F G D I G ▼ V Q Q D K | SEQ ID NO: 13 |
| B19 | $G_{268}$ | P D T L G ▼ G D P K F | SEQ ID NO: 14 |
| GPV | $Y_{323}$ | V S A T Y ▼ T E G E A | SEQ ID NO: 15 |
| MVM | $T_{309}$ | A G T L T ▼ A Q G S R | SEQ ID NO: 16 |

▼ indicates the most preferred insertion site within I-453 for each structural protein listed.

Due to the near β-barrel structures that might get affected by insertions at I-453, one would not have expected that I-453 actually is a superior insertion site or at least an alternative insertion site compared to I-587.

Surprisingly, in the context of the present invention insertions directly C-terminally of $G_{453}$ of AAV-2 were found to be superior or at least a valid alternative to I-587.

As further detailed below peptide sequences that have been successfully inserted after $G_{453}$ and that were displayed on the capsid surface, were recognized by peptide-specific antibodies and—in case of a targeting mutant—mediated viral transduction. When aligning amino acid sequences of various parvoviruses it has surprisingly been found that $G_{453}$ of AAV-2 is conserved among all adeno-associated viruses included in the alignment and some more distantly related parvoviruses such as FPV, CPV and B19 (see FIG. 2). Previously published alignments of this region do not reveal this conserved amino acid (Grifman et al., 2001) FIG. 1, A and B, Loop III, (Girod et al., 1999) FIG. 1c). Accordingly, As the previously known insertion site I-587, I-453 lies within the C-terminal region of the CAP proteins that is present in VP-1, VP-2 and VP-3. Consequently, an insertion of a coding DNA sequence in frame into the cap gene at the corresponding site of I-453 leads to a respective amino acid insertion into VP-1, VP-2 and VP-3 (see FIG. 1).

The following definitions explain how the defined terms are to be interpreted in the context of the products, methods and uses of the present invention:

A "structural protein" means a protein that is part of the capsid of the virus. For parvoviruses the structural proteins are generally referred to as VP-1, VP-2 and/or VP-3, encoded by the cap gene. The amino acid sequences of structural proteins of parvoviruses are well known in the art. They are conserved within the parvoviruses. Amino acid positions provided herein that are not further specified refer to the AAV-2 sequence of the major coat protein VP-1 as published by Ruffing et al. (Ruffing et al., 1994); Genpept Accession No. 2906023).

A "mutated structural protein" means a structural protein that has at least one mutation in comparison to the respective structural protein of the wild-type virus.

A "parvovirus" means a member of the family of Parvoviridae containing several genera divided between two subfamilies Parvovirinae (Parvovirus, Erythrovirus, Dependovirus, Amdovirus and Bocavirus) and Densovirinae (Densovirus, Iteravirus, Pefudensovirus and Contravirus) (Fields: Virology, fourth edition 2001, Volume 2, chapters 69 (especially Table 1) and 70, Lippincott Williams Wilkins, Philadelphia. Preferred parvoviruses are members of the genus Parvovirus such as AAV-1, AAV-2, AAV-3b, AAV-4, AAV-5, AAV-6, AAV-7, AAV-8, AAV-9, AAV-10, AAV-11, AAV-12, bovine AAV (B-AAV), canine AAV (CAAV), canine parvovirus (CPV), mouse parvovirus, minute virus of mice (MVM), B19, H1, avian AAV (AAAV), feline panleukopenia virus (FPB) and goose parvovirus (GPV). More preferred parvoviruses are those that have a conserved G aligning to $G_{453}$ of AAV-2, which are AAV-1, AAV-2, AAV-3b, AAV-4, AAV-5, AAV-6, AAV-7, AAV-8, AAV-10, AAV-11, FPV, CPV, and B19 (see FIG. 2). Most preferred are AAV-2, AAV-1, and AAV-6.

An "epitope" is the part of a macromolecule that is recognized by the immune system, specifically by antibodies, B cells, or cytotoxic T cells. Although epitopes are usually thought to be derived from nonself proteins, sequences derived from the host that can be recognized are also classified as epitopes. Epitopes have a length of at least 4 amino acids, preferably 4 to 30 amino acids, more preferably 5 to 20 amino acids, especially 5 to 15 amino acids. Epitopes can be linear or three-dimensional formed typically by amino acids that are distant from each other in the primary protein structure but become closely related in a secondary and/or tertiary structure. Epitopes that are specifically recognized by B cells are referred to as B-cell epitopes.

A "tolerogen" is a self-antigen that is—in its natural environment—accessible to the humoral immune system. It may be either secreted or otherwise released from a living cell or associated to the outer surface of or integrated into the cellular membrane. Generally speaking tolerogens do—under normal circumstances in contrast to e.g. autoimmune diseases—not evoke a specific immune response due to tolerance against the antigen which results from a previous exposure to the same antigen. Tolerance can occur due to central tolerance or peripheral tolerance. Central tolerance refers to tolerogens which corresponding antigens have been exposed to T cells in the thymus leading to elimination of the specific T cells. Peripheral tolerance occurs when antigens/epitopes/mimotopes/paratopes are presented to T cells without appropriate additional stimuli, commonly provided by inflammation leading to anergy. Still, it has been observed that tolerogens can induce to some extent regulatory B-cell responses (Vogel et al., 2004).

In one preferred embodiment this invention relates to tolerogens due to peripheral tolerance, preferably tolerogens derived from tumor antigens/epitopes/mimo-topes/paratopes. Tolerogens encompassed by this invention include peptides, nucleic acids, carbohydrates, and lipids, preferably peptides.

Preferred tolerogens are antigens on the surface of a cell, especially tumor cells, e.g. receptors, especially growth factor receptors (preferably EGFR), tumor antigens (preferably Her2/NEU, Melan A, high molecular weight melanoma associated antigen (HMW MAA), CA125), viral receptors (CCR5), CD20, acetylcholine receptors, interleukin receptors (IL-13 receptor). Further preferred tolerogens can be blood proteins (preferably CETP), interleukins (preferably IL-6, IL-9, IL-13, IL-17), cytokines, TNF-family members (preferably TNF-α), immunoglobulins (preferably IgE), complement factors, misfolded proteins (preferably β-ayloid) and growth factors (preferably VEGF).

A "tolerogen-derived epitope" of a specific tolerogen in the context of the products, methods and uses of the present invention refers to a B-cell epitope that
i) is identical to a B-cell epitope of the tolerogen,
ii) a derivative (e.g. a mutant) of a B-cell epitope of the tolerogen that crossreacts with an antibody that binds the B-cell epitope of the tolerogen,
iii) a mimotope of a B-cell epitope of the tolerogen, and/or
iv) a paratope of a B-cell epitope of the tolerogen.

The length of a tolerogen-derived epitope is typically 4-30, preferably 5-20 and most preferably 5-15 amino acids.

The derivative of a B-cell epitope of a tolerogen may be generated by one or more amino acid substitutions, preferably one or more conservative amino acid substitutions, i.e. substitutions that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. Further, derivatives may be obtained by one or more single amino acid deletion(s) and/or insertion(s).

"Crossreaction" or "crossreact" of B-cell epitopes with a specific monoclonal antibody means according to this invention that the its affinity ($K_D$; see below) of the epitopes with the antibody are within two magnitudes, preferably within one magnitude when comparing the B-cell epitope to its derivative.

Tolerogen-derived epitopes within the multimeric structure comprising parvovirus mutated structural proteins according to this invention are identical, resemble or mimic antigen stretches of a tolerogen that are—in their natural environment—accessible to the immune system, e.g. epitopes of membrane protein located in the extracellular part, serum proteins, immunoglobulins, plaque proteins. Such antigen stretches are preferably located on the surface of such protein within the body of a mammal, preferably a human.

A "mimotope" is a non-linear structural epitope composed of several amino acids derived from different regions of the linear sequence of the structural protein located in close neighborhood due to the overall tertiary structure of the capsid that is specifically bound by an antibody, or a linear epitope mimicking a discontiuous epitope of the structural protein.

A "paratope" is the antigen binding site that is specifically bound by an antibody.

The mimotope or paratope in the context of the present invention might consist of (parts of) the inserted peptide sequence alone or might be composed of inserted peptide and parvovirus core particle amino acid residues.

An "insertion" of (an) amino acid(s) is generally speaking an insertion of at least one heterologous amino acid into the sequence of—for this invention—a parvovirus structural protein. 'Heterologous' in this context means heterologous as compared to the virus, from which the parvovirus structural protein is derived from. The inserted amino acids can simply be inserted between two given amino acids of the parvovirus structural protein. An insertion of amino acids can also go along with a deletion of given amino acids of the parvovirus sturctural protein at the site of insertion, leading to a complete substitution (e.g. 10 given amino acids are substituted by 10 or more inserted amino acids) or partial substitution (e.g. 10 given amino acids are substituted by 8 inserted amino acids) of amino acids of the parvovirus structural protein.

The term "binder" refers to a molecule that specifically binds to its respective binding partner. Commonly used binders are antibodies, especially monoclonal antibodies, antibody derivatives such as single chain antibodies or antibody fragments. In principle all classes of antibodies can be used, preferred are IgG antibodies. Fragments or multimers of antibodies can equally be used. Commonly used fragments are single chain antibodies, Fab- or $(Fab)_2$-fragments. Examples of other suitable binders are protein scaffolds such as anticalins or lipocalins (Nygren and Skerra, 2004), receptors or parts thereof (e.g. soluble T-cell receptors), ankyrine, microbodies or aptamers.

The term "specifically binds" means that two molecules A and B, preferably proteins, bind to each other thereby generating complex AB with an affinity ($K_D=k_{off}/k_{on}$) of at least $K_D=1\times10^{-5}$ mol/l, preferably $1\times10^{-7}$ mol/l, more preferably $1\times10^{-8}$ mol/l, especially $1\times10^{-9}$ mol/l.

"Heterologous" in the context of the present invention means a peptide sequence, e.g. an epitope that is not present on the parvovirus wild-type viral capsid and/or structural protein.

The term "antigen" in the context of the products, methods and uses of the present invention refers to any target antigen against which an immune reaction should be induced. Such target antigens are usually antigens that are susceptible to the humoral immune response. They are usually proteins that may be posttranslationally modified, as for example glycosylated proteins. Preferred antigens are serum proteins, proteins that can be found at least under certain conditions (e.g. in a disease state) in the blood (e.g. CETP, IL-6, IL-17, TNF-α), and membrane proteins, especially receptor proteins (e.g. CD20, acetylcholine receptors, IL13R, EGFR). Especially preferred antigens are IgE, tumor-antigens (e.g. Melan A, high molecular weight melanoma associated antigen (HMW MAA), CA125, IL13R, Her2/NEU, L1 cell adhesion molecule), VEGF, EGFR, $CD_2O$, CETP (cholesterol ester transfer protein), TNF-family members (e.g. TNF-α), interleukins (IL-9, IL-6, IL-13, IL-17), or misfolded proteins leading to a protein aggregation and, therefore, causing conformational diseases (for an overview see Uversky et al., 2006, e.g. β-amyloid). Excluded from the above definition of "antigen" are parvovirus antigens, i.e. antigens inherent the unmutated parvovirus itself, e.g. derived from B19 (Klenerman et al., 2002).

By inserting amino acids at I-453 the inserted amino acids are located on the surface of the capsid formed by the structural proteins. The display of the amino acids on the surface enables the insertion to exert their vaccination or targeting function.

Insertions at position I-453 did not interfere with particle formation of the capsid proteins. The structural protein of the present invention shows advantageous characteristics, in particular if the claimed structural proteins are to be used for vaccination purposes, as it is believed that ordered/virus-like particles are superior to exert a strong and insertion-specific immune response. However, as was shown for human papilloma virus-like particles also capsid subunits like capsomeres were able to be used for vaccination purposes. As a vaccination with a particle containing a genome is a gene therapy it is preferred to use inactivated (e.g. by gamma or UV-irradiation) genome-containing AAV particles, or virus-like particles of the respective parvovirus. Such virus-like particles (or in brief particles) are capsid-like structures that are composed of the structural proteins of the respective parvovirus, e.g. VP-1, VP-2 and/or VP-3, or parts thereof such as N- or C-terminal truncated structural proteins but do essentially not contain a viral genome. VP-2 alone has been shown to assemble into virus-like particles and can be expressed in various expression systems such as bacteria e.g. *E. coli*, yeasts, e.g. *Saccharomyces cerevisiae, hansenula polymorpha, Pichia pastoris*, in insect cells, e.g. the baculovirus expression system (SF9, SF+ or High Five cells), or in mammalian cells (such as CHO, HeLa, 293, BHK, or PerC6).

As far as the context of gene therapy is concerned, where viral vectors are constructed, the capability of forming particles such as capsids is an highly preferred feature, as intact particles are in general needed to package a viral genome carrying the transgene.

In a preferred embodiment the parvovirus is an adeno-associated virus, preferably selected from the group consisting of AAV-1, AAV-2, AAV-3b, AAV-4, AAV-5, AAV-6, AAV-7, AAV-8, AAV-9, AAV-10, AAV-11, AAV-12 and b-AAV, especially selected from the group consisting of AAV-1, AAV-2, AAV-5 and AAV-8. In a further preferred embodiment the parvovirus is selected from the group consisting of bovine AAV (b-AAV), canine AAV (CAAV), canine parvovirus (CPV), mouse parvovirus, minute virus of mice (MVM), B19, H1, avian AAV (AAAV), feline panleukopenia virus (FPV) and goose parvovirus (GPV), more preferably FPV, CPP, B19, GPV and MVM, especially FPV, CPV and B19.

The claimed structural protein contains an amino acid insertion that has a length of about 4 to about 30 amino acids, preferably about 5 to about 20, most preferably about 5 to about 15 amino acids. Typically, the size of a B-cell epitope is at least 5 amino acids (US 2004/0228798A1). Same is true for a number of known amino acid sequences suitable as targeting sequences. Larger inserts are likely to interfere with each other. It is also encompassed by this invention that one insert comprises more than one functional amino acid sequence (e.g. epitopes and/or targeting sequences) in a row. For example the insert can comprise 2, 3, 4, 5 or 6 identical inserts in a row or 2, 3, 4, 5 or 6 different functional amino acid sequences such as different epitopes.

The nature of the amino acid insertion is preferably an epitope, especially a B-cell epitope. Epitopes are generally preferred if the structural proteins are modified to be suitable for vaccination purposes. The epitopes can be known B-cell epitopes that have been identified as linear epitopes, paratopes or sequence that form mimotopes. Therefore, B-cell epitopes can be both linear and structural. However, it is especially preferred to use linear epitopes that are no mimotopes.

Further, the epitopes can be sequences that have been identified by phage display or by AAV display, where a library of amino acid sequences is displayed on the surface of phages or AAV and such phages/AAVs are identified that specifically bind to a specific binder, especially an antibody of choice. The inserted amino acid sequence can be sequenced and transferred into I-453. In a preferred embodiment the amino acid sequence is directly identified from an AAV-library, where the library of amino acid sequences had been inserted into I-453, for example in analogy to the AAV-2 libraries described in (Perabo et al., 2003, Lieber, 2003, Muller et al., 2003) (WO 03/054197). In this context the advantage is used that the amino acid insert is identified in the same surface context as it is used for vaccination later on. Therefore, the conformation is not changed compared to settings where an epitope is transferred from an original context (e.g. from an antigen or from a phage) to the site I-453.

In a preferred embodiment the B-cell epitope is heterologous to the parvovirus.

In an especially preferred embodiment the inserted B-cell epitope is a tolerogen-derived epitope. As described above it is especially difficult to break tolerance and structural proteins according to this invention are especially suitable for this purpose. Preferred tolerogen-derived epitopes are derived from IgE, CETP, CCR5, HER2/Neu, TNF-α, IL-17, IL-6 or β-amyloid, preferably human IgE and human β-amyloid, exemplified by the following preferred epitopes:

IgE Epitopes:

```
                                       (SEQ ID NO: 50)
VNLTWSRASG ("Kricek")

(SEQ ID NO: 55)
EFCINHRGYWVCGD ("Rudolf")

(SEQ ID NO: 85)
EDGQVMDVDLS ("Flex")

(SEQ ID NO: 86)
EKQRNGTLT ("Bind-2")

(SEQ ID NO: 87)
TYQCRVTHPHLPRALMR ("3DEpi1")

(SEQ ID NO: 88)
RHSTTQPRKTKGSG ("3DEpi2")

(SEQ ID NO: 89)
DSNPRGVSAYLSR (3DEpi3)

(SEQ ID NO: 90)
TITCLVVDLAPSK ("3DEpi4")

(SEQ ID NO: 91)
KTKGSGFFVF ("C4E")

(SEQ ID NO: 92)
THPHLPRALMRS ("Wang-CS")

(SEQ ID NO: 93)
GETYQCRVTHPHLPRALMRSTTK ("Wang")

(SEQ ID NO: 94)
LPRALMRS ("C21")

(SEQ ID NO. 95)
INHRGYWV ("C4M")
```

CETP Epitopes:

```
                                       (SEQ ID NO: 60)
CDAGSVRTNAPD (SEQ ID NO: 96)
AKAVSNLTESRSESLQS ("CETP TP10")

(SEQ ID NO: 97)
SLTGDEFKKVLET ("CETP TP11")

(SEQ ID NO: 98)
REAVAYRFEED ("CETP TP12")

(SEQ ID NO: 99)
INPEIITLDG ("CETP TP13")

(SEQ ID NO: 100)
DISVTGAPVITATYL ("CETP TP18")

(SEQ ID NO: 101)
DISVTGAPVITA ("CETP TP20A")

(SEQ ID NO: 102)
PKTVSNLTESSSESVQS ("hTP10")

(SEQ ID NO: 103)
SLMGDEFKAVLET ("hTP11")

(SEQ ID NO: 104)
QHSVAYTFEED ("hTP12")

(SEQ ID NO: 105)
INPEIITRDG ("hTP13")

(SEQ ID NO: 106)
DISLTGDPVITASYL ("hTP18")

(SEQ ID NO: 107)
DISLTGDPVITA ("hTP20")

(SEQ ID NO: 108)
DQSIDFEIDSA ("hRitsch-1")

(SEQ ID NO: 109)
KNVSEDLPLPTFSPTLLGDS ("hRitsch-2")

(SEQ ID NO: 110)
KNVSEDLPLPT ("hRitsch-3")

(SEQ ID NO: 111)
CDSGRVRTDAPD ("hCETP-intern")

(SEQ ID NO: 112)
FPEHLLVDFLQSLS ("hCETP C-Term")
```

β-Amyloid Epitope:

```
DAEFRHDSG           (SEQ ID NO: 65)
```

CCR5 Epitopes:

```
                                       (SEQ ID NO: 113)
HYAAAQWDFGNTMCQL (Chackerian, 1999)

(SEQ ID NO: 114)
YAAQWDFGNTMCQ (Barassi et al., 2005)

(SEQ ID NO: 115)
RSQKEGLHYT (Misumi et al., 2006)
```

TNF-α Epitopes:

```
                                       (SEQ ID NO: 116)
SSRTPSDKPVAHVVANPQAE ("TNF-α V1")

(SEQ ID NO: 117)
SRTPSDKPVAHVVANP ("TNF-α V2")

(SEQ ID NO: 118)
SSRTPSDKP ("TNF-α V3")
```

IL-17 Epitopes:

```
NADGNVDYHMNSVP ("IL-17 V1")     (SEQ ID NO: 119)

DGNVDYHMNSV ("IL-17 V2")        (SEQ ID NO: 120)
```

IL-6 Epitopes:

```
                                       (SEQ ID NO: 121)
RSFKEFLQSSLRALRQ ("IL-6 V1")

(SEQ ID NO: 122)
FKEFLQSSLRA ("IL-6 V2")
```

HER2/Neu Epitope:

QMWAPQWGPD (Riemer et al. 2007). (SEQ ID NO: 123)

As described earlier it is one embodiment to modify structural proteins in order to retarget the parvovirus to a different cell or tissue. Therefore, in another preferred embodiment of the present invention the amino acid insertion is a sequence that brings about an increase in the transducing activity of the mutated parvovirus. Increase in the transducing activity according to this invention means preferably that the ratio of genomic particles divided by transducing particles (GenP/tP) as determined in Example 6.1 is lowered for a cell line of choice compared to the respective unmutated parvovirus. An increase in this context preferably refers to a decrease of GenP/tP of at least about 25%, more preferably at least about 100%, still more preferably at least about 300%, most preferably at least about 1000%.

Such increase in the transducing activity is usually accomplished by an amino acid insertion that mediates binding of the structural protein in the form of a particle to a cell membrane receptor. These inserted targeting sequences can be known ligands or parts thereof for a given receptor. Further, the targeting sequences can be sequences that have been identified by phage display or by AAV display, where a library of amino acid sequences is displayed on the surface of phages or AAV and such phages/AAVs are identified that specifically bind to a receptor of choice. The inserted amino acid sequence can be sequenced and transferred into I-453. In a preferred embodiment the amino acid sequence is directly identified from an AAV-library, where the library of amino acid sequences had been inserted into I-453, for example in analogy to the AAV-2 libraries described in (Perabo et al., 2003, Lieber, 2003, Muller et al., 2003), (WO 03/054197). In this context the advantage is used that the amino acid insert is identified in the same surface context as it is used later on. Therefore, the conformation is not changed compared to settings where a targeting sequence is transferred from an original context (e.g. as part of ligand or from a phage) to the site I-453.

In an especially preferred embodiment the inserted targeting sequence does contain an RGD motif, especially it is the sequence ACDCRGDCFCA (SEQ ID NO: 84), herein referred to as RGD-4C peptide. The RGD motif in general and especially the RGD-4C peptide mediate the binding to the integrins, especially $\alpha_v\beta_3$ and $\alpha_v\beta_5$. Consequently, these structural proteins can be used to target cells expressing these integrins.

In a further preferred embodiment the insertion brings about an alteration in a chromatographic property of the structural protein. It is preferred to insert a known tag that can be used for binding the structural protein or a particle composed of the structural protein to a ligand. Such tags are well known in the art. Examples are given in Table 2.

TABLE 2

| Tags and corresponding ligands | |
|---|---|
| Tag | Ligand |
| HIS | Nickel |
| GST | Glutathione |
| Protein A | IgG |
| Biotin or Strep | Streptavidin |

TABLE 2-continued

| Tags and corresponding ligands | |
|---|---|
| Tag | Ligand |
| Calmodulin-binding peptide | Calmodulin |
| Fc-Peptide of IgG | Protein A |
| Flag | FLAG- or 3xFLAG peptide |
| HA (hemagglutinin) | HA peptide |

Depending on their use the particles of this invention may have to be purified to high purity. Otherwise unmodified structural proteins can be modified by insertion to alter their chromatographic properties as it has been described in WO 01/05991. In case of AAV-2 the HSPG binding capabilities due to the loop structure around I-587 remain unchanged if a tag is inserted into I-453. Furthermore, modified structural proteins that comprise for example a targeting insert and/or an epitope at a site different to I-453 can be further modified to display a tag that enables simple and scalable purification to high purity.

The insertion according to this invention may have an N- and/or C-terminal linker. A linker according to this invention is a further stretch of at least one amino acid N- and/or C-terminal of the inserted epitope, targeting sequence or tag, preferably of 2-12 amino acids. Preferred amino acids for the linker are amino acids selected from the group consisting of Ala, Gly, Ser, Pro, and Cys, especially 3 Ala upstream and 2 downstream of the B-cell epitope, 5 Ala upstream and 5 downstream of the B-cell epitope, or 3-5 Gly upstream and 3-5 Gly downstream of the B-cell epitope.

In a further preferred embodiment the insertion comprises linker sequences which enable a circularization of the inserted peptide sequences in order to better display the insertion. Accordingly spacer sequences are selected to form Zinc-fingers (Zn-finger), well known in the art. Preferred Zn-finger motifs are CXXC or $C_2H_2$. Preferred Zn-finger motifs are $C_2H_2$, $C_4$, and $C_2HC$ including but not limited to motifs $CX_2CX_nC_2$, $CX_2CX_{10-30}CX_2C$, $CX_5HX_{10-30}CX_2C$, $CX_2CX_{10-30}CX_4H$ (Laity et al., 2001, Gamsjaeger et al., 2007).

An example of a preferred Zn-finger linker is:

$$X_{(3-5)} CXXCX_{(0-5)} (NNK)_n X_{(0-5)} CXXCX_{(3-5)}$$

(X=Gly or Ala, C=Cys; with each N being any nucleotide and K standing for G or T). Thus the random NNK sequence protrudes from the capsid surface.

In an especially preferred embodiment the linker comprises at least one Cys N-terminal and at least one Cys C-terminal of the insertion. Such cysteins are capable of forming a disulfide bond to generate a loop that stabilizes the insertion and thereby facilitates its binding to its antibody, receptor or ligand.

It is a further embodiment of the present invention that the parvovirus structural protein comprises one or more further mutation(s) at a site different from I-453. This/These further mutation(s) is/are independently selected from the group consisting of a point mutation, an internal deletion, a terminal deletion, an insertion and a substitution. In general, the purpose of such further mutation may be selected from the same group of purposes as explained above for the insertion into I-453, namely to generate a vaccine, to target a vector to a different cell/tissue and/or change the chromatographic properties in order to purify the particles to high purity. Accordingly, an additional insertion may again be an epitope, preferably a B-cell epitope or CTL epitope (as further specified below), especially a tolerogen-derived epitope, a targeting sequence that enhances the transduction activity, preferably a ligand to a receptor of choice, or a tag. For further characterization of these further insertions reference is made to the above sections that described the features for the I-453 insertion that equally apply for a second insertion.

This further peptide can be identical to the insertion in I-453. This is preferred if it is key to have a large number of identical peptides being optimally presented on the surface of a particle, especially in cases where direct B-cell receptor (BCR) crosslinking is required for T-cell independent priming of B-cells and breaking of tolerance against self-antigens. A higher density of B-cell epitopes increases the likelihood of optimal peptide-specific BCR crosslinking which requires a defined distance between BCRs (e.g. about 5-10 nm), and therefore, respective B-cell epitopes being presented on a parvovirus capsid. Furthermore, as shown in this invention (FIG. 5), modifications of parvovirus capsids at two or more different sites at a time can lead to a conformational cross-talk within the capsid structure leading to an improved presentation of the inserted peptide sequence. Moreover, a larger number of inserted B-cell epitopes decreases the probability for undesired immune reactions against the parvovirus backbone due to i) masking of natural parvovirus B-cell epi-/mimotopes and/or ii) slight structural capsid changes rendering these natural B-cell epi-/mimotopes less immunogenic.

Consequently, in this case it is especially preferred that the inserted peptide is a B-cell epitope, even more preferred a tolerogen-derived epitope. Parvovirus structural proteins displaying a high number of epitopes on the surface of a virus-like particle/capsid can efficiently be used to generate T-cell independent B-cell responses and even break tolerance. As shown in examples 5.4 and 6.2, identical epitopes, respectively B-cell epitopes can be inserted in two different insertion sites, here I-453 and I-587, and are accessible to soluble ligand, in this case $\alpha_v\beta_3$, or β-amyloid, respectively. Therefore, it is an especially preferred embodiment of this invention that an identical peptide is inserted at I-453 and I-587 and that this peptide is a B-cell epitope, most preferred a tolerogen-derived epitope. Another preferred double insertion variant is a variant with insertions at I-453 and I-261.

However, the further peptide can be a different one compared to the peptide inserted into I-453.

Therefore, it is a further embodiment of the present invention that an insertion at position I-453 is combined with at least one further amino acid insertion at one or more additional site. Additional suitable insertion sites identified by using AAV-2 are well known in the art and are exemplarily listed in Table 3. However, it should be understood that the further amino acid insertion at one or more additional site(s) is/are not limited to those listed in the following.

TABLE 3

Further insertion sites

| Insertion site | corresp. amino acid/ sequence of AAV-2 | | SEQ ID NO: | References |
|---|---|---|---|---|
| I-1 | $M_1$ | $M_1$ AADGY | SEQ ID NO: 17 | (Wu et al., 2000) |
| I-34 | $P_{34}$ | PPPK$P_{34}$ AERHK | SEQ ID NO: 18 | (Wu et al., 2000) |
| I-138 | $T_{138}$ | EPVK$T_{138}$ APGKK | SEQ ID NO: 19 | (Wu et al., 2000, Warrington et al., 2004, Lux et al., 2005) |
| I-139 | $A_{139}$ | PVKT$A_{139}$ PGKKR | SEQ ID NO: 20 | (Shi et al., 2001, Shi and Bartlett, 2003, Arnold et al., 2006) |
| I-161 | $K_{161}$ | SGTG$K_{161}$ AGQQP | SEQ ID NO: 21 | (Shi et al., 2001, Arnold et al., 2006) |
| I-261 | $S_{261}$ | YKQI$S_{261}$ SQSGA | SEQ ID NO: 22 | (Girod et al., 1999) |
| I-266 | $A_{266}$ | SQSG$A_{266}$ SNDNH | SEQ ID NO: 23 | (Wu et al., 2000) |
| I-381 | $N_{381}$ | YLTL$N_{381}$ NGSQA | SEQ ID NO: 24 | (Girod et al., 1999) |
| I-447 | $R_{447}$ | YYLS$R_{447}$ TNTPS | SEQ ID NO: 25 | (Girod et al., 1999, Wu et al., 2000) |
| I-448 | $T_{448}$ | YLSR$T_{446}$ NTPSG | SEQ ID NO: 26 | (Grifman et al., 2001) |
| I-459 | $R_{459}$ | TTQS$R_{459}$ LQFSQ | SEQ ID NO: 27 | (Shi et al., 2001, Arnold et al., 2006) |
| I-471 | $R_{471}$ | ASDI$R_{471}$ DQSRN | SEQ ID NO: 28 | (Asokan and Samulski, 2006, Moskalenko et al., 2000) |
| I-520 | $G_{520}$ | LVNP$G_{520}$ PAMAS | SEQ ID NO: 29 | (Shi et al., 2006) |
| I-534 | $F_{534}$ | EEKF$F_{534}$ PQSGV | SEQ ID NO: 30 | (Girod et al., 1999) |
| I-570 | $\underline{P}_{570}$ | RTTN$\underline{P}_{570}$ VA$\underline{T}$EQ | SEQ ID NO: 124 | own data |
| I-573 | $T_{573}$ | NPVA$T_{573}$ EQYGS | SEQ ID NO: 31 | (Girod et al., 1999) |

TABLE 3 -continued Further insertion sites

| Insertion site | corresp. amino acid/ sequence of AAV-2 | SEQ ID NO: | References |
|---|---|---|---|
| I-584 | $Q_{584}$ STNLQ$_{584}$ RGNRQ | SEQ ID NO: 32 | (Shi et al., 2001, Shi and Bartlett, 2003, Shi et al., 2006) |
| I-587 | $N_{587}$ LQRGN$_{587}$ RQAAT | SEQ ID NO: 33 | (Girod et al., 1999, Shi et al., 2001, Grifman et al., 2001, Ried et al., 2002, Nicklin et al., 2001, Work et al., 2004, White et al., 2004, Arnold et al., 2006, Maheshri et al., 2006, Work et al., 2006) |
| I-588 | $R_{588}$ QRGNR$_{588}$ QAATA | SEQ ID NO: 34 | (Shi and Bartlett, 2003, Muller et al., 2003, Waterkamp et al., 2006) |
| I-591 | $A_{591}$ NRQAA$_{591}$ TADVN | SEQ ID NO: 35 | (Wu et al., 2000) |
| I-657 | $P_{657}$ VPANP$_{657}$ STTFS | SEQ ID NO: 36 | |
| I-664 | $A_{664}$ TFSAA$_{664}$ KFASF | SEQ ID NO: 37 | (Wu et al., 2000) |
| I-713 | $T_{713}$ NVDFT$_{713}$ VDTNG | SEQ ID NO: 38 | |
| I-716 | $T_{716}$ FTVDT$_{716}$ NGVYS | SEQ ID NO: 39 | (Maheshri et al., 2006) |

I-570 is especially suitable as an insertion site that goes along with a deletion of given amino acids of the parvovirus structural protein at the site of insertion, leading to a complete substitution. In this case the amino acids RTTN PVATEQ can be substituted by a targeting peptide or epi- or mimotope.

Insertions have successfully also been made into AAV-serotypes other than AAV-2 (Table 4).

TABLE 4

Insertions into AAV-serotypes other than AAV2

| AAV serotype | Sequence | SEQ ID NO: | Ins. site/amino acid relative to AAV2 | | References |
|---|---|---|---|---|---|
| AAV1 | FQSSS$_{588}$ TDPAT | SEQ ID NO: 125 | I-587 | $N_{587}$ | own data |
| AAV1 | SSSTD$_{590}$ PATGD | SEQ ID NO: 40 | I-589 | $Q_{589}$ | (Arnold et al., 2006, Stachler and Bartlett, 2006) |
| AAV3 | NNLQS$_{586}$-SNTAP | SEQ ID NO: 41 | I-585 | $R_{585}$ | (Arnold et al., 2006) |
| AAV4 | GGDQS$_{584}$-NSNLP | SEQ ID NO: 42 | I-585 | | (Arnold et al., 2006) |
| AAV5 | TNNQS$_{575}$-STTAP | SEQ ID NO: 43 | I-585 | | (Arnold et al., 2006) |

The used nomenclature I-### within this invention refers to the insertion site with ### naming the amino acid number relative to the VP-1 protein of AAV2, however meaning that the insertion may be located directly N- or C-terminal, preferably C-terminal of one amino acid in the sequence of 5 amino acids N- or C-terminal of the given amino acid, preferably 3, more preferably 2, especially 1 amino acid(s) N- or C-terminal of the given amino acid. For parvoviruses other than AAV2 the corresponding further insertion sites can be identified by performing an amino acid alignment or by comparison of the capsid structures, if available. Such alignment has been performed for the parvoviruses AAV1, AAV6, AAV2, AAV3b, AAV7, AAV8, AAV10, AAV4, AAV11, b-AAV, AAV5, GPV, B19, MVM, FPV and CPV (see FIG. 3).

Most of the work on targeting parvoviruses was done using AAV2. However, due to the high conservation of at least large stretches and the large member of closely related family members it is easy to identify corresponding sites of AAV2 within other parvoviruses, e.g. by using alignments as shown in FIG. 3.

An insertion into the corresponding position of the coding nucleic acid of one of these sites of the cap gene leads to an insertion into VP-1, VP-2 and/or VP-3, as the cap proteins are encoded by overlapping reading frames of the same gene with staggered start codons. Therefore for AAV2, according to this nomenclature insertions between amino acids 1 and 138 are only inserted into VP-1, insertions between 138 and 203 are inserted into VP-1 and VP-2, and insertions between 203 and the C-terminus are inserted into VP-1, VP-2 and VP-3, which is of course also the case for the insertion site I-453. A schematic organization of the cap gene of AAV2 is provided in FIG. 1. Therefore, the present invention encompasses structural genes of parvoviruses with corresponding insertions in the VP-1, VP-2 and/or VP-3 proteins.

More preferred additional insertion sites are I-138, I-261, I-570, I-575, I-584, I-587, I-588 and I-590.

The most preferred further insertion site is I-587, as various insertions have been made in the amino acid stretch around $N_{587}$ (LQRGN$_{587}$ RQAAT) of AAV2. Within this stretch insertions of various peptides were made C-terminal of amino acids $Q_{584}$, $N_{587}$, $R_{588}$ and $A_{591}$ in AAV2 (Table 3) and C-terminal of amino acids of other AAV-serotypes corresponding to $R_{585}$ and $O_{589}$ of AAV2 (Table 4).

Amino acid 138 is the N-terminus of VP-2. Preferred embodiments are VP-2 structural proteins with an additional N-terminal fusion to one of the amino acids within the stretch $T_{138}$ APGKKR. In order to achieve an N-terminal fusion to VP-2 only, one could use an expression construct with the coding sequence for VP-2 with the respective insert comprising its own start codon. This construct would be co-transfected with a vector construct where the start codon for VP-2 was eliminated.

Further, preferably the further inserted nucleic acid sequence may be inserted at any site corresponding to the first amino-terminal amino acids 1 to 50 of VP-1.

Within this invention an AAV2 structural protein was generated that contained an insertion of an β-amyloid tolerogen-derived epitope both at I-453 and I-587. Surprisingly, it was shown that compared to a structural protein containing the same insert only at I-587 the respective particles were much better recognized by a β-amyloid-specific antibody (see example 5).

Additionally encompassed by this invention are point mutations such as substitutions or internal deletions, where at least one amino acid is deleted or replaced by a different amino acid that decreases binding of the structural protein and/or respective particles composed of the structural proteins to primary or secondary cellular receptors for the respective virus. This detargeting of the virus from its natural host cell is important especially if systemic versus local or loco-regional administration of the particles is intended, as uptake of the particles by the natural host cells limits the effective dose of the particles. In case of AAV2 and AAV6 HSPG is reported to be the primary receptor for viral uptake in a large number of cells, especially liver cells. For AAV2 HSPG-binding activity is dependent on a group of 5 basic amino acids, $R_{484}$, $R_{487}$, $R_{585}$, $R_{588}$ and $K_{532}$ (Kern et al., 2003). Recently it was reported that the lysine-to-glutamate amino acid substitution $K_{531}E$ leads to the suppression of AAV6's ability to bind heparin or HSPG ((Wu et al., 2006)).

Accordingly, preferred point mutations are those that reduce the transducing activity of the particle for a given target cell mediated by the natural receptor by at least 50%, preferably at least 80%, especially at least 95%, in case of HSPG as primary receptor the binding of the particles to HSPG. Transducing ability can be determined as described in example 6.1 as the GenP/tP ratio (see also above).

Consequently, further mutations preferred for HSPG-binding particles are those mutations that deplete or replace a basic amino acid such as R, K or H, preferably R or K which is involved in HSPG binding of the respective virus, by a non-basic amino acid such as A, D, G, Q, S and T, preferably A or an amino acid that is present at the corresponding position of a different but highly conserved AAV serotype lacking such basic amino acid at this position. Consequently preferred amino acid substitutions are $R_{484}A$, $R_{487}A$, $R_{487}G$, $K_{532}A$, $K_{532}D$, $R_{585}A$, $R_{585}S$, $R_{585}Q$, $R_{585}A$ or $R_{588}T$, especially $R_{585}A$ and/or $R_{588}A$ for AAV2, and $K_{531}A$ or $K_{531}E$ for AAV6.

Figure 7:
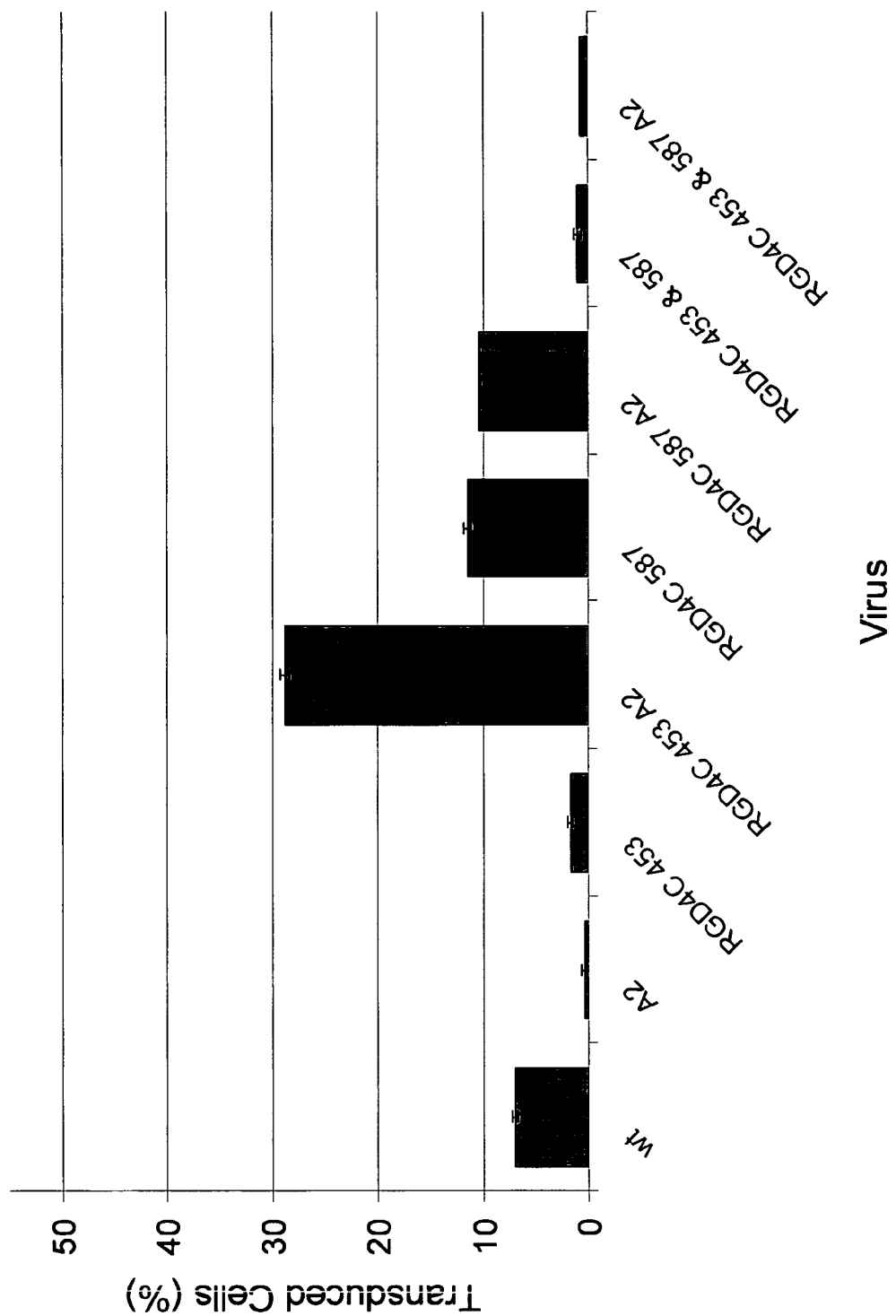

One especially preferred embodiment of the invention are such structural protein mutants of AAV2 that additionally contain the two point mutations $R_{585}A$ and $R_{588}A$ as these two point mutations are sufficient to ablate HSPG binding activity to a large extent. These point mutations enable an efficient detargeting from HSPG-expressing cells which—for targeting purposes—increases specificity of the respective mutant virus for its new target cell. Furthermore, these point mutations seem to lead to a structural change rendering the RGD4C 453 A2 capsid mutant transducing (FIG. 7).

It is also an embodiment of the present invention that the parvovirus mutated structural protein comprises at least one further mutation that reduces the ability to induce a B-cell response against a parvovirus-specific epitope and/or mimotope, thereby reducing the natural antigenicity of the respective particle. Administration of particles, either as vaccines or as vectors, is usually hampered by existing antibodies directed against certain epitopes of the particle/capsid. In case of AAV2, the majority of the human population has an AAV2 positive serum status. In case of non-human parvoviruses the patient will generate a strong humoral immune response against the particle backbone that may neutralize the vector or may dominate an intended immune response against an inserted epitope. Point mutations as well as insertions have been described to modify the natural antigenicity of particles to evade a preexisting immune response (e.g. (Huttner et al., 2003); WO 01/05990). Perabo et al. were able to identify point mutations that increased AAV2's immune-escaping ability by up to 5.5-fold higher N50 values (amount of human serum needed to halve the number of transduced cells) in comparison to AAV2 with wild-type structural proteins (Perabo et al., 2006a), namely a point mutation at positions $R_{459}$ and $N_{551}$. Therefore, a further preferred embodiment is a mutated structural protein that further comprises a point mutation that reduces the ability to induce a B-cell response against an AAV-specific epitope and/or mimotope, preferably for AAV2 a point mutation at position $R_{459}$ and/or $N_{551}$.

A further mutation can be also used to compose more complex mimotopes or to enhancing the correct display of an inserted amino acid sequence. Such further mutations can either be identified by using structure prediction software or by inserting random point mutations into the respective cap gene e.g. by error prone PCR and then selecting for matured display of the inserted amino acid sequence.

In a further preferred embodiment the further mutation might be adequate to introduce at least one cytotoxic T-cell epitope (CTL epitope). For both infectious diseases and cancer it is most useful to combine both humoral and cellular immune responses to fight these diseases. The multimeric structures according to the invention are in principle capable of pseudo-infecting cells. Accordingly these structures—like viruses—are able to enter cells, are processed to peptides, the peptides are loaded onto MHC class I and II molecules and finally presented to CD8- or CD4-positive T cells. The T-cells become stimulated after specific recognition of such processed peptide presented by MHC class I or II molecules. As a consequence of such stimulation CD8 cells may differentiate into cytotoxic T cells and then cause a cellular immune response. CD4 cells may develop into T helper cells which stimulate B cells to provide a humoral immune response or CD8-positive T cells to provide a cytotoxic immune response, which may themselves induce lysis of infected cells and other cells carrying and presenting the same peptide. Suitable CTL epitopes are known in the art for various cancer antigens or viral antigens, or they can be predicted from given antigen sequences using for example the peptide prediction program by Parker (Parker et al., 1994). Proposed CTL epitopes can be validated according to the methods as exemplified for HPV-epitopes in U.S. Pat. No. 6,838,084, examples 2-8 (herein incorporated by reference). As processing of CTL epitopes occurs within the cell it is not necessary that such CTL epitopes are located on the surface or are present in a specific combination A further embodiment of the present invention is a library of structural proteins, wherein the library comprises a set of different parvoviral structural proteins inserted at I-453 as described above. AAV2 libraries have been previously described for the insertion site I-587 (Perabo et al., 2003, Lieber, 2003, Muller et al., 2003). The same technology can equally be applied to the newly identified insertion site I-453. The advantages described for the insertion site I-453 for insertions versus I-587 and other sites in general equally apply to a library generated for the insertion site I-453. E.g. using I-453 based libraries may result in the selection of other peptides (as for example with I-587 based libraries) since neighboring residues may have an influence on the exposure and functionality of the peptides inserted into the structural protein. In addition, the sites (I-587 and I-453) are located on different loops of the AAV capsid. Thus a different mechanism of cell interaction can be assumed. Furthermore, AAV particles derived from I-453 libraries can be purified with heparin affinity chromatography, as the heparin binding site overlapping with I-587 is still intact. Further, a library with inserted sets of amino acid insertions in both I-453 and a further insertion site can be used to enhance the multiplicity of the library and select structural proteins with higher binding affinities.

In a preferred embodiment genotype and phenotype of virion particles of the library are coupled. This means that the genomic mutant of the virion is identical to the phenotypic mutant of the same virion or, in other words, that each structurally modified virus codes for its structural protein mutant.

In contrast to a bacterial transformation, where only one bacteriophage is taken up by one bacterial cell, using transfection methods for eukaryotic cells many DNA copies (up to $1\times10^{6}$) can be taken up per cell (Dean et al., 2005). Therefore, in the case of an AAV library one cell can replicate thousands of AAV genomes at the same time where each may express a different mutated structural protein with a different peptide sequence inserted into VP1, VP2, and/or VP3 of AAV. At least some of these structural proteins can assemble a complete viral capsid (consisting of 5 VP1, 5 VP2 and 50 VP3 proteins) encapsidating essentially only one of the thousands of AAV genomes present in the cell. In case of a geno-/phenotypically coupled library at least 10%, preferably more than 25%, especially more than 50% of the resulting AAV particles have an encapsulated genome which codes for at least 25%, preferably more than 50%, especially more than 80% of the 60 VP proteins of which its capsid is composed. As a consequence, if an uncoupled library was used for a first screening against a target antibody or target receptor, the chance that screened particles contained the genome coding for this specific amino acid sequence might be very low.

In general, geno-/phenotypically coupled virion particles/libraries are obtained when introducing essentially one single copy of the virus genome into each virion production cell entering the cell nucleus. This cell will only produce capsid protein variants encoded of exactly the introduced genome which is replicated and afterwards packaged into the mutant virion particle. Different experimental settings can ensure this:

To obtain a geno-/phenotypically coupled library of parvovirus virions a library of parvovirus virions is produced by transfecting a plasmid library into production cells under suitable conditions whereas a low copy number of viral genomes equal to or less than 100 genomes per cell is used, preferably equal to or less than 10 genomes, more preferably equal to or less than one genome per cell, resulting in geno-/phenotypically coupled virions/library. The overall transfection efficacy will be finally decisive for the ideal number of virus genomes per cell to be transfected.

The required amount of virus plasmid can be quantified, if e.g. autonomous replicating plasmids with similar size as the virus genome encoding a reporter gene such as GFP are used as a model system. Autonomous replicating plasmids are e.g. systems comprising SV40 origin of replication and large T antigen or the EBV (ebstein barr virus) P1 origin and EBNA. Increasing amounts of the self-replicating reporter gene plasmid are cotransfected with carrier DNA such as empty plasmid DNA (e.g. pUC derivates) keeping the amount of total DNA constant. In theory, each cell transfected with the reporter gene plasmid will, due to its self-replication, express sufficient amounts of reporter protein to be detected. At some ratio of reporter gene vector to carrier DNA, a further increase of reporter gene plasmid will lead to a corresponding increase in the number of transfected cells. By this means, the ideal amount of self-replicating reporter gene plasmid can be determined, reflecting the ideal amount of vector genomes.

Similarly, another read-out system for detection of successfully transfected cells are methods such as in-situ PCR to detect the transfected plasmid genome on a single cell level.

Alternatively, the geno-/phenotypically coupled library of parvovirus virions can be produced by transducing a (non- or partially coupled) virion library into production cells under suitable conditions at a ratio of genomes per cell of 5 to 5,000, preferably 10 to 1,000, more preferably 50 to 300, especially approximately 100, and selecting transduction conditions to be independent from infection pathways, particularly through unspecific uptake through pinocytosis and/or phagocytosis, resulting in geno-/phenotypically coupled virions/library.

Especially relevant for the screening of structural proteins having epitope inserts is the method used for infecting cells after binding virions have been separated from non-binding virions. It is known that a peptide insertion into the I-587 site of AAV2 frequently destroys (depending on the sequence of the inserted peptide) the heparin binding motif required for efficient infection of HSPG-receptor containing cells such as HeLa or 293 cells. It has now been found that an insertion in I-453 optionally in combination with I-587 can alter the transducing activity of respective virions. Therefore, simple infection methods could bias the screening method and lead only to mutants that still can enter HeLa cells specifically through the respective receptor, in case of AAV2 through heparan sulfate proteoglycan (HSPG). Therefore, an unspecific uptake of the virus particle by the production cell may be advantageous. Such unspecific uptake can be achieved by seeding production cells on immobilized parvovirus virions. For this method, the virions are directly coated to a support such as a tissue culture plate. Alternatively, first a capsid-specific antibody (in case of AAV2 for example A20) is coated to the support and second the capsids are bound to the coated antibodies. The advantage in the latter case is that the antibody/virus particle complex, respectively the virus particle itself is more efficiently detached from the support and thereby internalized by the cell. Importantly, introduction of foreign peptide sequences into I-453 of AAV2 does not destroy the affinity of A20 to the respective mutant particle as the epitopes of A20 are hardly if at all affected by the peptide insertion. The cells, e.g. HeLa cells, are finally seeded on the bound capsids. It is expected that this procedure leads to an uptake of the virus, e.g. AAV, by the cell independent of the natural infectious pathway, presumably by pinocytosis and/or phagocytosis.

Alternatively or additionally, the selection step can be carried out on cells expressing a specific receptor for a binder of choice which is used for selecting the wanted parvoviral variant. E.g. cells can be used which express the FcγRI which is specific for any binder comprising an Fc-part of an antibody. For this example, such FcγRI expressing cells can be transduced with a library pool of parvoviruses. First, a negative selection can be performed to avoid unspecific selection of parvoviral candidates which by themselves are able to transduce cells independently from an interaction of a binder with the FcγRI. Therefore, FcγRI-expressing cells are incubated with the library pool. The supernatant (pool of parvoviruses which is not able to transduce the cells) is collected and subsequently incubated with the binder of choice (e.g. selection antibody) to perform the positive selection. In the positive selection parvoviruses decorated with the binder will be able to transduce FcγRI expressing cells through the coupling of the binder to the FcγRI on the surface of the cells. The transduced cells can subsequently be used to amplify the particles in the presence of the binder, assuming that the intracellular trafficking is not impaired within the cells.

In a further preferred embodiment a geno-/phenotypically coupled library of parvovirus virions can be obtained by a method where selected virions are specifically taken up by production cells. In this case the library of parvovirus virions is produced by transducing the library into production cells under suitable conditions at a ratio of genomes per cell of 10 to 10,000, preferably 50 to 5,000, more preferably 100 to 3,000, especially approximately 1,000, wherein transduction conditions are selected to be dependent on infection pathways, particularly through specific receptor binding, resulting in geno-/phenotypically coupled virions/library. In order to achieve such receptor-specific uptake the virions of the library are preferably not immobilized but added to the cells in suspension, whereas both cells and virions can be in suspension or cells are immobilized and virions are added in suspension. Therefore, the transfection of the cells is basically dependent on the virus's infection pathway.

Dependence on infection pathways means that virions are taken up by the cells e.g. through receptor-specific uptake, e.g. for AAV2 heparin sulfate proteoglycan (HSPG)-specific uptake (e.g. for virion libraries where natural infection pathways are not blocked or destroyed by the inserted random peptide sequences). To keep biodiversity of the library during the coupling step (either by transfection of virus genomes or by cell transduction with virion particles by either means, uptake or infection), always a at least 10-fold, preferably 100-fold, especially 500-fold excess of genomic particles compared to the multiplicity of parvoviral mutants should be transduced in order to ensure that each virus variant is amplified. To further ensure that each virus is coupled in the resulting library an at least 2-fold, preferably at least 5-fold excess of cells is to be used compared to total number of genomic particles.

Geno-/phenotype coupling is desired as the genetic information of the packed DNA can easily be used to obtain the sequence of those particles having high affinity or avidity to the respective antigen binder. It is an object of the invention to use for the identification of a parvovirus mutated structural protein such geno-/phenotypically coupled libraries with a coupling of at least 5%, preferably of at least 25% and more preferably of at least 50%, especially at least 90%.

In a preferred embodiment the library of the present invention has a multiplicity of parvoviral mutants of greater than $10^3$, preferably greater than $10^5$, more preferably greater than $10^6$, especially greater than $10^7$. Multiplicity means according to this invention the number of different virions or viral genomes within the library. In principal it is advantageous to use a library of high multiplicity as the likelihood to identify an optimal clone increases with the multiplicity of the library. The multiplicity of the library is generated by insertion of a nucleic acid insert into the coding region of the gene encoding a parvoviral structural protein leading to an amino acids insertion into a position within the parvoviral structural protein.

One embodiment of the present invention is a multimeric structure comprising a parvovirus structural protein of the present invention. A multimeric structure according to this invention is a structure of at least 5, preferably at least 10, more preferably at least 30, most preferably at least 60 structural proteins. They can form regular particles such as capsomeres, virus-like particles (empty viral shells) or capsids. Alternatively, they also can form non-regular aggregates. As explained above the formation of particles capable of packaging a viral genome is a highly preferred feature, particularly if the structural proteins of this invention shall be used as viral vectors. In case the structural proteins are intended for use as vaccines such particle formation may not be necessary to exert a sufficient immune response and capsomeres or aggregates may be sufficient. Still, it is believed that particle formation is also beneficial for the display of the inserted epitopes, especially if direct cross linking of B-cell epitopes is necessary for breaking tolerance.

One embodiment of the present invention is a nucleic acid encoding a structural protein as described above. The nucleic acid is preferably a vector comprising the claimed nucleic. Nucleic acids, especially vectors are necessary to recombinantly express the structural proteins of this invention.

A further embodiment is a library of vectors, wherein the library comprises a set of different vectors described above. In a preferred embodiment the library has a multiplicity of parvoviral mutants of greater than $10^3$, preferably greater than $10^5$, more preferably greater than $10^6$, especially greater than $10^7$. Multiplicity means according to this invention the number of different virions or viral genomes within the library. In principal it is advantageous to use a library of high multiplicity as the likelihood to identify a suitable or even ideal clone increases with the multiplicity of the library.

Another embodiment of the present invention is a virus, preferably a parvovirus as further characterized above, comprising a nucleic acid as characterized above or a vector as characterized above.

Another embodiment of the present invention is an isolated cell comprising a nucleic acid as characterized above or a vector as characterized above.

A further embodiment of the mutated structural proteins according to this invention is their use for gene therapy. The gene therapy vector is formulated to contain common salts, buffer and excipients. The gene therapy vector according to this invention can be administered by common routes of administration such as intra-venously or local or loco-regional.

A further embodiment of the present invention is a process for the preparation of a structural protein of a parvovirus, the method comprising the steps of:

a) expressing a nucleic acid according to this invention under suitable conditions, and
b) isolating the expressed structural protein of step a).

A further embodiments of the present invention is a method for altering the tropism of a parvovirus, the method comprising the steps of: a) co-expressing parvoviral helper and vector functions, wherein the helper function expresses a parvoviral structural protein according to this invention under conditions that enable parvovirus formation, and b) isolating the parvovirus A further embodiment of the present invention is a method for displaying an epitope on the surface of a parvovirus, the method comprising the steps of: a) expressing the nucleic acid according to this invention under suitable conditions, and b) isolating the expressed structural protein of step a).

A further embodiment of the present invention is method for vaccinating a mammal, the method comprising the vaccination of a mammal, preferably a human, with a structural protein, preferably a particle according to this invention. As disclosed above the structural protein is formulated to contain common salts, buffer, excipients and/or adjuvants. Preferred adjuvants are listed below. The vaccines according to this invention can be administered by common routes of administration as described below. Such vaccination is preferably used for breaking immune tolerance, but also for treating infectious diseases, the method comprising the vaccination of a mammal, preferably a human, with a structural protein according to the invention.

A further embodiment of the present invention is a method for transducing cells in vitro or in vivo, the method comprising the steps of: a) co-expressing parvoviral helper and vector functions, wherein the helper function expresses a parvoviral structural protein according to this invention under conditions that enable parvovirus formation, b) isolating the parvovirus, and c) transducing cells with said parvovirus.

A further embodiment of the present invention is a method for producing a library of nucleic acids comprising a multiplicity of expressible nucleic acids according to this invention, comprising the steps of: a) providing a set of nucleic acids encoding each a parvoviral structural protein, b) inserting a library of inserts in frame into a plurality of nucleic acids at a position corresponding to that defined herein.

A further embodiment of the present invention is a medicament comprising at least one parvovirus structural protein according to this invention and/or a nucleic acid according to this invention, preferably at least one multimeric structure according to this invention. Preferably such medicament is used as a vaccine or as a gene transfer vector. The parvovirus structural protein according to this invention, the nucleic acid according to this invention, and the multimeric structure according to this invention may be defined as detailed above.

A further embodiment of the present invention is the use of at least one parvovirus structural protein according to this invention and/or a nucleic acid according to this invention, preferably at least one multimeric structure according to this invention for the manufacture of a vaccine or for use as a gene transfer vector.

As described earlier one preferred utility of the mutated structural proteins according to this invention is their use as a vaccine. Vaccine in the context of this invention means that an immune response, preferably a humoral immune response is generated after administration of the mutated structural protein. The vaccine is formulated to contain common salts, buffer, excipients and/or adjuvants.

The medicament of the present invention may further encompass pharmaceutically acceptable carriers and/or excipients. The pharmaceutically acceptable carriers and/or excipients useful in this invention are conventional and may include buffers, stabilizers, diluents, preservatives, and solubilizers. Remington's Pharmaceutical Sciences, by E. W. Martin, Mack Publishing Co., Easton, Pa., 15th Edition (1975), describes compositions and formulations suitable for pharmaceutical delivery of the (poly)peptides herein disclosed. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In a preferred embodiment the medicament further comprises an immunostimulatory substance such as an adjuvant. The adjuvant can be selected based on the method of administration and may include mineral oil-based adjuvants such as Freund's complete and incomplete adjuvant, Montanide incomplete Seppic adjuvant such as ISA, oil in water emulsion adjuvants such as the Ribi adjuvant system, syntax adjuvant formulation containing muramyl dipeptide, or aluminum salt adjuvants. Preferably, the adjuvant is a mineral oil-based adjuvant, especially ISA206 (SEPPIC, Paris, France), most preferably ISA51 (SEPPIC, Paris, France). In another preferred embodiment the parvovirus mutated structural protein is co-formulated with at least one suitable adjuvant such as CpG, Imidazoquinolines, MPL, MDP, MALP; flagellin, LPS, LTA, or cholera toxin or derivative thereof, HSP60, HSP70, HSP90, saponins, QS21, ISCOMs, CFA, SAF, MF59, adamantanes, aluminum hydroxide, aluminum phosphate or a cytokine.

In a more preferred embodiment the immunostimulatory substance is selected from the group comprising polycationic polymers, especially polycationic peptides such as polyarginine, immunostimulatory deoxynucleotides (ODNs), peptides containing at least two LysLeuLys motifs, especially KLKLLLLLKLK (SEQ ID NO: 126), neuroactive compounds, especially human growth hormone, alumn, adjuvants or combinations thereof. Preferably, the combination is either a polycationic polymer and immunostimulatory deoxynucleotides or of a peptide containing at least two LysLeuLys motifs and immunostimulatory deoxynucleotides. In a still more preferred embodiment the polycationic polymer is a polycationic peptide.

In an even more preferred embodiment of the invention the immunostimulatory substance is at least one immunostimulatory nucleic acid. Immunostimulatory nucleic acids are e.g. neutral or artificial CpG containing nucleic acids, short stretches of nucleic acids derived from non-vertebrates or in form of short oligonucleotides (ODNs) containing non-methylated cytosine-guanine dinucleotides (CpG) in a defined base context (e.g. as described in WO 96/02555). Alternatively, also nucleic acids based on inosine and cytidine as e.g. described in WO 01/93903, or deoxynucleic acids containing deoxy-inosine and/or deoxyuridine residues (described in WO 01/93905 and WO 02/095027) may preferably be used as immunostimulatory nucleic acids in the present invention. Preferably, mixtures of different immunostimulatory nucleic acids are used in the present invention. Additionally, the aforementioned polycationic compounds may be combined with any of the immunostimulatory nucleic acids as aforementioned. Preferably, such combinations are according to the ones described in WO 01/93905, WO 02/32451, WO 01/54720, WO 01/93903, WO 02/13857 and WO 02/095027 and the Australian patent application A 1924/2001.

In a further embodiment the parvovirus mutated structural protein of this invention is used for the manufacture of a vaccine for preventing or treating an autoimmune disease (e.g. diabetes type 1), a tumor disease (examples are: melanoma: e.g. HMW MAA, glioblastome multiforme: e.g. CAl25, anti-IL13R, colon cancer: e.g. CA125 or anti-EGF (R), breast cancer: e.g. HER2/NEU, ovarian cancer: e.g. L1 adhesion molecule, B-cell lymphoma: e.g. CD$_2$O), an allergic disease (asthma, allergies such as allergic rhinitis, e.g. IgE), a metabolic disease (e.g. high cholesterol, intervention into the cholesterol metabolism, obesity, hypertension, e.g. CETP), an inflammatory disease (rheumatoid arthritis, Crohn's disease, psoriasis, e.g. IL-6, IL-17, TNF-α), a neurological disease (e.g. Alzheimer, e.g. β-amyloid) or to be used in ophthalmology.

Examples for autoimmune disease that are especially suitable for this invention are listed in Table 5.

TABLE 5

Autoimmune diseases and suitable antibody targets/antigens

| Disease | antibody target/antigen |
| --- | --- |
| Myasthenia gravis | Acetylcholine receptors |
| Graves's disease | Thyroid-stimulating hormone receptor |
| Thyroiditis | Thyroid |
| Insulin-resistant diabetes | Insulin receptor |
| Asthma | Beta-2 adrenergic receptors |
| Juvenile insulin-dependent diabetes | Pancreatic islet cells |
| Pernicious anemia | Gastric parietal cells |
| Addison's disease | Adrenal cells |
| Idiopathic hypoparathyroidism | Parathyroid cells |
| Spontaneous infertility | Sperm |
| Premature ovarian failure | Interstitial cells, corpus luteum cells |
| Pemphigus | Intercellular substance of skin |
| Primary biliary cirrhosis | Mitochondria |
| Autoimmune hemolytic anemia | Erythrocytes |
| Idiopathic thrombocytopenic purpura | Platelets |
| Idiopathic neutropenia | Neutrophils |
| Vitiligo | Melanocytes |
| Osteosclerosis and Meniere's disease | Type-II collagen |
| Chronic active hepatitis | Nuclei of hepatocytes |
| Goodpasture's syndrome | Basement membranes |
| Rheumatoid arthritis | Gamma globulin, virus-related antigens, IL-6, IL-17, TNF-α |
| Sjogren's syndrome | Nuclei and centromeres |
| Systemic lupus erythematosus | Nuclei, DNA, RNA, erythrocytes, etc. |
| Scleroderma | Nuclei and centromeres |
| Polymyositis | Nuclei, RNA |

Preferred autoimmune diseases are asthma, Juvenile insulin-dependent diabetes (diabetes type 1) and rheumatoid arthritis. Therefore, preferred antigens are the corresponding antigens of Beta-2 adrenergic receptors, pancreatic islet cells, Gamma globulin E, virus-related antigens, IL-6, IL-17 and TNF-α.

Examples for tumor diseases disease that are especially suitable for this invention are listed in Table 6.

TABLE 6

Tumor diseases and suitable antibody targets/antigens

| Disease | antibody target/antigen |
| --- | --- |
| Melanoma | HMW MAA (=high molecular weight melanoma associated antigen), BAGE, GAGE, MAGE-3, Melan A, MART-1, NY ESO, gp 100, tyrosinase |
| Colon cancer | CA125, EGFR |
| Gliobastome multiforme (GBM) | CA125, IL13R |
| Breast cancer | Her2/NEU |
| Ovarian cancer | L1 cell adhesion molecule |
| various cancers (e.g. for colon cancer, small lung cell carcinoma) | VEGF |
| B-cell lymphoma, e.g. Non-Hodgkin Lymphoma | CD20 |

Examples for allergic diseases are asthma, especially atopic asthma, and all types of allergies. The preferred target antigens for vaccination against allergic diseases are IgE, IL-9, and IL-13, especially IgE.

An example for a metabolic disease is a disorder in the cholesterol metabolism (e.g. atherosclerosis), a preferred target antigen is CETP.

Examples for inflammatory diseases that are especially suitable for this invention are listed in Table 7.

TABLE 7

Inflammatory diseases and suitable antibody targets/antigens
Disease

COPD (chronic obstructive pulmonary disease)
OA (osteoarthritis)
Rheumatoid arthritis
Polymyalgia rheumatica
Gouty arthritis, Gout, Pseudogout
Atherosclerosis
Crohn's disease (inflammatory bowel disease)
Shoulder tendinitis, Bursitis
Colitis
Multiple Sclerosis
Systemic Lupus Erythematosus
Psoriasis
Juvenile diabetes
Type I diabetes mellitus (insulin-resistant diabetes)
Hypothyroidism
Chronic fatigue syndrome
Kawasaki's disease
Cardiavascular disease
Pericarditis
Lymph adenopathy
Raynaud's phenomenon
Sarcoidosis
Sjogren's syndrome
Spondyloarthropathies
Vasculitides
Scleroderma
Goodpasture's syndrome
Wegener's granulomatosis
temporal = Giant cell arteritis
Celiac disease
Addison's disease
Autoimmune hepatitis
Grave's disease
Graft-vs-host disease Preferred target antigens are TNF-α, CD20, IL-6 and IL-17.

Examples for diseases in ophthalmology are age-related macular degeneration (AMD) and diabetic retinopathy, a preferred target in these indications is VEGF.

Other preferred diseases are Alzheimer disease with the target antigen β-amyloid.

The parvovirus mutated structural protein according to this invention can be especially useful for manufacture of a medicament for breaking immune tolerance.

In the context of the uses of the invention, the features of the parvovirus mutated structural protein are as defined above.

In a preferred embodiment the disease is not an infectious disease, meaning a disease caused by a virus, a bacterium, a fungus or a eukaryotic parasite.

In a further embodiment parvovirus mutated structural protein is not used to make a vector that is used in gene therapy.

A preferred embodiment of the instant invention is a structural protein of a parvovirus as further defined above comprising an anti-idiotypic epi-/mimotope of an anti-IgE antibody, and/or an IgE epi-/mimotope. Preferred vaccines are the following:

Vaccines for the Treatment of Asthma and Allergic Diseases

Atopic asthma and allergic rhinitis are caused by adverse immune responses, typified by IgE, against otherwise harmless environmental proteins, allergens. In sensitized individuals, allergen-specific IgE becomes localized in tissues by binding to the high-affinity receptor for IgE, FcεRI, expressed by mast cells in various tissues and basophils as well as eosinophils in the blood. Subsequent encounters with the allergen result in cross-linking of IgE/FcεRI, which triggers effector cell degranulation and the release of both preformed mediators (histamine, proteolytic enzymes, and proteoglycans) and de novo synthesized mediators (prostaglandin $D_2$, leukotrienes, and cytokines). Together, these mediators are responsible for the clinical manifestations of allergic reactions, including hay fever, asthma, and eczema, as well as life-threatening anaphylactic reactions. Standard therapy includes inhaled corticosteroids (ICS), Beclomethasone Dipropionate (BDP), long-acting β-agonists (LABA) and leukotriene receptor antagonists (LTRAs).

The receptor-binding region of human IgE was previously mapped to the N-terminal region of the CH3 domain (Helm et al., 1988, Helm et al., 1989). Site-directed mutagenesis studies to identify the amino acid residues directly involved in the interaction have been conducted on both IgE (Presta et al., 1994) and FcεRI (Cook et al., 1997). In addition, the crystal structure of the human IgE-FcεRIα to complex was recently solved by Garman and colleagues (Garman et al., 2000). The amino acid regions that are involved in receptor binding are localized in three loops and spread over most of the Cε3 domain (Pro-364, Arg-365, Arg-408, Ser-411, Lys-415, Glu-452, Arg-465, and Met-469). Binding is mediated primarily by electrostatic interaction.

Anti-IgE therapy is based on antibodies which bind the receptor-binding target domain Cε3 region of IgE, thereby preventing the binding of IgE to the FcεRI receptor and, therefore, preventing sensitization of mast cells and basophils. However, even if 99% of free IgE was neutralized by the anti-IgE antibody, the therapy still would fail because the few remaining IgE molecules would be sufficient to sensitize the respective cells. Therapeutic efficacy is provided through additional actions: FcεRI expression is regulated by the level of free IgE, in a way that reduced levels of free IgE lead to lowered densities of FcεRI on basophils and mast cells and lowered sensitivities. And, anti-IgE may lead to down-regulation of IgE production by eliminating or down-regulating IgE-expressing B cells, perhaps by cross-linking membrane-bound IgE and causing apoptosis, anergy or most likely also by complement-mediated and cell-mediated cytolysis; The latter mechanism was, however, not found in clinical trials performed with Omalizumab. For this monoclonal antibody, reduction of IgE production from B-cells (plasma cells) mediated by lowered IgE levels was only observed in animal and in-vitro experiments.

Most of the therapeutic monoclonal antibodies in development can only bind and neutralize free IgE or IgE associated with B-cells. In contrast, FcεRI-bound IgE is not accessible for these anti-IgE antibodies. Anti-IgE antibodies directed against regions of the IgE molecule outside of the receptor binding region (such as the variable, antigen-binding domain of IgE referred to as the IgE idiotype), can bind to an IgE molecule while it is bound to its receptor. This results in cross-linking of receptor-bound IgE, causing an anaphylactic shock in animals treated systemically with such antibodies. Importantly, except for defense mechanisms against parasite infections, IgE seems to play no role in normal physiology and IgE-deficient people are healthy with no apparent sign of pathology (Levy and Chen, 1970).

Omalizumab (XOLAIR®) is a humanized monoclonal anti-IgE antibody for passive immunization, and the first available/approved anti-IgE therapy on the market. A total of 7 phase III clinical trials were performed with this monoclonal anti-IgE antibody, which bind to the Cε3 region of IgE (for a review refer to (Bousquet et al., 2005)) without cross linking the FcεRI receptor. Omalizumab significantly reduced the rate of asthma exacerbations by 38% and the rate of total emergency visits by 47%. The efficacy of Omalizumab was unaffected by patient age, gender, baseline serum IgE or by 2- or 4-weekly dosing schedule, although benefit in absolute terms appeared to be greatest in patients with more severe asthma, defined by a lower value of percentage predicted forced expiratory volume in 1 s ($FEV_1$) at baseline.

As outlined before, one disadvantage of passive immunization with a monoclonal antibody is the requirement of infusions every 2-4 weeks with relatively high antibody doses making such therapies expensive. Therefore, alternative approaches are needed for the treatment of allergic diseases such as atopic allergies or asthma.

According to the present invention this problem is solved by a structural protein of a parvovirus comprising an anti-idiotypic epi-/mimotope of an anti-IgE antibody, and/or an IgE epi-/mimotope inserted at the insertion site I-453. Such structural proteins are preferably capable of forming virus-like particles. They harbor anti-idiotypic epi-/mimotopes of an anti-IgE antibody and/or IgE epi-/mimotopes on the surface of the capsid shell. Therefore the anti-idiotypic epi-/mimotopes of an anti-IgE antibody, respectively the IgE epi-/mimotopes are accessible to the humoral immune system. Such structural protein can be used as vaccines in patients in order to induce specifically an immune response against IgE, meaning antibodies that cross-react with IgE (anti-IgE antibodies), thereby preventing binding of IgE to its high affinity receptor FcεRI.

Especially preferred embodiments of the invention are structural proteins of parvoviruses, especially AAV, that contain IgE epitopes or mimotopes, preferably previously known epitopes or mimotopes inserted at insertion site I-453 that can be used as vaccines. In a preferred embodiment the B-cell epitope is a human epitope. Preferably it is inserted into I-453 and at least one further insertion site, preferably I-261, I-534, I-570, I-573 or I-587, especially into I-453 and I-587, preferably of AAV1, AAV2 or AAV-6.

For a lot of the publicly available therapeutic antibodies which can be used as target antibody for AAV selection, the epitopes are not known. To be able to compare the epitopes of the target antibodies and the antibodies induced in e.g. mice after vaccination, epitope mapping can be performed. For example, epitopes recognized by anti mouse or anti human IgE antibodies can be identified from arrays using overlapping peptide scans from the respective IgE spotted on nylon membranes. Preferred antibodies are those with a binding pattern similar to that of Omalizumab, which can be used for selection of mimotopes from the AAV capsid library. Epitopes recognized by antibodies induced in e.g. mice after vaccination can be identified from arrays spotted on glass slides. Cross-reactivity of anti human IgE antibodies or antibodies induced in mice after vaccination with the constant chain regions of other Ig's can be monitored in Westernblot experiments.

Especially preferred embodiments of the invention are structural proteins of parvoviruses, especially AAV, that contain IgE epitopes or mimotopes, preferably previously known epitopes or mimotopes.

Preferred IgE epitopes or mimotopes can first be identified as described by Rudolf, Stadler, Vogel and colleagues (Rudolf et al., 1998, Rudolf et al., 2000, Stadler et al., 1999, Vogel et al., 2000): one can develop so-called mimotope immunization vaccines based on peptide phage display libraries screened for particles recognizing BSW17, a mouse monoclonal anti-human IgE antibody. Peptide sequences best recognized by BSW17 are the preferred epitopes/mimotopes (SEQ ID NO: 55)
ECINHR<u>G</u>Y<u>WV</u>CGD ("Rudolf" (Rudolf et al., 2000), with G, W and V (underlined) being conserved among all sequences identified (the cysteine residues (in bold) mediate a circular form of the peptide via disulfide bridging), C4M' (Rudolf et al., 2000), and Kricek (Kricek et al., 1999).

Second, in the course of this invention previously unknown epitopes that are especially suitable for vaccination purposes against allergic diseases like asthma have been identified which are preferred IgE epitopes which are preferred IgE epitopes: Bind2, Flex, 3DEpi1, 3DEpi2, 3DEpi3, 3DEpi4, C4E, Wang-CS, Wang and C21.

The present invention further relates to novel IgE B-cell epitopes Bind2, Flex, 3DEpi1, 3DEpi2, 3DEpi3, 3DEpi4, C4E, Wang-CS, Wang, and C21 and/or to a functionally active variant thereof. A functionally active variant of these epitopes means a B-cell epitope which generates in a rabbit vaccination experiment according to example 8.6 a B-cell response in this case measurable as titer of specific antibodies binding to human IgE.

Such functionally active variants can either be single peptides or mixtures of single peptides consisting of peptide sequences of up to 40 amino acids, preferably up to 25 amino acids, more preferably 15 amino acids, especially 9 amino acids of the given sequence, or a fusion of such functionally active variant to a carrier. Such carrier is meant to be any molecule except for the naturally occurring IgE protein or part thereof (larger than the functionally active variant), preferably a parvoviral particle, but also a different virus- or bacteriophage particle, a polymer (e.g. LPH) or a fusion protein, capable of generating a B cell response (as defined above) against such functionally active variant. Such fusion to a carrier can i.e. be obtained by chemically linking the variant to the carrier or by genetically making fusion proteins or insertion variants.

These and similar sequences or parts therefore including or excluding the cysteine residues and flanking sequences can be introduced into positions I-453 and others of AAV VP. The corresponding AAV particles can be manufactured (initially as genome-containing infectious AAV), purified and characterized. Although AAV capsids have a different conformational structure than phages, the chance that a similar structure of the mimotope sequence EFCINHR<u>G</u>Y <u>WV</u>CGD (SEQ ID NO: 55) is present on both, phages and AAV, is high due to the cysteine residues building up a loop structure of the peptide sequence. For linear epitopes such as Kricek (VNLTVVSRASG, SEQ ID NO: 50), interchangeability should also be possible. If these AAV particles bind BSW17 (the anti-IgE antibody used for phage display), they can be used as an anti-IgE vaccine that can be used with and without co-formulation in a suitable adjuvant (as described herein).

Especially preferred embodiments of the invention are structural proteins of parvoviruses that contain IgE epi-/mimotopes that, once injected into an immunocompetent mammal, induce anti-IgE specific antibodies with therapeutic efficacy without cross-linking properties. Cross-linking properties means that in an immunocompetent mammal the generated anti-IgE antibodies are binding IgE molecules in a way that IgE/FcεRI binding is still possible. By such way, and if one antibody binds several IgE molecules at a time, the high-affinity FcεRI receptor is cross linked on effector cells leading to its degranulation. This would induce a systemic anaphylactic shock. On the other hand, the structural proteins of parvoviruses should be able to directly crosslink the respective B-cell receptor (binding the IgE epi-/mimotopes or the anti-idiotype epi-/mimotope of an anti-IgE antibody) to activate the corresponding B-cells and to induce anti-IgE antibody production independent of a T-cell response.

Vaccines for the Treatment of Alzheimer's Disease

In general, misfolded proteins leading to a protein aggregation and, therefore, causing conformational diseases, are good candidate targets for an active immunization approach with AAV vaccines. Ideally, B-cell epitopes represented by misfolded proteins or protein aggregates only are chosen for presentation on AAV particles (for an overview, please refer to Uversky et al., 2006, especially table 1-1).

Especially preferred embodiments of the invention are structural proteins of parvoviruses, especially AAV, that contain β-amyloid epitopes or mimotopes at insertion site I-453, preferably known epitopes or mimotopes, that can be used for the treatment of Alzheimer disease. In the context of the present invention a B-cell epitope of β-amyloid was inserted into a parvovirus capsid and displayed on the surface of the capsid. In a preferred embodiment the B-cell epitope is a human epitope. Preferably it is inserted into I-453 and at least one further insertion site, preferably I-261, I-534, I-570, I-573 or I-587, especially into I-453 and I-587 of preferably AAV1, AAV2 or AAV6. In an especially preferred embodiment the B-cell epitope has the sequence DAEFRHDSG (SEQ ID NO: 65).

Vaccines for the Treatment of Atherosclerosis

Atherosclerosis is a disease affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a "hardening" or "furring" of the arteries. It is caused by the formation of multiple plaques within the arteries. There is a strong inverse relationship between the plasma concentration of cholesterol in HDLs (HDL-C) and the development of coronary heart disease (CHD). Plasma concentration of HDL-C is a powerful predictor of CHD. Although 33% of patients with CHD have low plasma levels of HDL-C as their primary lipid abnormality, there is currently no effective therapy for increasing the plasma concentration of HDL-C. Diet and moderate exercise are ineffective, statins afford only a modest 5% to 7% increase in HDL-C, and niacin has side effects and compliance profiles that limit its use.

One therapeutic approach that has been suggested for increasing plasma HDL-C concentrations is the inhibition of cholesteryl ester transfer protein (CETP) activity. CETP is a 74-kDa plasma glycoprotein that facilitates transfer of neutral lipids and phospholipids between lipoproteins and contributes to the regulation of plasma concentration of HDL-C. CETP functions in the plasma to lower the concentration of HDL-C by moving cholesteryl esters from HDLs to VLDLs and LDLs (Rittershaus et al., 2000).

Accordingly it is a further embodiment of the invention to provide structural proteins of parvoviruses, especially AAV, that contain CETP epitopes or mimotopes at insertion site I-453 that can be used as a vaccine for the treatment of atherosclerosis. Preferably the epitope or mimotope is inserted into I-453 and at least one further insertion site, preferably I-261, I-534, I-570, I-573 or I-587, especially into I-453 and I-587, preferably of AAV1, AAV2 or AAV-6. Suitable epitopes or mimotopes are the human CETP derived peptides hTP10, hTP11, hTP12, hTP13, hTP18 and hTP20, hRitsch-1, hRitsch-2, hRitsch-3, hCETP-intern and hCETP C-Term.

The present invention further relates to novel CETP B-cell epitopes hTP10, hTP11, hTP12, hTP13, hTP18, hTP20, hRitsch-1, hRitsch-2, hRitsch-3, hCETP-intern and hCETP C-Term and/or to a functionally active variant thereof.

Vaccines for the Treatment of Tumor Diseases

Antibody therapies such as HERCEPTIN®, AVASTIN®, ERBITUX®, OMNITARG®, RITUXAN®, CAMPATH®, ZEVALIN®, MYLOTARG®, BEXXAR® or Panitumumab play an increasing role in fighting various types of tumor diseases. These antibodies specifically bind epitopes of factors causing uncontrolled cellular growth, such as growth factor receptors or growth factors. Accordingly, it is a further embodiment of this invention to provide structural proteins of parvoviruses, especially AAV, that contain epitopes of such factors causing uncontrolled cellular growth.

HER2/neu (also known as ErbB-2, ERBB2) is a protein giving higher aggressiveness in breast cancers. It is a member of the ErbB protein family, more commonly known as the epidermal growth factor receptor family. HER2/neu has also been designated as CD340. HER2/neu is notable for its role in the pathogenesis of breast cancer and as a target of treatment. It is a cell membrane surface-bound receptor tyrosine kinase and is normally involved in the signal transduction pathways leading to cell growth and differentiation. Approximately 25-35 percent of breast cancers have amplification of the HER2/neu gene or over expression of its protein product. Overexpression also occurs in other cancer such as ovarian cancer and stomach cancer. Clinically, HER2/neu is important as the target of the monoclonal antibody trastuzumab (marketed as HERCEPTIN®).

As for an active vaccination approach, the epitope sequence QMWAPQWGPD (SEQ ID NO: 123) presented in a circular way has been shown to induce polyclonal antibodies with therapeutic effectiveness. Therefore, a Her2/NEU-AAV vaccine can be generated by insertion of this peptide into AAV using suitable adaptor sequences (Riemer et al., 2007).

Accordingly, especially preferred embodiments of the invention are structural proteins of parvoviruses, especially AAV, that contain epitopes or mimotopes of tumor antigens, preferably HER2/neu, especially the epitope described by Riemer, at I-453, preferably known epitopes or mimotopes. In the context of the present invention a B-cell epitope of HER2/neu can be inserted into a parvovirus capsid and displayed on the surface of the capsid. In a preferred embodiment the B-cell epitope is a human epitope. Preferably it is inserted into I-453 and at least one further insertion site, preferably I-261, I-534, I-570, I-573 or I-587, especially into I-453 and I-587, preferably of AAV1, AAV2 or AAV-6.

Vaccines for the Treatment of Autoimmune Diseases and Chronic Inflammatory Diseases Autoimmune diseases as well as inflammatory diseases arise from an overactive immune response of the body against substances and tissues normally present in the body. In other words, the body attacks its own cells.

Rheumatoid arthritis (RA) is an autoimmune disease which causes chronic inflammation of the joints, the tissue around the joints, as well as other organs in the body affecting 0.5-1.0% of the population in the industrialized world. It commonly leads to significant disability and consequently to a significant reduction of quality of life. If not treated appropriately, RA leads to a reduction of life expectancy (Smolen and Steiner, 2003).

Psoriasis is a chronic inflammatory disease of the skin characterized by overgrowth of epidermal cells, angiogenesis, infiltration of immune cells, and increased production of cytokines. Similar activation of immune cells and increased production of cytokines is associated with autoimmune diseases and (chronic) inflammatory diseases as further listed below.

In order to limit or control such disease causing/related immune responses it has become an established therapeutic modality to neutralize cytokines involved in the pathogenesis of autoimmune and inflammatory diseases. Antibodies (infliximab, adalimumab) and a soluble receptor construct neutralizing the action of TNF-$\alpha$ (etanercept) have been established in the treatment of RA and other disease. Now there is evidence implicating several novel cytokines, including IL-32 and IL-17, in the pathogenesis of RA. In addition we assess the development of existing targets as they move towards clinical evaluation, particularly IL-1, IL-6, IL-15, IL-18 and the IL-12 superfamily (Asquith et al., 2007).

Accordingly, preferred embodiments of the invention are structural proteins of parvoviruses, especially AAV, that contain epitopes or mimotopes of cytokines, preferably of TNF-$\alpha$, IL-6 and/or IL-17, preferably known epitopes or mimotopes, inserted at insertion site I-453 that can be used as vaccines for the treatment of autoimmune diseases and/or chronic inflammatory diseases, preferably rheumatoid arthritis and/or Crohn's disease. In a preferred embodiment the B-cell epitope is a human epitope. In a preferred embodiment the B-cell epitope is a human epitope or mimotope. Preferably it is inserted into I-453 and at least one further insertion site, preferably I-261, I-534, I-570, I-573 or I-587, especially into I-453 and I-587, preferably of AAV1, AAV2 or AAV-6.

Preferred B-cell epitopes are the human epitopes:
TNF-α V1, TNF-α V2, TNF-α V3, IL-17 V1, IL-17 V2, IL-6 V1, IL-6 V2

The present invention further relates to novel cytokine B-cell epitopes TNF-α V1, TNF-α V2, TNF-α V3, IL-17 V1, IL-17 V2, IL-6 V1 and IL-6 V2 and/or to a functionally active variant thereof.

Vaccines for the Treatment of Infectious Diseases

Blocking of viral infection by induction of auto-antibodies against the cellular receptor of the virus is a suggested mechanism of a preventive or therapeutic vaccination against viruses, preferably for viruses where classical vaccination attemps have failed like HIV using CCR5 as the target receptor (Chackerian, 1999).

Accordingly, preferred embodiments of the invention are structural proteins of parvoviruses, especially AAV, that contain epitopes or mimotopes of viral receptors, preferably of CCR5, preferably known epitopes or mimotopes, inserted at insertion site I-453 that can be used as vaccines for the treatment of such viral infection and associated diseases, preferably HIV infection/AIDS. In a preferred embodiment the B-cell epitope is a human epitope. In a preferred embodiment the B-cell epitope is a human epitope or mimotope. Preferably it is inserted into I-453 and at least one further insertion site, preferably I-261, I-534, I-570, I-573 or I-587, especially into I-453 and I-587, preferably of AAV1, AAV2 or AAV-6.

Preferred B-cell epitopes are HYAAAQWDFGNTMCQL (SEQ ID NO: 113), YAAQWDFGNTMCQ (SEQ ID NO: 114), RSQKEGLHYT (SEQ ID NO: 115) or a functionally active variant thereof.

Accordingly, a further aspect of the present invention relates to a medicament of the invention for the treatment and/or prevention of a) an allergic disease and/or asthma whereas at insertion site I-453, and preferably at at least one further insertion site, more preferably at insertion site I-261, I-534, I-570, I-573 or I-587, especially I-453 and I-587, preferably of AAV1, AAV2 or AAV-6, the structural protein of a parvovirus comprises an anti-idiotypic epi-/mimotope of an anti-IgE antibody, and/or an IgE epi-/mimotope, particularly a mimotope of sequence of EFCINHRGYWVCGD (SEQ ID NO: 55), with the first G, W and V being conserved and cysteine residues C mediating a circular form of the peptide via disulfide bridging, VNLTWSRASG (SEQ ID NO: 50) or INHRGYWV (SEQ ID NO: 95) or particularly an epitope selected from the group consisting of EKQRNGTLT (SEQ ID NO: 86), EDGQVMDVDLS (SEQ ID NO: 85), TYQCRVTHPHLPRALMR (SEQ ID NO: 87), RHSTTQPRKTKGSG (SEQ ID NO: 88), DSNPRGVSAYLSR (SEQ ID NO: 89), TITCLWDLAPSK (SEQ ID NO: 90), KTKGSGFFVF (SEQ ID NO: 91), THPHLPRALMRS (SEQ ID NO: 92), GETYQCRVTHPHLPRALMRSTTK (SEQ ID NO: 93, LPRALMRS (SEQ ID NO: 94) and a functionally active variant thereof;
b) Alzheimer's disease whereas at insertion site I-453, and preferably at at least one further insertion site, more preferably at insertion site I-261, I-534, I-570, I-573 or I-587, especially I-453 and I-587, preferably of AAV1, AAV2 or AAV-6, the structural protein of a parvovirus comprises a β-amyloid epitope or mimotope, particularly comprising or having the sequence DAEFRHDSG (SEQ ID NO: 65) or a functionally active variant thereof;
c) atherosclerosis whereas at insertion site I-453, and preferably at at least one further insertion site, more preferably at insertion site I-261, I-534, I-570, I-573 or I-587, especially I-453 and I-587, preferably of AAV1, AAV2 or AAV-6, the structural protein of a parvovirus comprises a CETP epitope or mimotope, particularly an epitope selected from the group consisting of PKTVSNLTESSSESVQS (SEQ ID NO: 102), SLMGDEFKAVLET (SEQ ID NO:103), QHSVAYTFEED (SEQ ID NO: 104), INPEIITRDG (SEQ ID NO: 105), DISLTGDPVITASYL (SEQ ID NO: 106), DISLTGDPVITA (SEQ ID NO: 107), DQSIDFEIDSA (SEQ ID NO: 108), KNVSEDLPLPTFSPTLLGDS (SEQ ID NO: 109), KNVSEDLPLPT (SEQ ID NO: 110), CDSGRVRTDAPD (SEQ ID NO: 111), FPEHLLVDFLQSLS (SEQ ID NO: 112) and a functionally active variant thereof;
d) a tumor disease whereas at insertion site I-453, and preferably at at least one further insertion site, more preferably at insertion site I-261, I-534, I-570, I-573 or I-587, especially I-453 and I-587, preferably of AAV1, AAV2 or AAV-6, the structural protein of a parvovirus comprises a tumor antigen, particularly a HER2/neu epitope or mimotope, especially the epitope QMWAPQWGPD (SEQ ID NO: 123) or a functionally active variant thereof; or
e) an autoimmune disease and/or a chronic inflammatory disease, preferably rheumatoid arthritis and/or Crohn's disease, whereas at insertion site I-453, and preferably at at least one further insertion site, more preferably at insertion site I-261, I-534, I-570, I-573 or I-587, especially I-453 and I-587, preferably of AAV1, AAV2 or AAV-6, the structural protein of a parvovirus comprises an epitope or mimotope of a cytokine, preferably of TNF-α, IL-6 and/or IL-17, especially an epitope selected from the group consisting of SSRTPSDKPVAHWANPQAE (SEQ ID NO: 116), SRTPSDKPVAHWANP (SEQ ID NO: 117), SSRTPSDKP (SEQ ID NO: 118), NADGNVDYHMNSVP (SEQ ID NO: 119), DGNVDYHMNSV (SEQ ID NO: 120), RSFKEFLQSSLRALRQ (SEQ ID NO: 121), FKEFLQSSLRA (SEQ ID NO: 122) or or a functionally active variant thereof.
f) an infectious disease, preferably HIV infection, whereas at insertion site I-453, and preferably at at least one further insertion site, more preferably at insertion site I-261, I-534, I-570, I-573 or I-587, especially I-453 and I-587, preferably of AAV1, AAV2 or AAV-6, the structural protein of a parvovirus comprises an epitope or mimotope of a viral receptor, preferably of CCR5, especially an epitope selected from the group consisting of HYAAAQWDFGNTMCQL (SEQ ID NO: 113), YAAQWDFGNTMCQ (SEQ ID NO: 114), RSQKEGLHYT (SEQ ID NO: 115) or a functionally active variant thereof.

FIGURES

FIG. 1: Schematic organization of the cap gene of AAV2

FIG. 2: Amino acid sequence alignment of various parvoviruses with a boxed insertion site I-453.

For references for the aligned parvoviruses see FIG. 3. Further parvoviruses can be found at the NCBI website. The corresponding amino acids to $G_{453}$ are boxed. AAV-2, SEQ ID NO: 165; AAV-5, SEQ ID NO: 166; AAV-1, SEQ ID NO: 167; AAV-6, SEQ ID NO: 168; AAV-8, SEQ ID NO:169; AAV-10, SEQ ID NO: 170; AAV-3B, SEQ ID NO: 171; AAV-7, SEQ ID NO: 172; AAV-4, SEQ ID NO: 173; AAV-11, SEQ ID NO: 174; b-AAV, SEQ ID NO: 175: FPV, SEQ ID NO: 176; CPV, SEQ ID NO: 177; B19, SEQ ID NO: 178; GPV, SEQ ID NO: 179; MVM, SEQ ID NO: 180.

FIG. 3: Amino acid sequence alignment of parvoviruses (AAV1 (SEQ ID NO: 181), AAV6 (SEQ ID NO: 182), AAV2 (SEQ ID NO: 183), AAV3b (SEQ ID NO: 184), AAV7 (SEQ ID NO: 185), AAV8 (SEQ ID NO: 186), AAV10 (SEQ ID NO: 187), AAV4 (SEQ ID NO: 188), AAV11 (SEQ ID NO: 189), bAAV (SEQ ID NO: 190), AAV5 (SEQ ID NO: 191), GPV (SEQ ID NO: 192), B19 (SEQ ID NO: 193), MVM (SEQ ID NO: 194), FPV (SEQ ID NO: 195), and CPV (SEQ ID NO: 196))

Alignment was made using Multalin version 5.4.1, (Corpet, 1988). Symbol comparison table: blosum62, Gap weight: 12, Gap length weight: 2, Consensus levels: high=90% low=50%. Consensus symbols: ! is anyone of IV; $ is anyone of LM; % is anyone of FY; # is anyone of NDQEBZ. The amino acids corresponding to $N_{587}$ of AAV2 and the preferred insertion range for I-587 are boxed.

| Name | Length | Check | Weight | Seq. GP-No. |
|---|---|---|---|---|
| AAV1 | 799 | 4900 | 0.26 | 9632548 |
| AAV6 | 799 | 5176 | 0.26 | 2766607 |
| AAV2 | 799 | 2359 | 0.50 | 2906023 |
| AAV3b | 799 | 3639 | 0.50 | 2766610 |
| AAV7 | 799 | 132 | 0.50 | 22652859 |
| AAV8 | 799 | 3007 | 0.37 | 22652862 |
| AAV10 | 799 | 4671 | 0.37 | 48728343 |
| AAV4 | 799 | 7292 | 0.74 | 2337940 |
| AAV11 | 799 | 2546 | 0.74 | 48728346 |
| b-AAV | 799 | 5299 | 0.79 | 48696559 |
| AAV5 | 799 | 5950 | 1.34 | 91134730 |
| GPV | 799 | 3208 | 1.92 | 9628653 |
| B19 | 799 | 1920 | 2.45 | 4092542 |
| MVM | 799 | 332 | 2.05 | 2982110 |
| FPV | 799 | 7156 | 1.61 | 494031 |
| CPV | 799 | 7674 | 1.61 | 494746 |
| consensus | 799 | 6436 | 0.00 | |

Figure 4:
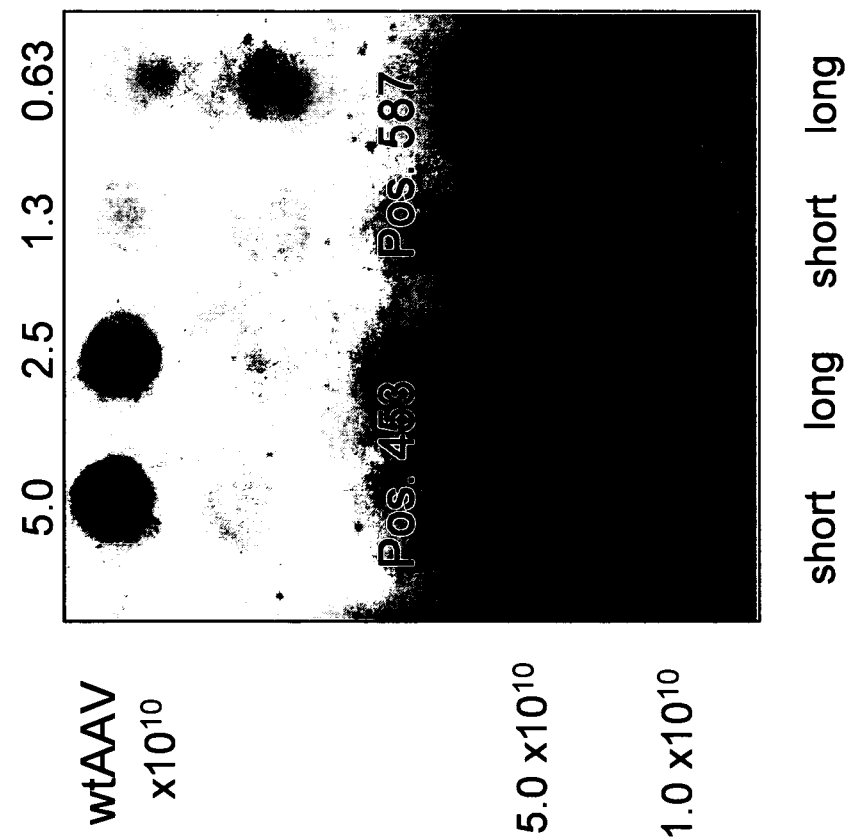

FIG. 4: Interaction of an anti-CETP antibody with the respective CETP epitope inserted into the AAV2 capsid at position I-453 and I-587 $5.0 \times 10^{10}$ and $1.0 \times 10^{10}$ capsids of the variants AAV-CETP-453-short and AAV-CETP-453-long (for further details see example 1.2) were spotted onto a nitrocellulose membrane. In addition, $5.0 \times 10^{10}$ capsids of the variants AAV-CETP-587-short and AAV-CETP-587-long were spotted onto the same membrane. As negative control wtAAV was spotted ranging from $5.0 \times 10^{10}$ to $6.3 \times 10^{9}$ capsids per dot. The membrane was incubated with a polyclonal anti-CETP antibody directed against the CETP epitope inserted into the AAV capsid. Binding of the anti-CETP antibody to the spotted AAV variants was detected with an anti-rabbit IgG HRP (horse radish peroxidase) conjugate.

Figure 5:
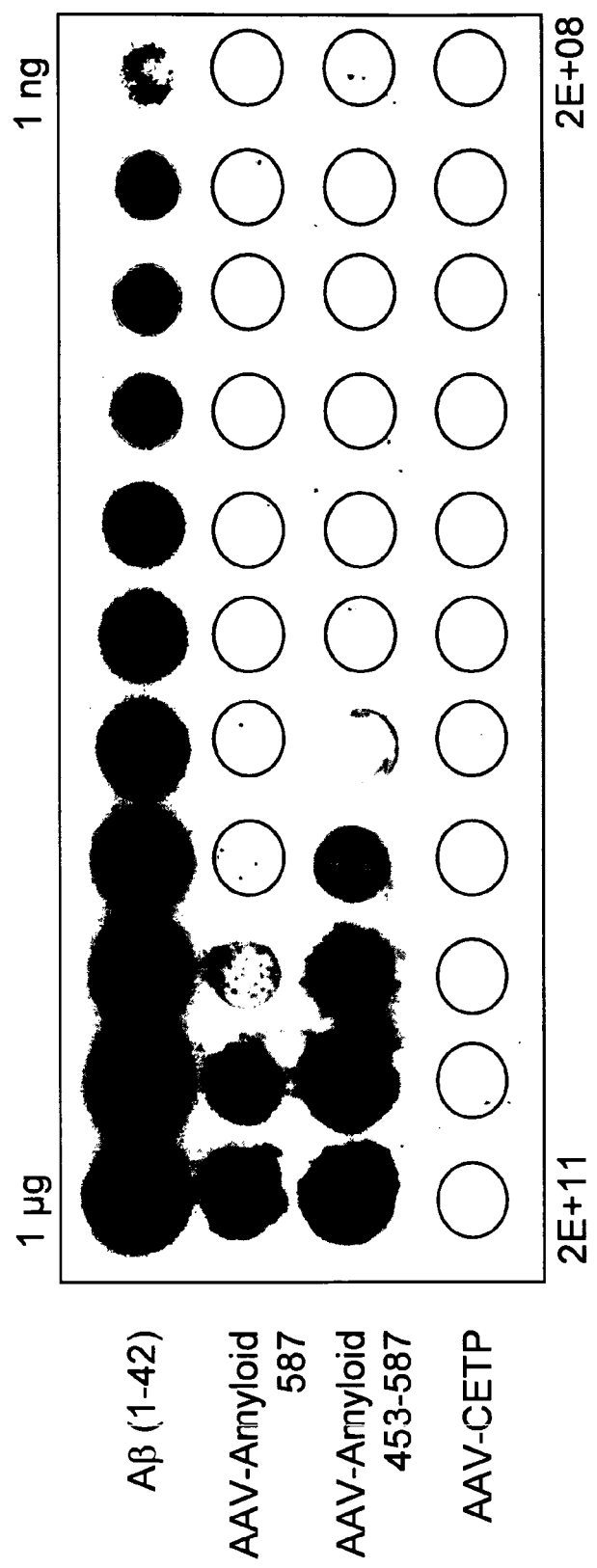

FIG. 5: Detection of a β-amyloid epitope displayed by AAV2 at I-587 or I-453/I-587 by β-amyloid-specific antibody Serial dilutions ($2 \times 10^{11}$–$2 \times 10^{8}$ capsids) of purified AAV particles displaying a β-amyloid epitope at I-587, I-453 and I-587, a CETP epitope at I-587 (as negative control) and 1 μg to 1 ng of the β-amyloid peptide (aa 1-42, BIOSOURCE, as positive control) were dotted on a membrane. The β-amyloid epitope was detected using an anti-β-amyloid mAb $6 \times 10^{10}$ (CHEMICON) and as secondary antibody a peroxidase-labeled anti-mouse IgG antibody (CALTAG). Signals were detected by chemiluminescence.

FIG. 6: Normalization of AAV2 particles detected by monoclonal antibody A20

ELISA plate was coated with A20 (75 ng/well, PROGEN). After blocking (PBS, 1% Milk Powder, 1% Tween) $1.00 \times 10^{10}$ particles were given per well. For detection of a functional RGD purified $\alpha_v \beta_3$ integrin (100 ng/well, CHEMICON) was added to the plate and detected with anti-integrin $\alpha_v$ antibody (C-terminus/intracellular, Dil. 1:1000, CHEMICON). For quantification of viral particles in each well biotinylated A20 (250 ng/well, PROGEN) was used. The ratio "anti-integrin $\alpha_v$": "A20-biot" was used for normalization of the amount of $\alpha_v \beta_3$-binding to total particles.

FIG. 7: HSPG independent transduction

Chinese Hamster Ovarian cells with HSPG KO phenotype were transduced with 1,000 genomic particles per cell of the indicated mutant. Percentage of transduced cells was measured using flow cytometry.

Figure 8:
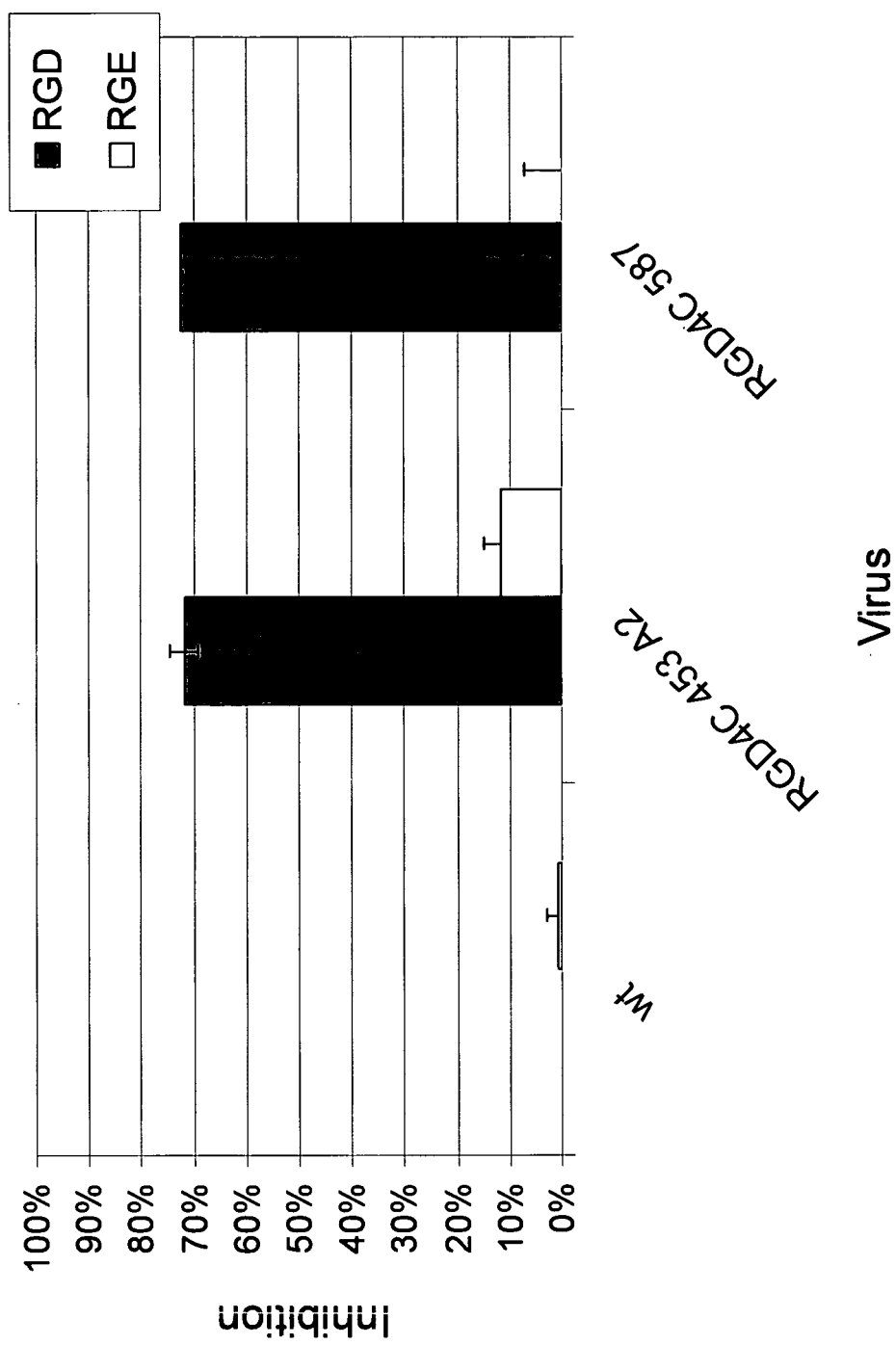

FIG. 8: Competition of transduction with soluble peptide

Transduction of CHO(HSPG KO) cells was performed with indicated virions 24 h after seeding the cells. Medium was removed. ½ vol. of medium was given to the well containing competition peptide (600 μM) or, as in the case of the controls, just medium. After 15 min of incubation at RT ½ medium containing virus was given to the cells. MOI=1.000 genomic particles per cell. 48 h after transduction GFP expression was measured by flow cytometry.

Figure 9:
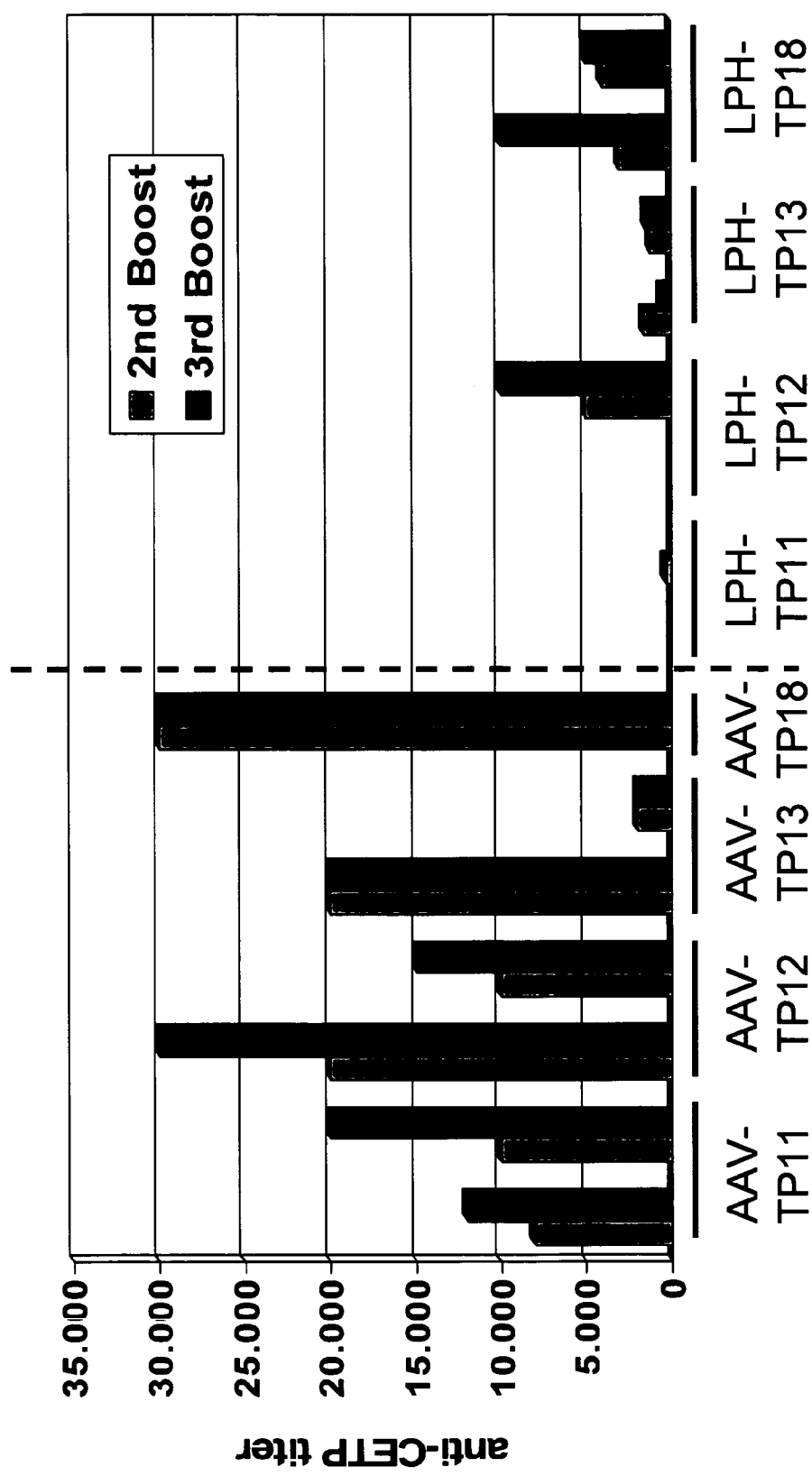

FIG. 9: Induction of auto-antibodies by AAV-based vaccines vs. peptide based vaccines Rabbits (n=2) were immunized with the AAV-based CETP vaccines AAV-TP11, AAV-TP12, AAV-TP13 or AAV-TP18 s.c. in the presence of an adjuvant. AAV-based CETP vaccines were compared with the corresponding peptide vaccines containing the same epitope coupled to LPH (*Limulus polyphemus* hemocyanine). The titer of CETP auto-antibodies in the immune sera was measured after the $2^{nd}$ (gray) and $3^{rd}$ (black) boost immunization.

Figure 10:
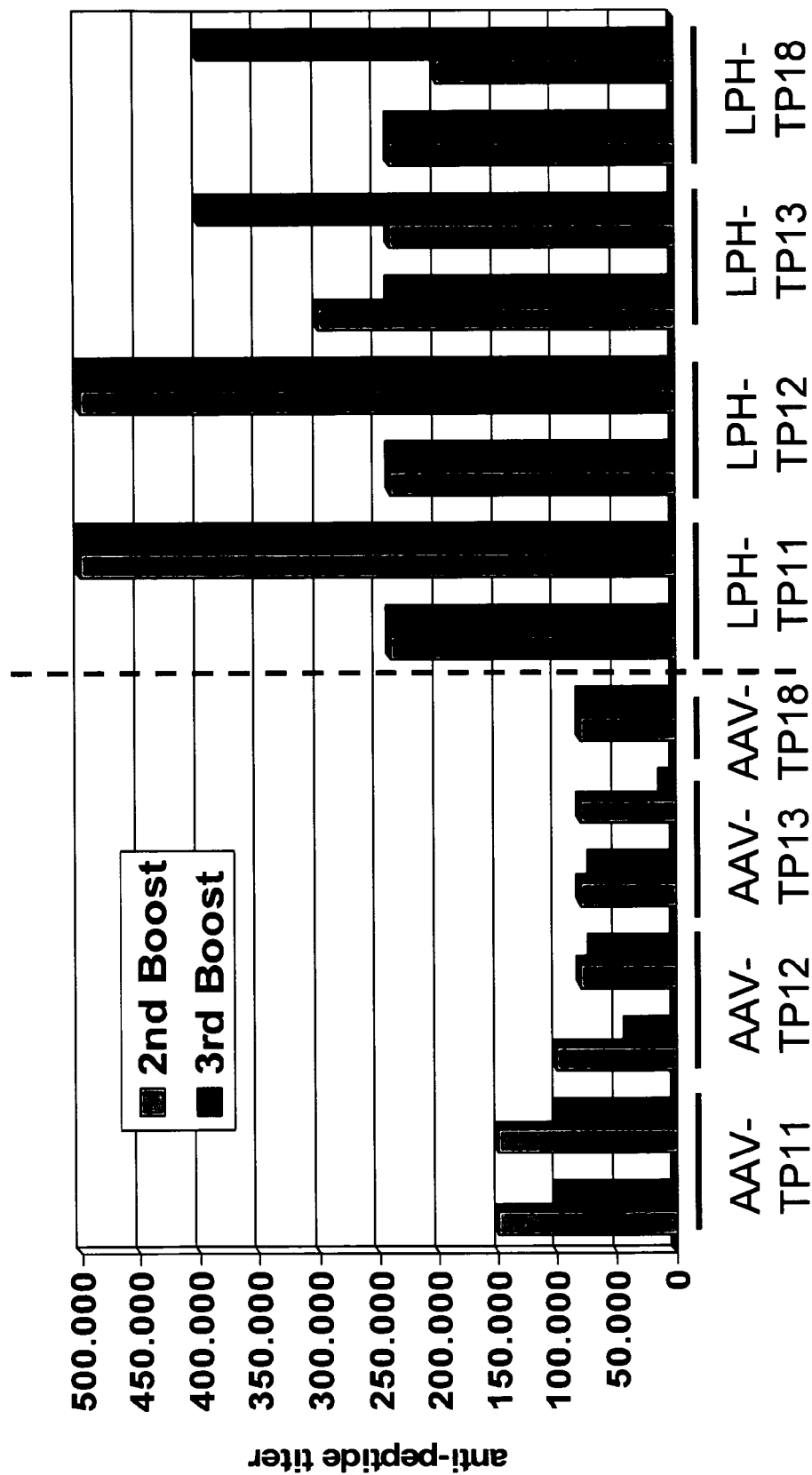

FIG. 10: Induction of auto-antibodies by AAV-based vaccines vs. peptide based vaccines Rabbits (n=2) were immunized with the AAV-based CETP vaccines AAV-TP11, AAV-TP12, AAV-TP13, or AAV-TP18 s.c. in the presence of an adjuvant. AAV-based CETP vaccines were compared with the corresponding peptide vaccines containing the same epitope coupled to LPH (*Limulus polyphemus* hemocyanine). The titer of auto-antibodies directed against the epitope (linear peptide) in the immune sera was measured after the $2^{nd}$ (gray) and $3^{rd}$ (black) boost immunization.

Figure 11:
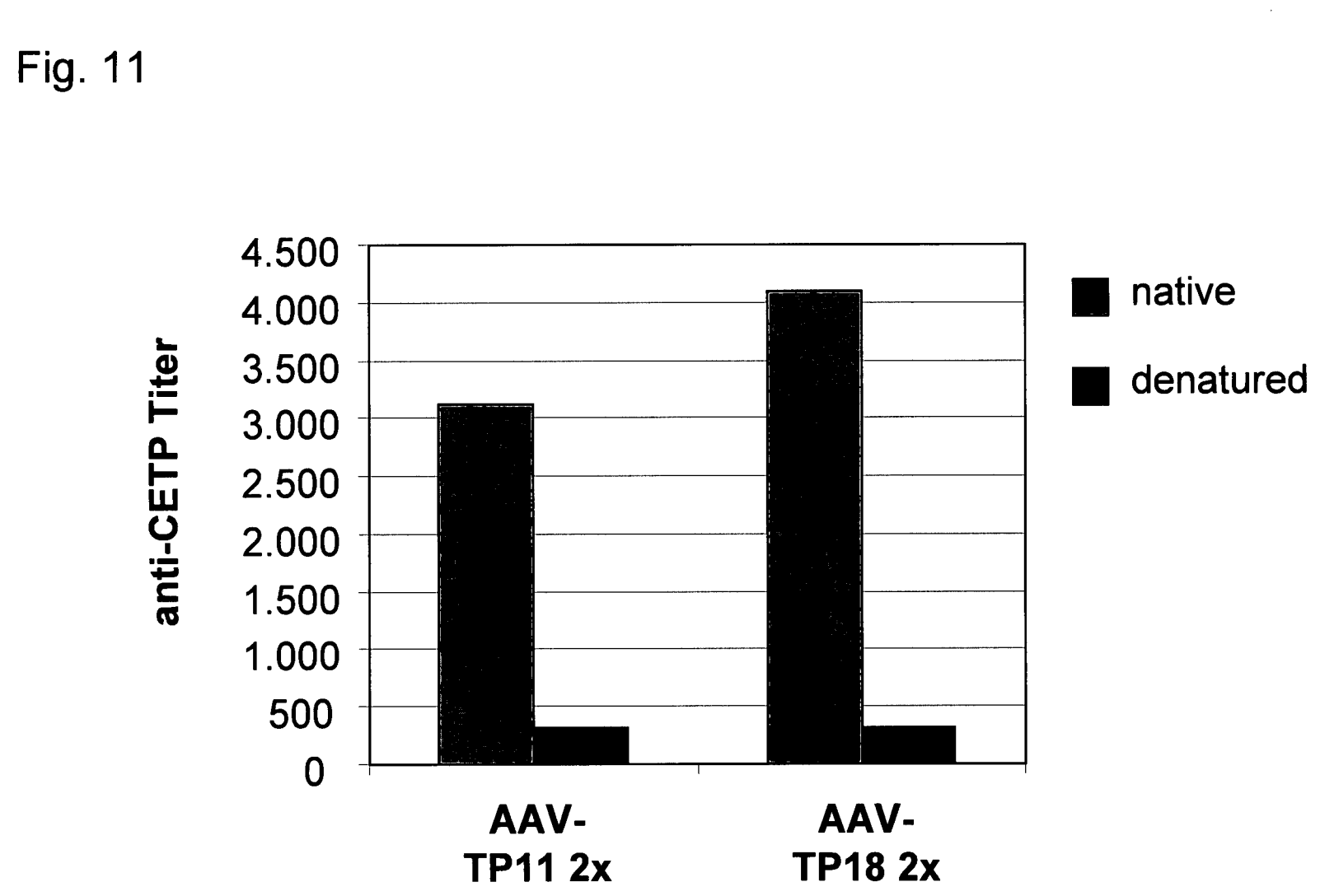

FIG. 11: Induction of auto-antibodies by native and heat-denatured AAV-based vaccines Rabbits (n=4) were immunized with native (gray) or heat-denatured (black) AAV-based CETP vaccines AAV-TP11 2× or AAV-TP18 2× s.c. in the presence of an adjuvant. The titer of CETP auto-antibodies in the immune sera was measured after the $1^{st}$ boost immunization.

Figure 12:
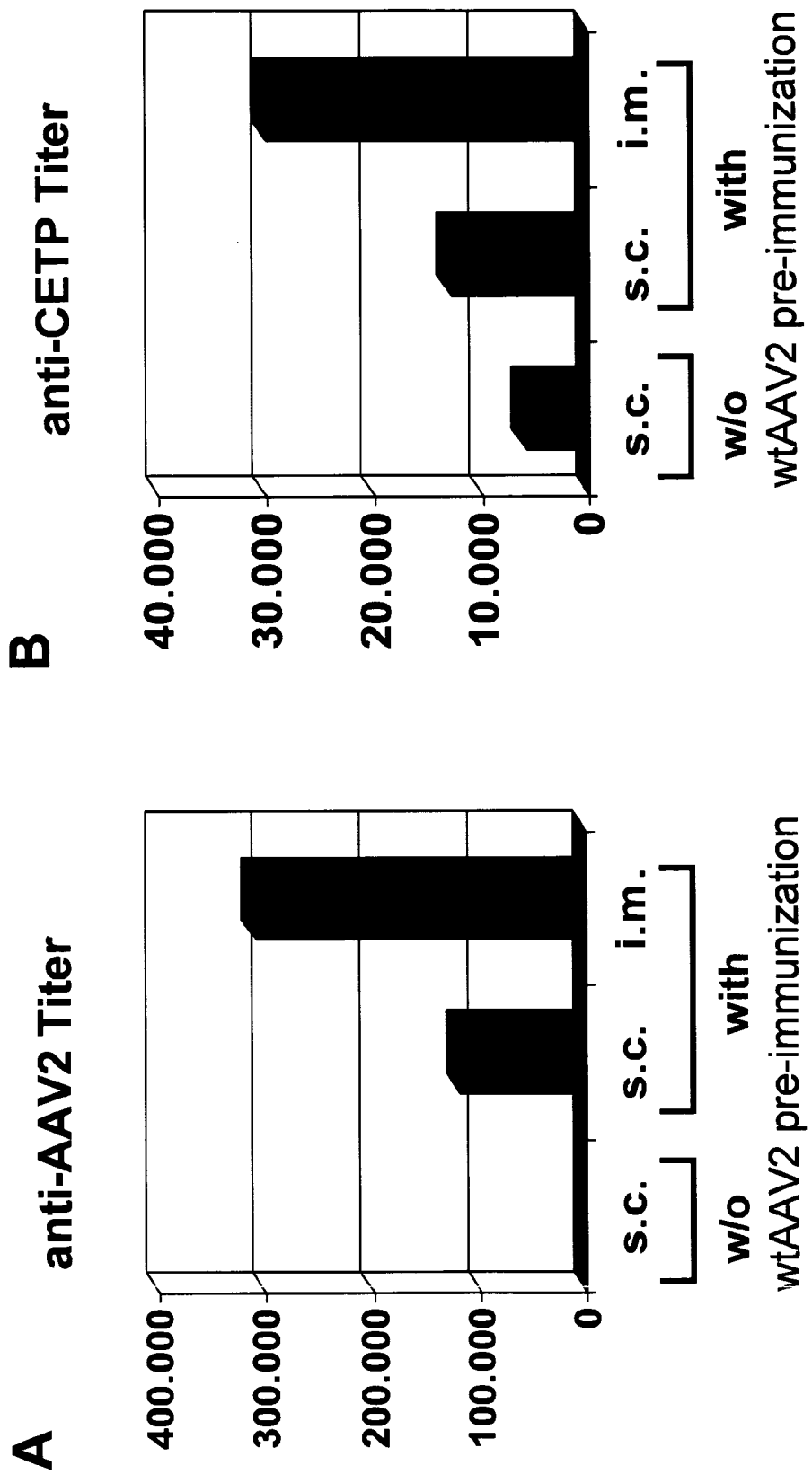

FIG. 12: Evaluation of the impact of anti-AAV2 antibodies on immunization with AAV2-based vaccines (A) To evaluate the impact of anti-AAV2 antibodies on the immunization success of AAV2-based vaccines, rabbits (n=3) were pre-immunized by two applications of 4.5 μg wtAA2 (s.c. or i.m.). Serum was analyzed two weeks after $2^{nd}$ application for the level of anti-AAV2 antibodies. A control group (n=2) was not pre-immunized with wtAAV2.

(B) Following pre-immunization with wtAAV2 rabbits were vaccinated with the AAV2-based vaccine AAV-TP18 (7.2 μg per application). The vaccine was administered s.c. or i.m. in the presence of an adjuvant. Sera were analyzed two weeks after the $1^{st}$ boost vaccination for the level of CETP auto-antibodies. Results were compared to vaccination (s.c.) of animals without wtAAV2 pre-immunization.

Figure 13:
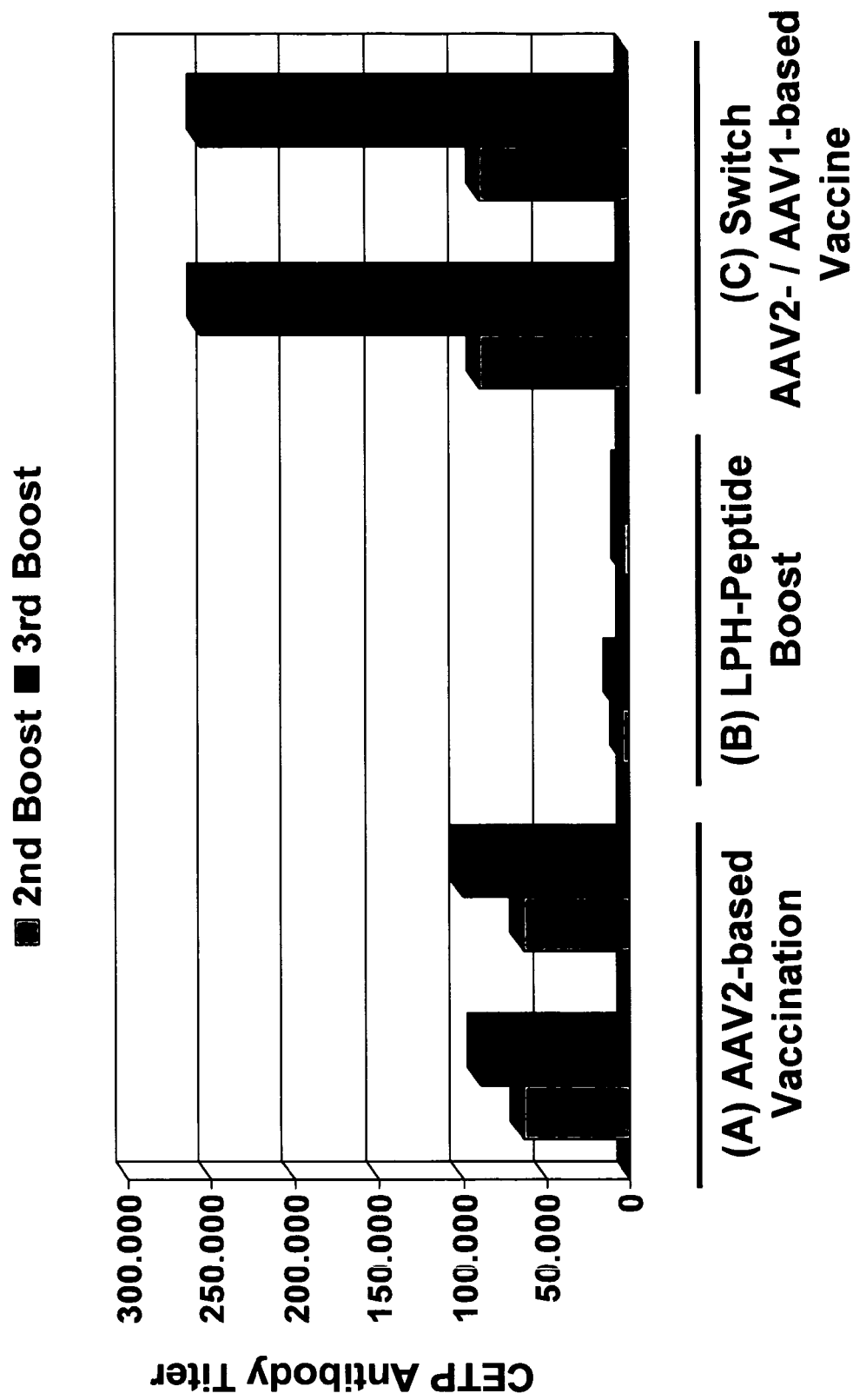

FIG. 13: Evaluation of different prime/boost regimens for AAV-based vaccines

Three different prime/boost regimens were evaluated. Group A received one prime and three boost applications of AAV2-CETin-2× (AAV2-based vaccination). Group B received one prime and one boost immunization with AAV2-CETin-2× followed by two boost immunizations with the LPH-coupled CETP-intern peptide (LPH-peptide boost). Group C received one prime and one boost immunization with AAV2-CETIn-2× followed by two boost immunizations with AAV1-CETin (switch AAV2-/AAV1-based vaccine). Immune sera were analyzed for anti-CETP-reactivity (CETP auto-antibody titer) two weeks after the $2^{nd}$ (gray) and $3^{rd}$ boost (black) immunization.

Figure 14:
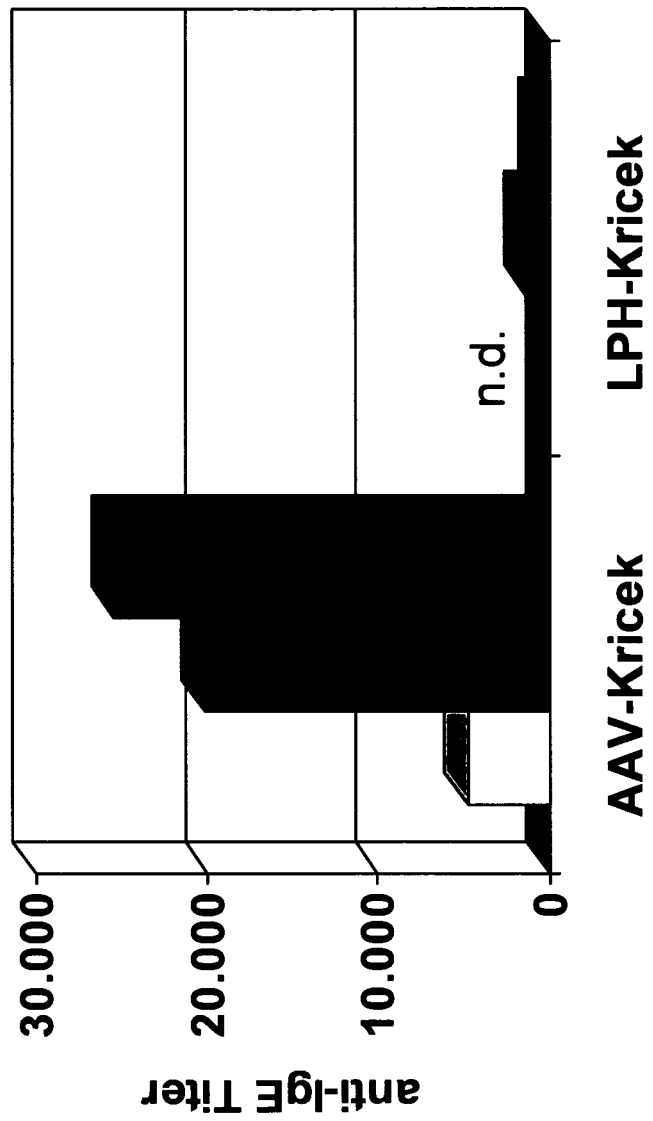

FIG. 14: Vaccination against human IgE

Rabbits (n=2) were immunized with AAV2 particles carrying a human IgE epitope ("Kricek") at position I-587. In a control group rabbits were immunized with the same IgE epitope coupled to LPH (LPH-Kricek). Immune sera were analyzed for anti-IgE reactivity two weeks after the $1^{st}$ (white), $2^{nd}$ (gray) and $3^{rd}$ (black) boost immunization. n. d.: not determined.

EXAMPLES

The following examples exemplify the invention for AAV, especially for AAV2. Due to the general similarities within the structures of the adeno-associated viruses and other parvoviruses the invention can be easily transferred to other parvoviruses.

1. Generation of Modified AAV Variants by Insertion of Epi- or Mimotope Sequences at Position I-453 of the AAV Capsid by Genetic Manipulation The approach described below is used for the insertion of epi- or mimotopes into the AAV capsid at position I-453 using a defined cloning strategy. This strategy includes the generation of a NotI and AscI restriction site within the cap gene by site-directed mutagenesis that allows the insertion of DNA fragments encoding epi- or mimotope at position I-453 of AAV cap flanked by a short or long alanine adaptor sequence.

1.1. Creation of Singular NotI and AscI Restriction Sites in Vector pCI-VP2

The vector pCI-VP2 was created by PCR amplification of the AAV2 VP-2 gene mutating the minor ACG start codon into an ATG and cloning of the respective PCR product into the polylinker sequence of pCI (PROMEGA). The NotI site at nucleotide 18 of pCI-VP2 (nucleotide 1099 of pCI) was destroyed by site directed mutagenesis using the primers

```
mutashe-3
                                        (SEQ ID NO: 44)
5'-GAG TCG ACC CGG GCA GCC GCT TCG AGC-3'
and mutashe-4
                                        (SEQ ID NO: 45)
5'-GCT CGA AGC GGC TGC CCG GGT CGA CTC-3'
``` together with the QUICKCHANGE II SITE-DIRECTED MUTAGENESIS KIT (STRATAGENE) according to the instructions of the manufacturer. The resulting vector was referred to as pCI-VP2-ΔNot18. To introduce a NotI and AscI restriction site that allows for the cloning of epitope or mimotope sequences at position I-453 of the AAV capsid, the vector pCI-VP2-ΔNot18 was modified by site directed mutagenesis using the primers

```
mutashe-5
                                        (SEQ ID NO: 46)
5'-CA AAC ACT CCA AGT GGA GGG CGC GCC GCT ACC
ACC ACG CAG TC-3'
and mutashe-6
                                        (SEQ ID NO: 47)
5'-GA CTG CGT GGT GGT AGC GGC GCG CCC TCC ACT
TGG AGT GTT TG-3'
``` to introduce the AscI site first as well as the primers

```
mutashe-7
                                        (SEQ ID NO: 48)
5'-CA AAC ACT CCA AGT GGA GCG GCC GCA GGG CGC
GCC GCT AC-3'
and mutashe-8
                                        (SEQ ID NO: 49)
5'-GT AGC GGC GCG CCC TGC GGC CGC TCC ACT TGG
AGT GTT TG-3'
``` to introduce the NotI site subsequently.

Site specific mutagenesis was performed using the QUIKCHANGE II SITE-DIRECTED MUTAGENESIS KIT (STRATAGENE) according to the instructions of the manufacturer. The resulting vector is referred to as pCIVP2-I453-NotI-AscI.

1.2. Cloning of Epitope or Mimotope Sequences into pCIVP2-I453-NotI-AscI

For cloning of epi- or mimotope sequences into pCIVP2-I453-NotI-AscI, forward and reverse oligonucleotides were designed that encode the respective epi- or mimotope sequences with a short or long alanine adaptor sequence and contain a 5'-site extension. The 5'-site extension of the oligonucleotides was designed so that annealing of the forward and reverse oligonucleotides results in a dsDNA with 5'-site and 3'-site overhangs compatible with overhangs generated by NotI and AscI restriction of the plasmid pCIVP2-I453-NotI-AscI. The sequences of the oligonucleotides and the respective epi- or mimotope sequences including the alanine adaptors are summarized in Table 8. Each of the inserted epi- or mimotope sequences is flanked by a short or long adaptor according to the following scheme ($X_n$ represents the mimotope or epitope sequence):

short Ala adaptor: $(A)_3$-$X_n$-R-$(A)_2$ (A short)

long Ala adaptor: $(A)_5$-$X_n$-$(A)_2$-R-$(A)_2$ (A long)

long Gly adaptor: $(A)_2$-$(G)_5$-$X_n$-$(G)_5$-R-$(A)_2$ (G long)

TABLE 8

Oligonucleotides used for cloning of epi- or mimotope sequences at position I-453

| Name/<br>Peptide Seq. | Type | Forward Oligonucleotide | Reverse Oligonucleotide | Adaptor |
|---|---|---|---|---|
| Kricek<br>VNLTWSRASG<br>SEQ ID NO: 50 | Epitope | 5'-ggccgcagtgaacctgac<br>ctggagcagagcctccggc-3'<br>SEQ ID NO: 51 | 5'-cgcggccggaggctctgct<br>ccaggtcaggttcactgc-3'<br>SEQ ID NO: 52 | A short |
| | | 5'-ggccgcagccgcagtgaa<br>cctgacctggagcagagcctcc<br>ggcgcggca-3'<br>SEQ ID NO: 53 | 5'-cgcgtgccgcgccggag<br>gctctgctccaggtcaggttcact<br>gcggctgc-3'<br>SEQ ID NO: 54 | A long |

TABLE 8-continued

Oligonucleotides used for cloning of epi- or mimotope sequences at position I-453

| Name/ Peptide Seq. | Type | Forward Oligonucleotide | Reverse Oligonucleotide | Adaptor |
|---|---|---|---|---|
| Rudolf EFCINHRGYW VCGD SEQ ID NO: 55 | Mimotope | 5'-ggccgcagaattctgcata aaccacaggggatactgggtgt gcggagac-3' SEQ ID NO: 56 | 5'-cgcggtctccgcacaccc agtatcccctgtggtttatgcaga attctgc-3' SEQ ID NO: 57 | A short |
| | | 5'-ggccgcagccgcagaattc tgcataaaccacaggggatact gggtgtgcggagacgcggca-3' SEQ ID NO: 58 | 5'-cgcgtgccgcgtctccgca cacccagtatcccctgtggtttat gcagaattctgcggctgc-3' SEQ ID NO: 59 | A long |
| CETP-intern CDAGSVRTNA PD SEQ ID NO: 60 | Epitope | 5'-ggccgcatgcgacgctgg cagtgtgcgcaccaatgcacca gac-3' SEQ ID NO: 61 | 5'-cgcggtctggtgcattggtg cgcacactgccagcgtcgca tgc-3' SEQ ID NO: 62 | A short |
| | | 5'-ggccgcagccgcatgcga cgctggcagtgtgcgcaccaat gcaccagacgcggca-3' SEQ ID NO: 63 | 5'-cgcgtgccgcgtctggtgc attggtgcgcacactgccagc gtcgcatgcggctgc-3' SEQ ID NO: 64 | A long |
| β-amyloid DAEFRHDSG SEQ ID NO: 65 | Epitope | 5'-ggccggcggaggcggtgg ggacgccgaattcagacacga cagcggcggaggcggtggag gg-3' SEQ ID NO: 66 | 5'-cgcgccctccaccgcctcc gccgctgtcgtgtctgaattcgg cgtccccaccgcctccgcc-3' SEQ ID NO: 67 | G long |

To anneal the oligonucleotides 50.0 μg of the forward oligonucleotide and 50.0 μg of the reverse oligonucleotide were mixed in a total volume of 200 μl 1×PCR-Buffer (QIAGEN) and incubated for 3 min at 95° C. in a thermomixer. After 3 min at 95° C. the thermomixer was switched off and the tubes were left in the incubator for an additional 2 h to allow annealing of the oligonucleotides during the cooling down of the incubator. To clone the annealed oligonucleotides into pCIVP2-I453-NotI-Asci the vector was linearized by restriction with NotI and AscI and the cloning reaction was performed using the Rapid DNA Ligation Kit (Roche). Briefly, the annealed oligonucleotides were diluted 10-fold in 1×DNA Dilution Buffer and incubated for 5 min at 50° C. 100 ng of these annealed oligonucleotides and 50 ng of the linearized vector pCIVP2-I453-NotI-AscI were used in the ligation reaction, which was performed according to the instructions of the manufacturer of the Rapid DNA Ligation Kit (Roche). E. coli XL1 blue were transformed with an aliquot of the ligation reaction and plated on LB-Amp agar plates. Plasmids were prepared according to standard procedures and were analyzed by sequencing.

1.3. Subcloning of Epitope or Mimotope Sequences from pCIVP2 into pUCAV2

For production of recombinant AAV particles carrying a mimo- or epitope insertion at position I-453 the BsiWI/XmaI fragment of pCI-VP2-453-NotI-AscI encoding a VP-2 fragment containing the epitope or mimotope at position I-453 was sub-cloned into pUCAV2, which was modified as described below.

Cloning of vector pUCAV2 is described in detail in U.S. Pat. No. 6,846,665. Basically, this vector contains the complete AAV genome (Bgl II fragment) derived from pAV2 (Laughlin et al., 1983) cloned into BamHI of pUC19.

pUCAV2 is used for production of the modified AAV particles. Since there are three XmaI sites in pUCAV2 it is not possible to use the XmaI site of pUCAV2 for subcloning of the BsiWI/XmaI fragment of pCI-VP2-453-NotI-AscI. Therefore, a new AgeI site was introduced into pUCAV2 that is compatible with XmaI and is not present in pUCAV2. To introduce the AgeI site pUCAV2 was linearized by SnaBI, dephosphorylated and subsequently blunt-end ligated with a short ds oligonucleotide adaptor containing an internal AgeI site. The ds oligonucleotide adaptor was generated by annealing of a sense
(SEQ ID NO: 68)
5'-GTA GCC CTG GAA ACT AGA ACC GGT GCC TGC GCC-3'
and anti-sense
(SEQ ID NO: 69)
5'-GGC GCA GGC ACC GGT TCT AGT TTC CAG GGC TAC-3' oligonucleotide containing an AgeI restriction site as described above. The annealed oligonucleotides were ligated with the SnaBI linearized, dephosphorylated pUCAV2 using the Rapid DNA Ligation Kit (Roche) as described above. The resulting vector is referred to as pUCAV2-AgeI. pUCAV2-AgeI was linearized with BsiWI and AgeI and ligated with the BsiWI/XmaI fragment of pCI-VP2-453-NotI-AscI encoding the VP-2 fragment containing the respective epitope or mimotope at position I-453.

2. Generation of Modified AAV Variants by Insertion of Epitope Sequences at Position I-587 of the AAV Capsid by Genetic Manipulation The approach described below is used for the insertion of epi- or mimotopes into the AAV capsid at position I-587 using a defined cloning strategy. This strategy includes the generation of a NotI and AscI restriction site within the cap gene by site-directed mutagenesis that allows the insertion of DNA fragments encoding epi- or mimotope at position I-587 of AAV cap flanked by a short or long alanine adaptor sequence.

2.1. Creation of Singular NotI and AscI Restriction Sites in Vector pCI-VP2 at Insertion site I-587

The vector pCI-VP2 was created by PCR amplification of the AAV2 VP-2 gene mutating the minor ACG start codon into an ATG and cloning of the respective PCR product into the polylinker sequence of pCI (PROMEGA). The NotI site at nucleotide 18 of pCI-VP2 (nucleotide 1099 of pCI) was destroyed by site-directed mutagenesis as described above. The resulting vector was referred to as pCI-VP2-ΔNot18. To introduce a NotI and AscI restriction site that allows for the cloning of epitope or mimotope sequences at position I-587 of the AAV capsid, the vector pCI-VP2-ANot18 was modified by site-directed mutagenesis using the primers

```
pCI-VP2-ΔNot-I587-for
                                        (SEQ ID NO: 70)
5'-CC AAC CTC CAG AGA GGC AAC GCG GCC GCA AGG CGC GCC AAG CAG CTA CCG CAG-3'
and pCI-VP2-ΔNot-I587-rev
                                        (SEQ ID NO: 71)
5'-CTG CGG T -continued Xbal-VAlI-1200-5'
SEQ ID NO: 79
5'-TCT AGA GCA AAA AAG GGG CTC GTC CCT GTT TCC-3', cloned into pTOPO and then subcloned into the XbaI site of pUCAdvE2/E4. The resulting plasmid pUCAdvE2/E4-VAI-VAII was evaluated in co-transfection experiments for production of AAV as described below. AAV particle formation was analyzed using the A20 ELISA.

3.2. Production of AAV Variants by Co-Transfection of HEK 293-T-Cells

For production of AAV particles HEK 293-T cells were co-transfected with the vector plasmid pUCAV2 containing the subcloned epitope (in I-453 and/or I-587) and the helper plasmid pUCAdV (described above).

For co-transfection $7.5 \times 10^6$ 293-T cells were seeded into each 015 cm cell culture plate in a total volume of 17.5 ml medium (DMEM containing 10% FCS, 5 mM L-Gln and ABAM) 24 h before transfection and cultivated at 37° C., 5% CO, in a humidified atmosphere. For co-transfection of the vector plasmid pUCAV2 containing the epitope (in I-453 or I-587) and pUCAdV a molar ratio of the plasmids of 1:1 was chosen. For Calcium phosphate transfection of one culture plate with 293-T cells using the Calcium phosphate transfection protocol as disclosed in US 2004/0053410, 12.0 µg pUCAV2 (containing the epitope in I-453 or I-587) and 24.0 µg pUCAdV were mixed in 875 µl 270 mM $CaCl_2$. In brief, 875 µl 2×BBS (50 mM BES (pH 16.95), 280 mM NaCl and 1.5 mM $Na_2HPO_4$) was added to the mixture and the resulting solution was carefully mixed by pipetting. The solution was incubated for 20 min at room temperature and then added drop-wise to the cell culture plate. Cells were incubated at 35° C., 3% $CO_2$ in a humidified atmosphere for 18 h. After 18 h at 35° C. and 3% $CO_2$ cells were cultivated for an additional 3d at 37° C., 5% $CO_2$ in a humidified atmosphere.

293-T cells were harvested with a cell lifter, transferred into 50 ml plastic tubes (Falcon) and centrifuged at 3000 g at 4° C. for 10 min. The cell pellet was resuspended in 1.0 ml lysis buffer (150 mM NaCl, 50 mM Tris, pH 8.5) and objected to three rounds of freeze and thaw cycles. The lysate was treated with 100 U/ml benzonase (MERCK) at 37° C. for 30 min. The cell lysate was cleared by two centrifugation steps (3700 g, 4° C., 20 min) and the AAV-containing supernatant was used for further purification.

The AAV capsid titer of the lysate was determined using a commercially available ELISA (AAV Titration ELISA, PROGEN).

3.3. Purification of AAV Particles by Density Gradient Centrifugation Using Iodixanol AAV particles were purified by iodixanol gradient centrifugation. The virus-containing cell lysate was cleared by centrifugation (3700 g, 4° C., 20 min) and the cleared lysate was transferred to QICKSEAL ultracentrifugation tubes (26×77 mm, BECKMAN). Iodixanol solutions (SIGMA) of different concentrations were layered beneath the virus containing lysate. By this an Iodixanol gradient was created composed of 6.0 ml 60% on the bottom, 5.0 ml 40%, 6.0 ml 25% and 9.0 ml 15% Iodixanol with the virus solution on top. The gradient was spinned in an ultracentrifuge at 416.000 g for 1 h at 18° C. The 40% phase containing the AAV particles was then extracted with a cannula by puncturing the tube underneath the 40% phase and allowing the solution to drip into a collecting tube until the 25% phase was reached. The AAV capsid titer of the 40% phase was determined using a commercially available ELISA (AAV Titration ELISA, PROGEN).

4. AAV Variants Carrying a CETP Epitope at Position I-453 or I-587 of the AAV2 Capsid An epitope (CDAGSVRTNAPD; SEQ ID NO: 60) of rabbit CETP (cholesteryl ester transfer protein) was introduced at position I-453 or I-587 of AAV2 by the cloning approaches described above. In both insertion sites the epitope is flanked by a short or long alanine adaptor. For production of AAV variants HEK 293-T cells were co-transfected with the vector plasmid pUCAV2 containing the subcloned CETP epitope sequence at position I-453 or I-587, and the helper plasmid pUCAdV as described above. AAV variants were purified by Iodixanol gradient centrifugation as described above.

The AAV capsid variants AAV-CETP-453-short, AAV-CETP-453-long, AAV-CETP-587-short and AAV-CETP-587-long were analyzed by dot blot experiments (FIG. 4). $5\times10^{10}$ or $1\times10^{10}$ purified AAV particles AAV-CETP-453-short and AAV-CETP-453-long were spotted onto a nitrocellulose membrane using a vacuum device. Likewise, $5\times10^{10}$ purified AAV particles AAV-CETP-587-short and AAV-CETP-587-long were spotted onto the same membrane. As negative control wtAAV was spotted ranging from $5.0\times10^{10}$ to $6.3\times10^9$ capsids per dot. After blocking of the membrane with blocking buffer (5% milk powder in PBS containing 0.05% Tween-20), the membrane was incubated with a polyclonal anti-CETP serum generated by immunizing rabbits with the CETP epitope coupled to KLH. After washing of the membrane with PBS/0.05% Tween-20, binding of the anti-CETP antibodies to the spotted AAV variants was detected with an anti-rabbit IgG HRP conjugate (CALTAG). After washing, signals were detected by chemiluminescence using the ECL system (AMERSHAM BIOSCIENCE).

The result demonstrate that there is a specific detection of the CETP epitope inserted into the AAV capsid at position I-453 or I-587 by the respective CETP antibody demonstrating that the epitope is displayed on the surface of the AAV particle.

5. Double Insertion of a β-Amyloid Epitope at Position I-453 and I-587 of the AAV Capsid The cloning approach described below is used for the double insertion of an epi- or mimotope sequence into the AAV capsid at position I-453 and I-587 using a defined cloning strategy.

5.1. Insertion of an FseI Restriction Site into pCIVP2

An FseI restriction site was inserted into the vectors pCIVP2-1587-Not-AscI and pCIVP2-I453-NotI-AscI located between I-453 and I-587 by site-directed mutagenesis using the QUIKCHANGE II SITE-DIRECTED MUTAGENESIS KIT (STRATAGENE) and the oligonucleotides

```
mutashe-9
                                       (SEQ ID NO: 80)
5'-GGT GAA TCC GGG GCC GGC CAT GGC AAG C-3'
and mutashe-10
                                       (SEQ ID NO: 81)
5'-GCT TGC CAT GGC CGG CCC CGG ATT CAC C-3'.
```

5.2. Cloning of a β-Amyloid Epitope at Position I-587 of pUCAV2

The β-amyloid epitope DAEFRHDSG (SEQ ID NO: 65) (aa 1-9 of human β-amyloid) was cloned into the NotI/AscI restriction site of the vector pCIVP2-1587-NotI-AscI (modified as described in 5.1) using the sense and anti-sense oligonucleotides

```
β-amyloid-for
                                        (SEQ ID NO: 76)
5'-GGC CGC AGG CGG AGG GGG AGG CGA CGC CGA GTT CAG ACA CGA CAG CGG CGG CGG AGG GGG AGG CGC GG-3'
and β-amyloid-rev
                                        (SEQ ID NO: 77)
5'-CGC GCC GCG CCT CCC CCT CCG CCG CCG CTG TCG

TGT CTG AAC TCG GCG TCG CCT CCC CCT CCG CCT GC-3'
```

The oligonucleotides encode the β-amyloid epitope with a glycine adaptor sequence:

```
                                        (SEQ ID NO: 82)
        (A)₃-(G)₅-DAEFRHDSG-(G)₅-(A)₂
```

Cloning was performed as described above (2.2).

The BsiWI/XmaI fragment of pCI-VP2-587-NotI-AscI encoding a VP-2 fragment containing the β-amyloid epitope at position I-587 was sub-cloned into pUCAV2-AgeI as described above (2.3). The resulting vector was referred to as pUCAV2-amyloid-587

5.3. Cloning of a β-Amyloid Epitope at Position I-453 of pCIVP2

The β-amyloid epitope (DAEFRHDSG, SEQ ID NO: 65) was cloned into the NotI/AscI restriction site at the insertion site I-453 of the vector pCIVP2-I453-NotI-AscI (modified as described in 5.1) using the sense and anti-sense oligonucleotides

```
Amyloid 453for
                                        (SEQ ID NO: 66)
5'-G GCC GGC GGA GGC GGT GGG GAC GCC GAA TTC

AGA CAC GAC AGC GGC GGA GGC GGT GGA GGG-3'

Amyloid 453rev
                                        (SEQ ID NO: 67)
5'-C GCG CCC TCC ACC GCC TCC GCC GCT GTC GTG

TCT GAA TTC GGC GTC CCC ACC GCC TCC GCC-3'
```

The oligonucleotides encode the β-amyloid epitope with a glycine adaptor sequence:

```
                                        (SEQ ID NO: 83)
        (A)₂-(G)₅-DAEFRHDSG-(G)₅-R-(A)₂
```

Cloning was performed as described above (1.2).

5.4. Cloning of a β-Amyloid Epitope at Position I-453 and I-587 of pUCAV2

For production of recombinant AAV particles carrying the β-amyloid epitope at position I-587 and I-453, the vector pUCAV2-amyloid-587 was cut with BsiW/FseI and ligated with the 0.6 kb BsiW/FseI fragment of pCI-VP-453-NotI-AscI. The BsiW/FseI fragment of pCI-VP2-453-NotI-AscI encodes the VP-2 fragment containing the β-amyloid epitope at position I-453. The resulting vector was referred to as pUCAV2-amyloid-453-587.

5.5. Production, Purification and Evaluation of Aav Particles Carrying a β-Amyloid Epitope at I-453 and I-587

For production of recombinant AAV particles carrying the β-amyloid epitope at position I-587 and I-453, 293 cells were transfected with the vector pUCAV2-amyloid-453-587 and the helper plasmid pUCAdV as described above (3.2 and 3.3). The corresponding AAV particles were referred to as AAV-amyloid-453-587.

For production of recombinant AAV particles carrying the β-amyloid epitope at position I-587, 293 cells were transfected with the vector pUCAV2-amyloid-587 and the helper plasmid pUCAdV as described above. The corresponding AAV particles were referred to as AAV-amyloid-587. All AAV particles were purified as described above To evaluate the expression of the β-amyloid epitope at the surface of the AAV capsid, serial dilutions of purified AAV particles AAV-amyloid-453-587 and AAV-amyloid-587 were dotted on a membrane (FIG. 5). As a negative control AAV particles carrying a CETP epitope at position I-587 were dotted. As a positive control a β-amyloid peptide (aa 1-42) (BIOSOURCE) was dotted. After blocking of the membrane with blocking buffer (5% milk powder in PBS containing 0.05% Tween-20), the β-amyloid epitope was detected using an anti-β-amyloid mAb 6E10 (CHEMICON) (FIG. 5). The anti-β-amyloid mAb was used at a concentration of 1.0 µg/ml in PBS/1% milk powder/0.05% Tween-20. Binding of the anti-β-amyloid mAb was detected using a peroxidase labeled anti-mouse IgG antibody (CALTAG). After washing, signals were detected by chemiluminescence using the SUPERSIGNAL WEST PICO CHEMILUMINESCENT SUBSTRATE (PIERCE).

These data demonstrate that the double insertion of the epitope into the insertion sites I-453 and I-587 resulting in higher epitope density at the capsid surface than the singular insertion of the epitope at position I-587 leads to an at least 2 fold higher affinity of the double insertion mutant to the β-amyloid antibody as compared to the I-587-insertion mutant alone.

6. Generation of Modified AAV2 Variants by Insertion of a $\alpha_v\beta_3$ Integrin Targeting Sequence at Position I-453 of the AAV Capsid by Genetic Manipulation 6.1. Determination of Titers In order to generate a number of insertion mutants that target the $\alpha_v\beta_3$ and $\alpha_v\beta_5$ integrins, the targeting peptide RGD-4C with its sequence (SEQ ID NO: 84)

ACDCRGDCFCA was inserted between $G_{453}$ and $T_{454}$ of AAV2 structural proteins VP-1, VP-2 and VP-3 of AAV2 (mutant named RGD4C 453). This targeting insertion was further combined with the two point mutations $R_{585}A$ and $R_{588}A$ in order to diminish binding to AAV2's natural receptor HSPG (named RGD4C 453 A2). The identical targeting peptide was inserted into the previously described insertion site I-587 (named RGD4C 587) and the corresponding $R_{585}A/R_{588}A$ mutant (named RGD4C 587 A2). Further, the identical targeting peptide was inserted into both insertion sites I-453 and I-587 (named RGD4C 453 & 587) and the corresponding $R_{585}A/R_{588}A$ mutant (named RGD4C 453 & 587 A2).

All mutants were generated by site-direct mutagenesis used to package scGFP and titrated as follows: 293 cells were seeded at 80% confluence and co-transfected by calcium phosphate with a total of 37.5 μg vector plasmid pAAV/EGFP, packaging helper plasmid (coding for Rep and Cap), and adenoviral plasmid pXX6 (Xiao et al., 1998) at a 1:1:1 ratio. 48 h after transfection, cells were harvested and pelleted by low-speed centrifugation. Cells were resuspended in 150 mM NaCl, 50 mM Tris-HCl (pH 8.5), freeze-thawed several times, and treated with Benzonase for 30 min at 37° C. Cell debris was spun down at 3.700 g for 20 min at 4° C. Supernatant was loaded onto a discontinuous iodixanol gradient. 40% phase containing the vector was harvested and titered.

Genomic titers of vector stocks were determined by quantitative PCR (Theiss et al., 2003). For this, viral DNA was isolated from vector stocks according to the DNeasy kit protocol (QIAGEN).

The capsid titers of vector stocks were determined by A20 ELISA as previously described (Girod et al., 1999).

Transducing titers were determined transducing HeLa cells with the respective AAV mutant or wild-type expressing scGFP. Transduced cells were then counted by standard FACS analysis. In brief, $7 \times 10^4$ HeLa cells were seeded into each well of a 12-well-plate and incubated for 24 h. Serial dilutions of the respective virus were added to the cells and incubated for 48 h at 37° C. and 5% $CO_2$. Cells were trypsinized, transferred into FACS tubes and analyzed by standard conditions by flow cytometry (FACS Becton-Dickinson) in order to calculate the amount of transducing particles per ml.

The amount of capsid per genomic particles in each viral preparation showed, by comparison with wild-type, that all mutants assembled capsids and packaged efficiently viral genomes (Table 10, columns Cap/ml and GenP/ml). Determination of transducing particles (tP) is dependent on all steps of viral transduction including binding, uptake, lysosomal escape and activation of gene expression. All tested mutants except the two double insertions mutants AAV2 RGD4C 453 & 587 and AAV2 RGD4C 453 & 587 A2 had considerably high transducing titers of at least $10^7$ transducing particles per ml. Transducing titers of both double insertion mutants were below the detection limit although a successful cell binding could be determined.

The ratio of capsids per genomic particles provides information about packaging efficiencies and thus allows determining whether a capsid modification interferes with packaging of vector genomes into the preformed AAV capsids. All tested mutants were able to efficiently package viral genomes (Cap/GenP). Consequently, the peptide RGD4C can be successfully inserted into I-453. The tested mutants show capsid formation and efficient packaging of viral genomes.

The ratio of genomic particles per transducing particles (GenP/tP) is an indicator for the ability of a mutant containing a viral genome to successfully transduce a cell and express its reporter gene. Consequently the higher the ratio the lower is the transducing activity of the mutant for the specific cell line.

The insertion of the RGD-4C peptide in either I-453 or I-587 led, compared to wild-type, to a higher GenP/tP ratio. Therefore, the inserted targeting peptide somehow interfered with the transducing activity of HeLa cells. The two double insertion mutants AAV2 RGD4C 453 & 587 and AAV2 RGD4C 453 & 587 A2 were completely unable to transduce HeLa cells. This is surprising as $\alpha_v\beta_5$, another reported target molecule of the RGD-4C, is known to be present on HeLa cells and further is known to be an AAV2 secondary receptor (Summerford et al., 1999).

As expected, the two point mutations $R_{585}A$ and $R_{588}A$ (AAV A2 mutant) led to a 3 log reduction of transducing activity of the mutant capsids on HeLa cells. The insertion of one targeting peptide in I-453 or I-587 restored to some extent the A2 mutants ability to transduce HeLa cells, which can be explained by the fact that $\alpha_v\beta_5$ is expressed on HeLa cells and that therefore $\alpha_v\beta_5$ can compensate for the diminished HSPG binding.

TABLE 10

Titers of $a_v\beta_3$ integrin targeting
(Cap = capsids; GenP = genomic particles; tP = transducing particles)

| Virus | Cap/ml | GenP/ml | tP/ml | Cap/GenP | GenP/tP |
|---|---|---|---|---|---|
| wtAAV2 | 1.09E+13 | 7.07E+11 | 6.84E+10 | 15 | 10 |
| wtAAV2∓ | 9.50E+12 | 1.25E+12 | 4.34E+10 | 8 | 29 |
| AAV2 A2 | 1.00E+13 | 1.11E+12 | 2.75E+07 | 9 | 40364 |
| AAV2 RGD4C 453 | 1.12E+12 | 4.97E+11 | 1.63E+08 | 2 | 3049 |
| AAV2 RGD4C 453 A2 | 1.54E+12 | 6.12E+11 | 2.55E+08 | 3 | 2400 |
| AAV2 RGD4C 587 | 1.17E+12 | 4.73E+11 | 1.22E+08 | 3 | 3877 |
| AAV2 RGD4C 587 A2 | 2.83E+12 | 2.42E+11 | 6.45E+08 | 12 | 375 |
| AAV2 RGD4C 453 & 587 | 1.34E+12 | 1.55E+11 | — | 9 | — |
| AAV2 RGD4C 453 & 587 A2 | 5.02E+11 | 2.25E+11 | — | 2 | — |

6.2. Binding of Capsids to $\alpha_v\beta_3$ Integrin

The binding of AAV2 RGD-4C insertion mutants to their receptor molecule $\alpha_v\beta_3$ integrin was analyzed as previously described (Shi and Bartlett, 2003) and normalized to the amount of AAV2 particles detected by A20. In brief an ELISA plate was coated with A20 (75 ng/well, PROGEN). After blocking (PBS, 1% milk powder, 1% Tween) $1.00 \times 10^{10}$ particles were given per well. For detection of a functional RGD purified $\alpha_v\beta_3$ integrin (100 ng/well, CHEMICON) was added to the plate and detected with anti-integrin aV antibody (C-terminus/intracellular, Dil. 1:1.000, CHEMICON). For quantification of viral particles in each well biotinylated A20 (250 ng/well) was used. The ratio "anti-integrin $\alpha_v$": "A20-biot" was used for normalization of the amount of $\alpha_v\beta_3$ binding to total particles.

Both wild-type and the A2 mutant did not show any binding of $\alpha_v\beta_3$ (FIG. 6). The mutants with a single inserted targeting peptide either at I-453 or I-587 (RGD4C 453 and RGD4C 587) showed clearly detectable binding of $\alpha_v\beta_3$. Once the two arginines $R_{585}$ and $R_{588}$ were replaced by alanine, these A2 mutants showed much better binding of $\alpha_v\beta_3$ in the ELISA, whereas RGD4C 453 was even superior to RGD4C 587. The double insertion mutation RGD4C 453 & 587 also showed very good binding activity for $\alpha_v\beta_3$. The double insertion double replacement mutant RGD4C 453 & 587 A2 did not show a further increase in binding compared to RGD4C A2. However, if compared to the RGD4C 587 A2 mutant the additional insertion in I-453 clearly increased its binding activity.

Consequently, the insertion site I-453 is well suited for the insertion of peptides, as the RGD4C peptide is displayed on the surface of the capsid and is accessible to antibodies and therefore most likely to the corresponding cellular receptors. Its combination with the $R_{585}A$ and $R_{588}A$ mutations increased its binding activities approximately 50 fold suggesting that $R_{585}A$ and/or $R_{588}A$ mutants enhance the accessibility of the insert to an antibody and/or receptor.

Considering the data from example 6.1, namely that the double insert mutants AAV2 RGD4C 453 & 587 and AAV2 RGD4C 453 & 587 A2 did not show any transducing activity on HeLa cells, whereas these double insert mutants very efficiently display the peptide on the surface and strongly bind $\alpha_v\beta_3$, can be explained by the following hypothesis: (i)

there might be a difference whether or not membrane bound receptor as in example 6.1 or the soluble receptor $\alpha_v\beta_3$ in this ELISA is used. Whereas the inserted peptides are perfectly accessible to small, soluble receptors the high number of modifications on the surface of the capsid may sterically hinder the binding of a larger, membrane fixed receptor; (ii) although the double insert mutant binds to the membrane bound receptor, the uptake of the virus or the intracellular processing is hindered so that no transduction takes place. For example it is reasonable to believe that the known mechanism of endosomal acidification triggering conformational changes of the viral capsid might be impaired if epitopes are presented in a too dense fashion.

6.3. HSPG Independent Transduction

HSPG independent transduction was tested using a Chinese Hamster Ovarian (CHO) cell line with an HSPG knock-out phenotype (ATCC No.: CRL-2242) that likely expresses $\alpha_v\beta_3$ integrin as can be concluded from FIG. 8, where the addition of soluble RGD peptide inhibits transduction. Indeed, wild-type AAV2 had a very low transduction efficiency that was even reduced in the A2 mutant (FIG. 7). The insertion of the RGD-4C peptide into I-453 alone does not lead to significant transduction rates, however, if combined with the A2 point mutations (RGD4C 453 A2 in FIG. 7) transduction is even superior to I-587 insertion mutants, suggesting a conformational dependency for cell transduction.

This transduction could be inhibited by the addition of the soluble RGD peptide but only weakly by the unspecific RGE peptide (FIG. 8), demonstrating that the transduction by this mutant became RGD-4C dependent. Transduction efficiency of these CHO HSPG KO cells was increased by a factor of about four in relation to wild-type (FIG. 7).

The single insertion mutants at position I-587 (RGD4C 587 and RGD4C 587 A2) also showed an increased transduction rate compared to wild-type, but not as strong as for RGD4C 453 A2 (FIG. 7). Transduction of RGD4C 587 was also inhibited by soluble RGD peptide indicating its dependence on the RGD-4C interaction with the $\alpha_v\beta_3$ integrin.

The double insertion mutant (RGD4C 453 & 587 and RGD4C 453 & 587 A2) again were not able to efficiently transduce cells (FIG. 7) as already shown for HeLa cells (Table 10) despite efficient binding to soluble $\alpha_v\beta_3$ (FIG. 6). Again this could be explained by either steric hindrance of the too dense targeting sequences or by an inefficient uptake and/or the intracellular processing of the virus.

7. Generation of Further AAV Variants 7.1. Insertion of CETP Epitopes into the AAV2 Capsid at Position I-453

The following rabbit CETP derived epitopes were cloned into position I-453 of the AAV2 capsid using annealed oligonucleotides as described above. Each of the inserted epitope sequences in the AAV2 backbone at I-453 is flanked by the following alanine/glycine adaptors according to the following scheme (Xn represents the epitope sequence):

Type I Ala/Gly adaptor: $(Ala)_2$-$(Gly)_3$-Xn-$(Gly)_4$-Arg-$(Ala)_2$

Type II Ala/Gly adaptor: $(Ala)_3$-$(Gly)_3$-$X_n$-$(Gly)_4$-Arg-$(Ala)_2$

TABLE 11 rabbit CETP derived epitopes in I-453

| Name/ Peptide Seq. | Type | sense Oligonucleotide | anti-sense Oligonucleotide | Adaptor |
|---|---|---|---|---|
| CETP TP10 AKAVSNLTESRS ESLQS SEQ ID NO: 96 | Epitope | 5' GGCCGGCGGTGGAGCCA AGGCCGTGAGCAACCTGAC CGAGAGCAGAAGCGAGAGC CTGCAGAGCGGTGGCGGTG GA 3' SEQ ID NO: 128 | 5' CGCGTCCACCGCCACC GCTCTGCAGGCTCTCGCT TCTGCTCTCGGTCAGGTT GCTCACGGCCTTGGCTCC ACCGCC 3' SEQ ID NO: 129 | Type I Ala/Gly |
| CETP TP11 SLTGDEFKKVLE T SEQ ID NO: 97 | Epitope | 5' GGCCGGCGGTGGAAGCC TGACCGGCGACGAATTCAA GAAGGTGCTGGAGACCGGT GGCGGTGGA 3' SEQ ID NO: 130 | 5' CGCGTCCACCGCCACC GGTCTCCAGCACCTTCTT GAATTCGTCGCCGGTCAG GCTTCCACCGCC 3' SEQ ID NO: 131 | Type I Ala/Gly |
| CETP TP12 REAVAYRFEED SEQ ID NO: 98 | Epitope | 5' GGCCGGCGGTGGAAGAG AGGCCGTGGCCTACAGATT CGAAGAGGACGGTGGCGGT GGA 3' SEQ ID NO: 132 | 5' CGCGTCCACCGCCACC GTCCTCTTCGAATCTGTA GGCCACGGCCTCTCTTCC ACCGCC 3' SEQ ID NO: 133 | Type I Ala/Gly |
| CETP TP13 INPEIITLDG SEQ ID NO: 99 | Epitope | 5' GGCCGGCGGTGGAATCA ACCCCGAGATCATCACCCT GGACGGCGGTGGCGGTGGA 3' SEQ ID NO: 134 | 5' CGCGTCCACCGCCACC GCCGTCCAGGGTGATGAT CTCGGGGTTGATTCCACC GCC 3' SEQ ID NO: 135 | Type I Ala/Gly |
| CETP TP18 DISVTGAPVITAT YL SEQ ID NO: 100 | Epitope | 5' GGCCGGCGGTGGAGACA TCAGCGTGACCGGTGCACC CGTGATCACCGCCACCTAC CTGGGTGGCGGTGGA 3' SEQ ID NO: 136 | 5' CGCGTCCACCGCCACC CAGGTAGGTGGCGGTGAT CACGGGTGCACCGGTCAC GCTGATGTCTCCACCGCC 3' SEQ ID NO: 137 | Type I Ala/Gly |

TABLE 11-continued rabbit CETP derived epitopes in I-453

| Name/<br>Peptide Seq. | Type | sense<br>Oligonucleotide | anti-sense<br>Oligonucleotide | Adap-<br>tor |
|---|---|---|---|---|
| CETP TP20<br>DISVTGAPVITA<br>SEQ ID NO: 101 | Epitope | 5' GGCCGGCGGTGGAGACA<br>TCAGCGTGACCGGTGCACC<br>CGTGATCACCGCCGGTGGC<br>GGTGGA 3'<br>SEQ ID NO: 138 | 5' CGCGTCCACCGCCACC<br>GGCGGTGATCACGGGTGC<br>ACCGGTCACGCTGATGTC<br>TCCACCGCC 3'<br>SEQ ID NO: 139 | Type I<br>Ala/Gly |
| Ritsch-1<br>DQSVDFEIDSA<br>SEQ ID NO: 127 | Epitope | 5' GGCCGGCGGTGGAGACC<br>AGAGCGTGGACTTCGAGAT<br>CGACAGCGCCGGTGGCGGT<br>GGA 3'<br>SEQ ID NO: 140 | 5' CGCGTCCACCGCCACC<br>GGCGCTGTCGATCTCGAA<br>GTCCACGCTCTGGTCTCC<br>ACCGCC 3'<br>SEQ ID NO: 141 | Type I<br>Ala/Gly |

7.2. Insertion of CETP Epitopes into the AAV2 Capsid at Position I-453 and I-587

Using the cloning strategy described above, the following AAV2 capsid variants carrying rabbit CETP epitopes at position I-453 and I-587 were produced:

TABLE 12

CETP double insertion mutants

| Name | Epitope at I-453 | Epitope at I-587 |
|---|---|---|
| AAV-TP10-2x | AKAVSNLTESRSESLQS<br>SEQ ID NO: 96 | AKAVSNLTESRSESLQS<br>SEQ ID NO: 96 |
| AAV-TP11-2x | SLTGDEFKKVLET<br>SEQ ID NO: 97 | SLTGDEFKKVLET<br>SEQ ID NO: 97 |
| AAV-TP12/13 | REAVAYRFEED<br>SEQ ID NO: 98 | INPEIITLDG<br>SEQ ID NO: 99 |
| AAV-TP12-2x | REAVAYRFEED<br>SEQ ID NO: 98 | REAVAYRFEED<br>SEQ ID NO: 98 |
| AAV-TP13-2x | INPEIITLDG<br>SEQ ID NO: 99 | INPEIITLDG<br>SEQ ID NO: 99 |
| AAV-TP18-2x | DISVTGAPVITATYL<br>SEQ ID NO: 100 | DISVTGAPVITATYL<br>SEQ ID NO: 100 |
| AAV-TP20-2x | DISVTGAPVITA<br>SEQ ID NO: 101 | DISVTGAPVITA<br>SEQ ID NO: 101 |
| AAV-Ritsch1-2x | DQSVDFEIDSA<br>SEQ ID NO: 127 | DQSVDFEIDSA<br>SEQ ID NO: 127 |
| AAV2-CETin-2x | CDAGSVRTNAPD<br>SEQ ID NO: 60 | CDAGSVRTNAPD<br>SEQ ID NO: 60 |

7.3. Insertion of Cytokine Epitopes into the AAV2 Capsid at Position I-453

The following murine cytokine derived epitopes were cloned into position I-453 of the AAV2 capsid using annealed oligonucleotides as described above. Each of the inserted epitope sequences in the AAV2 backbone at I-453 is flanked by the alanine/glycine adaptors according this section 7 for I-453 above.

TABLE 13 murine cytokine derived epitopes in I-453

| Name/<br>Peptide Seq. | Type | sense<br>Oligonucleotide | anti-sense<br>Oligonucleotide | Adap-<br>tor |
|---|---|---|---|---|
| mTNFα-V1<br>SSQNSSDKPVAH<br>VVANHQVE<br>SEQ ID NO: 142 | Epitope | 5'GGCCGCCGGTGGAGGCA<br>GCAGCCAGAACAGCAGCGA<br>CAAGCCCGTGGCCCACGTG<br>GTGGCTAACCACCAGGTGG<br>AGGGCGGTGGAGGG 3'<br>SEQ ID NO: 145 | 5'CGCGCCCTCCACCGCC<br>CTCCACCTGGTGGTTAGC<br>CACCACGTGGGCCACGGG<br>CTTGTCGCTGCTGTTCTG<br>GCTGCTGCCTCCACCGGC<br>3'<br>SEQ ID NO: 148 | Type II<br>Ala/Gly |
| mIL-17-V1<br>NAEGKLDHHMN<br>SVL<br>SEQ ID NO: 143 | Epitope | 5'GGCCGCCGGTGGAGGCA<br>ACGCCGAGGGCAAGCTTGA<br>CCACCACATGAACAGCGTG<br>CTGGGCGGTGGAGGG 3'<br>SEQ ID NO: 146 | 5'CGCGCCCTCCACCGCC<br>CAGCACGCTGTTCATGTG<br>GTGGTCAAGCTTGCCCTC<br>GGCGTTGCCTCCACCGGC<br>3'<br>SEQ ID NO: 149 | Type II<br>Ala/Gly |
| mIL-6-V2<br>LEEFLKVTLRS<br>SEQ ID NO: 144 | Epitope | 5' GGCCGCCGGTGGAGGCC<br>TGGAGGAATTCCTGAAGGT<br>GACCCTGAGAAGCGGCGGT<br>GGAGGG 3'<br>SEQ ID NO: 147 | 5' CGCGCCCTCCACCGCC<br>GCTTCTCAGGGTCACCTT<br>CAGGAATTCCTCCAGGCC<br>TCCACCGGC 3'<br>SEQ ID NO: 150 | Type II<br>Ala/Gly |

The following sequences, which are homologues to the corresponding murine cytokine sequences, can be integrated into the AAV2 capsid at position I-453 according to the methods described above:

TABLE 14 human cytokine derived epitopes in I-453

| Cytokine | murine epitope | human epitope |
|---|---|---|
| TNF-α V1 | SSQNSSDKPVAHVVANHQVE<br>SEQ ID NO: 142 | SSRTPSDKPVAHVVANPQAE<br>SEQ ID NO: 116 |
| TNF-α V2 | SQNSSDKPVAHVVANH<br>SEQ ID NO: 151 | SRTPSDKPVAHVVANP<br>S TABLE 16-continued Vaccines used for immunization of rabbits

| Name of vaccine | Vaccine carrier | Insertion Site | Epitope | Dose (µg) |
|---|---|---|---|---|
| AAV-TP12 | AAV2 | I-587 | REAVAYRFEED SEQ ID NO: 98 | 14.1 |
| AAV-TP13 | AAV2 | I-587 | INPEIITLDG SEQ ID NO: 99 | 13.3 |
| AAV-TP18 | AAV2 | I-587 | DISVTGAPVITATYL SEQ ID NO: 100 | 7.2 |
| LPH-TP11 | LPH | N/A | CSLTGDEFKKVLET SEQ ID NO: 155 | see text |
| LPH-TP12 | LPH | N/A | CREAVAYRFEED SEQ ID NO: 156 | see text |
| LPH-TP13 | LPH | N/A | CINPEIITLDG SEQ ID NO: 157 | see text |
| LPH-TP18 | LPH | N/A | CDISVTGAPVITATYL SEQ ID NO: 158 | see text |

For each vaccination approach two rabbits were immunized s.c. with the vaccines shown in the table above four times (one prime and three boost immunizations). The first boost immunization was performed 2 weeks after an initial prime immunization. Rabbits were boosted another two times with the vaccines at intervals of 3 weeks. Serum of the immunized animals was prepared two weeks after each boost immunization.

The purified AAV-based vaccines were mixed an equal volume of formulation buffer (PBS with 1% sorbitol, 0.2% Tween-20, 25% propylenglycol, 200 mM NaCl and 2.5 mM $MgCl_2$) for stabilization of the particles and stored at −80° C. until administration. If necessary, the volume of the AAV-based vaccines was adjusted to 0.3 ml with formulation buffer directly before application. The vaccines were administered s.c. in the presence of 0.7 ml adjuvant (total volume 1 ml). The adjuvant was provided by BIOGENES and contained amongst others 0.01% lipopolysaccharide derived from Phormidium, 95% paraffin oil, 2.4% Tween-40 and 0.1% cholesterol.

The LPH-coupled peptides (in 0.3 ml TBS) were administered s.c. in the presence of 0.7 ml of the adjuvant provided by BIOGENES. 1 mg of the LPH-peptide conjugate was administered for the prime immunization. 0.5 mg of the conjugate was used for the 1st boost immunization and 0.25 mg of the conjugate were used for the 2nd and 3rd boost immunization.

Induction of anti-CETP auto-antibodies in the vaccinated animals was determined by ELISA using recombinant rabbit CETP as antigen. For production of rabbit CETP, the CETP cDNA was amplified by RT-PCR using the primers

```
rCETP-uni
                                  (SEQ ID NO: 159)
5'- GGG GAA TTC ATG TCC CAA AGG CGC CTC CTA CG-3'
and rCETP-rev
                                  (SEQ ID NO: 160)
5'- GGG GGA TCC CTA GCT CAG GCT CTG

GAG GAA ATC C-3'
``` and rabbit liver PolyA+ RNA (CLONTECH) as template. The CETP cDNA was cloned into the EcoRI/BamHI site of the vector p3XFLAG-CMV-8 (SIGMA). The resulting vector encodes the mature CETP sequence with a C-terminal FLAG®-tag and an N-terminal preprotrypsin leader sequence for secretion of the recombinant protein. For expression of recombinant rabbit CETP 293T cells were transfected with the vector by calcium phosphate transfection as described above. CETP was purified from the cell culture supernatant by affinity chromatography using anti-FLAG® M2 agarose beads (SIGMA). Purity of the recombinant rabbit CETP was analyzed by SDS-PAGE and subsequent colloidal Coomassie staining. CETP activity was determined using a commercially available CETP activity assay (ROAR).

For titration of rabbit CETP auto-antibodies in the immune sera, a 96-well MAXISORP plate (NUNC) was coated with purified recombinant rabbit CETP (100 ng/well) for 1 h at 37° C. After coating wells were washed with wash buffer (PBS/0.1% Tween-20) and subsequently incubated with blocking buffer (5% skim milk in wash buffer) for 1 h at 37° C. After blocking of the wells, immobilized CETP was incubated with serial dilutions of the immune sera in dilution buffer (wash buffer with 1% skim milk and 1% BSA) for 1 h at 37° C. Rabbit pre-immune sera or rabbit sera of unrelated vaccinations served as negative controls. After washing binding of rabbit IgG to the immobilized CETP was detected using a HRP-labelled anti-rabbit IgG antibody (H+L) (DAKO; 1:2500 in dilution buffer). Signals (OD) were detected using TMB (KEMENTEC) as substrate.

CETP auto-antibody titers were determined by end point dilution. The titer of the immune serum corresponds to the intersection point of the titration curve of the immune sera with the limit of detection of the assay.

The limit of detection (LOD) of the assay was calculated as follows:

$$\text{Mean OD (unspecific sera)} + 3.3 \times \text{standard deviation OD (unspecific sera)}$$

In addition to the CETP auto-antibody titers, the anti-peptide titers of the immune sera were analyzed. The free peptides (corresponding to the epitopes integrated in the AAV capsid or coupled to LPH) were covalently immobilized in a 96-well plate (REACTI-BIND™ Amine-binding, Maleic Anhydride Activated Plates; PIERCE). For immobilization of the peptide, the 96-well plate was incubated with 1 µg peptide per well in a total volume of 50 µl PBS for at least 1 h at 37° C. After coating with the peptides wells were blocked with 200 µl/well blocking buffer (PBS/5% skim milk/0.1% Tween-20) for 1 h at 37° C. After blocking of the wells, immobilized peptides were incubated with serial dilutions of the immune sera in dilution buffer (PBS with 1% skim milk, 1% BSA, 0.1% Tween-20) for 1 h at 37° C. Rabbit pre-immune sera or rabbit sera of unrelated vaccinations served as negative controls. After washing binding of rabbit IgG to the immobilized CETP was detected using a HRP-labelled anti-rabbit IgG antibody (DAKO; 1:2500 in dilution buffer). Signals (OD) were detected using TMB (KEMENTEC) as substrate. Antibody titers were determined as described above.

Except for one animal vaccinated with AAV-TP13 the data demonstrate that vaccination with AAV-based vaccines induces high titers of target-specific auto-antibodies that are not obtained using peptide-based vaccines. Accordingly AAV-based vaccines are able to break self-tolerance and induce high levels of auto-antibodies (FIG. 9). The immunogenic properties of the peptide based vaccines are reflected by the high titers of peptide specific antibodies induced by the peptide vaccines (FIG. 10). However, these antibodies show only weak reaction with native rabbit CETP (FIG. 9) suggesting that peptide based vaccines—although immunogenic—have only a limited potential to break self-tolerance and induce low levels of auto-antibodies.

8.3. The AAV Capsid Structure is Essential for Breaking of Self-Tolerance and Induction of Auto-Antibodies To demonstrate that the capsid structure and the structured, repetitive presentation of epitopes within the AAV-capsid are essential for breaking of self-tolerance of the immune system and induction of auto-antibodies, rabbits were immunized with heat-denatured AAV-TP11-2× or AAV-TP18-2× particles. Results were compared with vaccinations using the corresponding native particles. The AAV-variant AAV-TP11-2× carries the CETP TP11 epitope (SLTGDEFKKVLET, SEQ ID NO: 97) at positions I-453 and I-587. The AAV-variant AAV-TP18-2× carries the CETP TP18 epitope (DISVTGAPVITATYL, SEQ ID NO: 100) at positions I-453 and I-587. For heat denaturation the particles were mixed with an equal volume of formulation buffer (PBS with 1% sorbitol, 0.2% Tween-20, 25% propylenglycol, 200 mM NaCl and 2.5 mM $MgCl_2$) and incubated at 90° C. for 15 min. Destruction of the particle conformation was analyzed by AAV2 titration ELISA recognizing a conformational epitope within the native capsid. Protein concentration of the heat-denatured particles was determined by Micro BCA assay (Pierce) and analyzed by Western blotting using a polyclonal anti-AAV2 antibody generated by immunization of rabbits with purified VP3 protein of AAV2 (data not shown).

Rabbits were immunized with heat-denatured AAV-TP11-2× particles (5.7 µg per application) or AAV-TP18-2× particles (1.8 µg per application) s.c. in the presence of an adjuvant provided by BIOGENES as described above. 2 weeks after an initial prime immunization rabbits were boosted with the heat-denatured particles. Serum of the animals was analyzed 2 weeks after the boost immunization for levels of CETP auto-antibodies as described above. In a control group rabbits were vaccinated with native AAV-TP11-2× or AAV-TP18-2× particles using the same regimen as for the heat-denatured particles.

Analysis of the CETP auto-antibody titer in the sera of the immunized animals demonstrates that destruction of the native capsid conformation results in a strongly impaired induction of CETP antibodies compared with the native vaccine (FIG. 11) showing that the native capsid structure and the structured presentation of the epitopes within the capsid are essential for breaking of self-tolerance.

8.4. Evaluation of the Impact of Anti-AAV2 Antibodies on Immunization with AAV2-Based Vaccines The immunization experiments demonstrated that AAV-based vaccines induce high titers of anti-AAV capsid antibodies in addition to the target specific antibodies (data not shown). However, most humans are AAV2 positive meaning that these persons have anti-AAV2 antibody titers that potentially might affect vaccination results using AAV2-based particles. To evaluate the impact of anti-AAV2 antibodies on the immunization success of AAV2-based vaccines, rabbits were pre-immunized by two applications of wtAAV2 (4.5 µg per application), before immunization (prime and two boost immunizations) with an AAV2-based CETP vaccine (AAV-TP18) was started. wtAAV2 particles were administered s.c. or i.m. in the presence of an adjuvant provided by BIOGENES as described above. 2 weeks after an initial prime immunization with wtAAV2, rabbits were boosted once again with wtAAV2. Serum was analyzed two weeks after the prime and $1^{st}$ boost immunization for the level of anti-AAV2 antibodies. The anti-AAV2 antibody titer was determined by ELISA using immobilized wtAAV2 particles as described below. The data demonstrate that high levels of anti-wtAAV2 antibodies are detectable after two applications of wtAAV2 for both s.c. and i.m. administration (FIG. 12A).

3 weeks after boost immunization with wtAAV2, rabbits received the first prime immunization with the AAV2-based vaccine AAV-TP18 (7.2 µg per application). The vaccine was administered s.c. or i.m. in the presence of adjuvant provided by BIOGENES as described above. Rabbits were boosted with the vaccines 2 weeks after the prime vaccination. Sera were analyzed 2 weeks after the boost vaccination for the level of CETP auto-antibodies (FIG. 12B). CETP auto-antibody titers were determined as described above. Results were compared to vaccination (s.c.) of animals not pre-immunized with wtAAV2.

The data demonstrate that wtAAV2 pre-immunization results in high titers of anti-AAV2 capsid antibodies. However, these high anti-AAV2 capsid antibodies do not impair the immunization success of an AAV2-based vaccine, in this case regarding the induction of anti-CETP auto-antibodies. Accordingly, it is concluded that AAV2 sero-positive humans are equally eligible for vaccination with AAV2-particles as sero-negative humans and that sero-conversion of a vaccinated human during a vaccination protocol does not impair vaccination success.

Determination of anti-wtAAV2 Antibody Titers:

The anti-AAV2 antibody titer was determined by ELISA using immobilized wtAAV2 particles. Briefly, $5 \times 10^{09}$ wtAAV2 particles were immobilized in each well of a 96-well MAXISORP plate (NUNC) in a total volume of 50 µl PBS per well. The plate was incubated at 37° C. for 1 h. After blocking of the wells with PBS 15% skim milk/0.1% Tween-20, immobilized wtAAV2 particles were incubated with serial dilutions of the immune sera in dilution buffer (PBS with 1% skim milk, 1% BSA, 0.1% Tween-20) for 1 h at 37° C. Rabbit pre-immune sera or rabbit sera of unrelated vaccinations served as negative controls. After washing binding of rabbit IgG to the immobilized AAV2 was detected using a HRP-labelled anti-rabbit IgG antibody and TMB as substrate. Antibody titers were determined as described above.

8.5. Prime/Boost Regimen for AAV-Based Vaccines 16.4 µg AAV2 particles carrying the CETP-intern epitope (CDAGSVRTNAPD, SEQ ID NO: 60) at position I-453 and I-587 (AAV2-CETin-2×) were administered i.m. at each prime or boost immunization together with the adjuvant provided by BIOGENES as described above.

Three different regimens were evaluated. Group A received one prime and three boost applications of AAV2-CETin-2× (AAV2-based vaccination). Group B received one prime and one boost immunization with AAV2-CETin-2× followed by two boost immunizations with the LPH-coupled CETP-intern peptide (LPH-peptide boost). Group C received one prime and one boost immunization with AAV2-GETIn-2× followed by two boost immunizations with AAV1-CETin (AAV1 particle carrying the CETP-intern epitope at position 1-588; 11.7 µg/application). In each group the first boost immunization was performed two weeks after the prime immunization. The $2^{nd}$ and $3^{rd}$ boost immunization was performed three weeks after the preceding boost vaccination.

Immune sera were analyzed for anti-CETP-reactivity (CETP auto-antibody titer) two weeks after the 1st, 2nd and 3rd boost immunization as described above (FIG. 13).

Resulting data demonstrate that high levels of CETP auto-antibodies are detectable in animals vaccinated with AAV2-CETin-2× only (group A). There is no increase of CETP auto-antibodies observed in the group of animals boosted with LPH-coupled CETP peptide (group B). Furthermore, data demonstrate that switching of the serotype of the AAV-backbone (group C) has the potential to increase the immune response to a self-antigen compared to boost vaccinations with an individual AAV serotype.

8.6. Immunization Against Human IgE Using AAV-Based Vaccines

A panel of AAV-based vaccines carrying epitopes derived from human IgE was generated as described above. AAV-based IgE vaccines were compared to the corresponding peptide vaccines containing the same epitope coupled to LPH as carrier protein. The peptides were chemically synthesized with a C- or N-terminal cysteine residue that was used for coupling of the peptides to LPH.

The following vaccines were used for immunization of rabbits:

TABLE 17

AAV- and LPH-based vaccines used for immunization against human IgE

| Name of vaccine | Vaccine carrier | Insertion Site | Epitope | Dose (µg) | Appl. |
|---|---|---|---|---|---|
| AAV-Kricek | AAV2 | I-587 | Kricek | 3.1 | s.c. |
| AAV-3DEpi3 | AAV2 | I-587 | 3DEpi3 | 4.4 | s.c. |
| AAV-Flex | AAV2 | I-587 | Flex | 16.3 | i.m. |
| AAV-Bind2 | AAV2 | I-587 | Bind2 | 5.1 | i.m. |
| LPH-Kricek | LPH | N/A | VNLTWSRASGC SEQ ID NO: 161 | see text | i.m. |
| LPH-3DEpi3 | LPH | N/A | CDSNPRGVSAYLSR SEQ ID NO: 162 | see text | i.m. |
| LPH-Flex | LPH | N/A | CEDGQVMDVDLS SEQ ID NO: 163 | see text | i.m. |
| LPH-Bind2 | LPH | N/A | CEKQRNGTLT SEQ ID NO: 164 | see text | i.m. |

For each vaccination approach two rabbits were immunized with the vaccines shown in the table above four times (one prime and three boost immunizations). The first boost immunization was performed 2 weeks after an initial prime immunization. Rabbits were boosted another two times with the vaccines at intervals of 3 weeks.

The purified AAV-based vaccines were mixed with an equal volume of formulation buffer (PBS with 1% sorbitol, 0.2% Tween-20, 25% propylenglycol, 200 mM NaCl and 2.5 mM $MgCl_2$) for stabilization of the particles and stored at −80° C. until administration. If necessary, the volume of the vaccine was adjusted to 0.3 ml-0.5 ml with formulation buffer directly before application. The AAV-based vaccines were administered s.c. or i.m. together with the BIOGENES adjuvant (total volume 1 ml).

The LPH-coupled peptides (in 0.3 ml TBS) were administered i.m. in the presence of 0.7 ml of the adjuvant provided by BIOGENES. 1 mg of the LPH-peptide conjugate was administered for the prime immunization. 0.5 mg of the conjugate was used for the $1^{st}$ boost immunization and 0.25 mg of the conjugate were used for the $2^{nd}$ and $3^{rd}$ boost immunization.

Induction of anti-human IgE antibodies in the vaccinated animals was determined by ELISA using human IgE (DI-ATEC, Oslo, Norway) as antigen. A 96-well MAXISORP plate (NUNC) was coated with human IgE (1 µg/well) for 1 h at 37° C. After coating wells were washed with wash buffer (PBS/0.1% Tween-20) and subsequently incubated with blocking buffer (5% skim milk in wash buffer) for 1 h at 37° C. After blocking of the wells, immobilized human IgE was incubated with serial dilutions of the immune sera in dilution buffer (wash buffer with 1% skim milk and 1% BSA) for 1 h at 37° C. Rabbit pre-immune sera or rabbit sera of unrelated vaccinations served as negative controls. After washing binding of rabbit IgG to the immobilized IgE was detected using a HRP-labelled anti-rabbit IgG antibody (DAKO; 1:2500 in dilution buffer). Signals (OD) were detected using TMB (KEMENTEC) as substrate.

In addition to the IgE titers, the anti-peptide titers of the immune sera were analyzed. The free peptides (corresponding to the epitopes integrated in the AAV capsid or coupled to LPH) were covalently immobilized in a 96-well plate (REACTI-BIND™ Amine-binding, Maleic Anhydride Activated Plates; PIERCE) as described above. After blocking of the wells, immobilized peptides were incubated with serial dilutions of the immune sera in dilution buffer (PBS with 1% skim milk, 1% BSA, 0.1% Tween-20) for 1 h at 37° C. Rabbit pre-immune sera or rabbit sera of unrelated vaccinations served as negative controls. After washing binding of rabbit IgG to the immobilized CETP was detected using a HRP-labelled anti-rabbit IgG antibody (DAKO; 1:2500 in dilution buffer). Signals (OD) were detected using TMB (KEMENTEC) as substrate. Antibody titers were determined as described above The anti-IgE titers of the immune sera are summarized in Table 18 below:

TABLE 18

Mean anti-IgE titer of immunizations with AAV- vs. LPH-based IgE vaccines

| Vaccine | anti-IgE Titer $1^{st}$ Boost | anti-IgE Titer $2^{nd}$ Boost | anti-IgE Titer $3^{rd}$ Boost |
|---|---|---|---|
| AAV-Kricek | 4750 | 20150 | 25460 |
| AAV-Kricek* | n.d. | 7950 | 27000 |
| AAV-3DEpi3* | 5000 | 18200 | 30140 |
| AAV-Bind2 | 575 | 3075 | 7750 |
| AAV-Flex | 17200 | 40300 | 38100 |
| LPH-Kricek | n.d. | 1300 | 400 |
| LPH-3DEpi3 | 705 | 1400 | 1600 |
| LPH-Flex | 15000 | 14000 | 23250 |
| LPH-Bind2 | 0 | 0 | 0 |

*AAV-based vaccines were used for the prime and $1^{st}$ boost immunization; $2^{nd}$ and $3^{rd}$ boost immunization were performed with the corresponding LPH-coupled peptide Interestingly, vaccination of rabbits with LPH-Kricek, LPH-3DEpi3 or LPH-Bind2 failed to induce significant levels of antibodies against human IgE. The immunogenic properties of the peptide based vaccines are reflected by the high titers of peptide specific antibodies induced by the peptide vaccines (data not shown). However, these antibodies show no or only weak reaction with native human IgE. Only LPH-Flex induced reasonably high titers of antibodies specific for native human IgE. This is in clear contrast to the results obtained with the corresponding AAV-based vaccines like AAV-Kricek (FIG. 14) which generate considerably higher human IgE specific antibody titers compared to the corresponding LPH-fusion constructs. This indicates that the fixed conformation of the corresponding IgE epitopes in the AAV2 capsid resembles the structure of the sequence within the IgE molecule in a better way than the LPH-coupled peptides. It should be noted that the generation of anti-human IgE antibodies in this animal model with rabbits does not overcome tolerance of the immune system to self-antigens.

LITERATURE

Hereby Incorporated by Reference

Arnold, G. S., Sasser, A. K., Stachler, M. D. and Bartlett, J. S. (2006) Mol Ther, 14, 97-106.

Asokan, A. and Samulski, R. J. (2006) Nat Biotechnol, 24, 158-60.

Asquith, D. L. and I. B. McInnes (2007). "Emerging cytokine targets in rheumatoid arthritis." Curr Opin Rheumatol 19(3): 246-51.

Aumailley, M., Gerl, M., Sonnenberg, A., Deutzmann, R. and Timpl, R. (1990) FEBS Lett, 262, 82-6.

Barassi, C., E. Soprana, et al. (2005). J Virol 79(11): 6848-58.

Bousquet, J., Cabrera, P., Berkman, N., Buhl, R., Holgate, S., Wenzel, S., Fox, H., Hedgecock, S., Blogg, M. and Cioppa, G. D. (2005) Allergy, 60, 302-8.

Chackerian, B., Lowy, D. R. et al. (1999). Proc Natl Acad Sci USA 96(5): 2373-8.

Chackerian, B., Lowy, D. R. and Schiller, J. T. (2001) J Clin Invest, 108, 415-23.

Chatterjee, M. B., Foon, K. A. and Kohler, H. (1994) Cancer Immunology Immunotherapy, 38, 75-82.

Cook, J. P., Henry, A. J., McDonnell, J. M., Owens, R. J., Sutton, B. J. and Gould, H. J. (1997) Biochemistry, 36, 15579-88.

Corpet, F. (1988) Nucleic Acids Res, 16, 10881-90.

Dean, D. A., Strong, D. D. and Zimmer, W. E. (2005) Gene Ther, 12, 881-90.

Gamsjaeger, R., C. K. Liew, et al. (2007). Trends Biochem Sci 32(2): 63-70.

Garman, S. C., Wurzburg, B. A., Tarchevskaya, S. S., Kinet, J. P. and Jardetzky, T. S. (2000) Nature, 406, 259-66.

Girod, A., Ried, M., Wobus, C., Lahm, H., Leike, K., Kleinschmidt, J., Deleage, G. and Hallek, M. (1999) Nat Med, 5, 1438.

Grifman, M., Trepel, M., Speece, P., Gilbert, L. B., Arap, W., Pasqualini, R. and Weitzman, M. D. (2001) Mol Ther, 3, 964-75.

Helm, B., Kebo, D., Vercelli, D., Glovsky, M. M., Gould, H., Ishizaka, K., Geha, R. and Ishizaka, T. (1989) Proc Natl Acad Sci USA, 86, 9465-9.

Helm, B., Marsh, P., Vercelli, D., Padlan, E., Gould, H. and Geha, R. (1988) Nature, 331, 180-3.

Huttner, N. A., Girod, A., Perabo, L., Edbauer, D., Kleinschmidt, J. A., Buning, H. and Hallek, M. (2003) Gene Ther, 10, 2139-47.

Jefferis, R. (1993) Immunol Today, 14, 119-21.

Jerne, N. K. (1974) Ann Immunol (Paris), 125C, 373-89.

Jerne, N. K., Roland, J. and Cazenave, P. A. (1982) Embo J, 1, 243-7.

Kay, M. A., Glorioso, J. C. and Naldini, L. (2001) Nat Med, 7, 33-40.

Kern, A., Schmidt, K., Leder, C., Muller, O. J., Wobus, C. E., Bettinger, K., Von der Lieth, C. W., King, J. A. and Kleinschmidt, J. A. (2003) J Virol, 77, 11072-81.

Klenerman, P., Tolfvenstam, T., Price, D. A., Nixon, D. F., Broliden, K. and Oxenius, A. (2002) Pathol Biol (Paris), 50, 317-25.

Kricek, F., Ruf, C., Rudolf, M. P., Effenberger, F., Mayer, P. and Stadler, B. M. (1999) Int Arch Allergy Immunol, 118, 222-3.

Laity, J. H., B. M. Lee, et al. (2001). Curr Opin Struct Biol 11(1): 39-46.

Laughlin, C. A., Tratschin, J. D., Coon, H. and Carter, B. J. (1983) Gene, 23, 65-73.

Levy, D. A. and Chen, J. (1970) N Engl J Med, 283, 541-2.

Li, Q., Cao, C., Chackerian, B., Schiller, J., Gordon, M., Ugen, K. E. and Morgan, D. (2004) BMC Neurosci, 5, 21.

Lieber, A. (2003) Nat Biotechnol, 21, 1011-3.

Lux, K., Goerlitz, N., Schlemminger, S., Perabo, L., Goldnau, D., Endell, J., Leike, K., Kofler, D. M., Finke, S., Hallek, M. and Buning, H. (2005) J Virol, 79, 11776-87.

Maheshri, N., Koerber, J. T., Kaspar, B. K. and Schaffer, D. V. (2006) Nat Biotechnol, 24, 198-204.

Misumi, S., D. Nakayama, et al. (2006). J Immunol 176(1): 463-71.

Moskalenko, M., Chen, L., van Roey, M., Donahue, B. A., Snyder, R. O., McArthur, J. G. and Patel, S. D. (2000) J Virol, 74, 1761-6.

Muller, O. J., Kaul, F., Weitzman, M. D., Pasqualini, R., Arap, W., Kleinschmidt, J. A. and Trepel, M. (2003) Nat Biotechnol, 21, 1040-6.

Nicklin, S. A., Buening, H., Dishart, K. L., de Alwis, M., Girod, A., Hacker, U., Thrasher, A. J., Ali, R. R., Hallek, M. and Baker, A. H. (2001) Mol Ther, 4, 174-81.

Nygren, P. A. and Skerra, A. (2004) J Immunol Methods, 290, 3-28.

Opie, S. R., Warrington, K. H., Jr., Agbandje-McKenna, M., Zolotukhin, S, and Muzyczka, N. (2003) J Virol, 77, 6995-7006.

Parker, K. C., M. A. Bednarek, et al. (1994). J Immunol 152(1): 163-75.

Perabo, L. (2003) In Institut für BiochemieLMU, München, pp. 1-121.

Perabo, L., Buning, H., Kofler, D. M., Ried, M. U., Girod, A., Wendtner, C. M., Enssle, J. and Hallek, M. (2003) Mol Ther, 8, 151-7.

Perabo, L., Endell, J., King, S., Lux, K., Goldnau, D., Hallek, M. and Buning, H. (2006a) J Gene Med, 8, 155-62.

Perabo, L., Goldnau, D., White, K., Endell, J., Boucas, J., Humme, S., Work, L. M., Janicki, H., Hallek, M., Baker, A. H. and Buning, H. (2006b) J Virol, 80, 7265-9.

Pfeifer, A. and Verma, I. M. (2001) Annu Rev Genomics Hum Genet, 2, 177-211.

Presta, L., Shields, R., O'Connell, L., Lahr, S., Porter, J., Gorman, C. and Jardieu, P. (1994) J Biol Chem, 269, 26368-73.

Ried, M. U., Girod, A., Leike, K., Buning, H. and Hallek, M. (2002) J Virol, 76, 4559-66.

Riemer, A. B., Untersmayr, E., Knittelfelder, R., Duschl, A., Pehamberger, H., Zielinski, C. C., Scheiner, O. and Jensen-Jarolim, E. (2007) Cancer Res, 67, 3406-11.

Rittershaus, C. W., Miller, D. P., Thomas, L. J., Picard, M. D., Honan, C. M., Emmett, C. D., Pettey, C. L., Adari, H., Hammond, R. A., Beattie, D. T., Callow, A. D., Marsh, H. C. and Ryan, U.S. (2000) Arterioscler Thromb Vasc Biol, 20, 2106-12.

Rudolf, M. P., Vogel, M., Kricek, F., Ruf, C., Zurcher, A. W., Reuschel, R., Auer, M., Miescher, S, and Stadler, B. M. (1998) J Immunol, 160, 3315-21.

Rudolf, M. P., Zuercher, A. W., Nechansky, A., Ruf, C., Vogel, M., Miescher, S. M., Stadler, B. M. and Kricek, F. (2000) J Immunol, 165, 813-9.

Ruffing, M., Heid, H. and Kleinschmidt, J. A. (1994) J Gen Virol, 75 (Pt 12), 3385-92.

Shi, W., Arnold, G. S, and Bartlett, J. S. (2001) Hum Gene Ther, 12, 1697-711.

Shi, W. and Bartlett, J. S. (2003) Mol Ther, 7, 515-25.

Shi, X., Fang, G., Shi, W. and Bartlett, J. S. (2006) Hum Gene Ther, 17, 353-61.

Smolen, J. S, and Steiner, G. (2003) Nat Rev Drug Discov, 2, 473-88.

Stachler, M. D. and Bartlett, J. S. (2006) Gene Ther, 13, 926-31.

Stadler, B. M., Zurcher, A. W., Miescher, S., Kricek, F. and Vogel, M. (1999) Int Arch Allergy Immunol, 118, 119-21.

Summerford, C., Bartlett, J. S, and Samulski, R. J. (1999) Nat Med, 5, 78-82.

Theiss, H. D., Kofler, D. M., Buning, H., Aldenhoff, A. L., Kaess, B., Decker, T., Baumert, J., Hallek, M. and Wendtner, C. M. (2003) Exp Hematol, 31, 1223-9.

Uversky V. N., Fernández A. and Fink A. L. (2006) chapter 1, 1-20 in: Protein Reviews Volume 4, editor: M. Zouhair Atassi: Protein Misfolding, Aggregation, and Conformational Disease, Part A: Protein Aggregation and Conformational Disease; Springer.

Varela, F. J. and Coutinho, A. (1991) Immunol Today, 12, 159-66.

Vogel, M., Miescher, S., Kuhn, S., Zurcher, A. W., Stadler, M. B., Ruf, C., Effenberger, F., Kricek, F. and Stadler, B. M. (2000) J Mol Biol, 298, 729-35.

Vogel, M., Tschopp, C., Bobrzynski, T., Fux, M., Stadler, M. B., Miescher, S. M. and Stadler, B. M. (2004) J Mol Biol, 341, 477-89.

Warrington, K. H., Jr., Gorbatyuk, O, S., Harrison, J. K., Opie, S. R., Zolotukhin, S, and Muzyczka, N. (2004) J Virol, 78, 6595-609.

Waterkamp, D. A., Muller, O. J., Ying, Y., Trepel, M. and Kleinschmidt, J. A. (2006) J Gene Med, 8, 1307-19.

White, S. J., Nicklin, S. A., Buning, H., Brosnan, M. J., Leike, K., Papadakis, E. D., Hallek, M. and Baker, A. H. (2004) Circulation, 109, 513-9.

Work, L. M., Buning, H., Hunt, E., Nicklin, S. A., Denby, L., Britton, N., Leike, K., Odenthal, M., Drebber, U., Hallek, M. and Baker, A. H. (2006) Mol Ther, 13, 683-93.

Work, L. M., Nicklin, S. A., Brain, N. J., Dishart, K. L., Von Seggern, D. J., Hallek, M., Buning, H. and Baker, A. H. (2004) Mol Ther, 9, 198-208.

Wu, P., Xiao, W., Conlon, T., Hughes, J., Agbandje-McKenna, M., Ferkol, T., Flotte, T. and Muzyczka, N. (2000) J Virol, 74, 8635-47.

Wu, Z., Asokan, A., Grieger, J. C., Govindasamy, L., Agbandje-McKenna, M. and Samulski, R. J. (2006) J Virol, 80, 11393-7.

Xiao, X., Li, J. and Samulski, R. J. (1998) J Virol, 72, 2224-32.

SEQUENCE LISTING

```
<160> NUMBER OF SEQ ID NOS: 196

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Asn Thr Pro Ser Gly Thr Thr Thr Gln Ser
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Asn Asn Thr Gly Gly Val Gln Phe Asn Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gln Asn Gln Ser Gly Ser Ala Gln Asn Lys
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gln Asn Gln Ser Gly Ser Ala Gln Asn Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gln Thr Thr Gly Gly Thr Ala Asn Thr Gln
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Gln Ser Thr Gly Gly Thr Gln Gly Thr Gln
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Gly Thr Thr Ser Gly Thr Thr Asn Gln Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Ser Asn Pro Gly Gly Thr Ala Gly Asn Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Ser Thr Thr Thr Gly Thr Thr Leu Asn Ala
1               5                   10

```
<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Ser Thr Thr Ser Gly Glu Thr Leu Asn Gln
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Ser Thr Thr Ser Gly Gly Thr Leu Asn Gln
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Phe Gly Asp Ile Gly Val Gln Gln Asp Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Phe Gly Asp Ile Gly Val Gln Gln Asp Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Pro Asp Thr Leu Gly Gly Asp Pro Lys Phe
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Val Ser Ala Thr Tyr Thr Glu Gly Glu Ala
1               5                   10

<210> SEQ ID NO 16
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Ala Gly Thr Leu Thr Ala Gln Gly Ser Arg
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Met Ala Ala Asp Gly Tyr
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Pro Pro Pro Lys Pro Ala Glu Arg His Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Glu Pro Val Lys Thr Ala Pro Gly Lys Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Pro Val Lys Thr Ala Pro Gly Lys Lys Arg
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Ser Gly Thr Gly Lys Ala Gly Gln Gln Pro
1               5                   10

<210> SEQ ID NO 22
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 22

Tyr Lys Gln Ile Ser Ser Gln Ser Gly Ala
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Ser Gln Ser Gly Ala Ser Asn Asp Asn His
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Tyr Leu Thr Leu Asn Asn Gly Ser Gln Ala
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Tyr Tyr Leu Ser Arg Thr Asn Thr Pro Ser
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Tyr Leu Ser Arg Thr Asn Thr Pro Ser Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Thr Thr Gln Ser Arg Leu Gln Phe Ser Gln
1               5                   10

<210> SEQ ID NO 28
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 28

Ala Ser Asp Ile Arg Asp Gln Ser Arg Asn
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Leu Val Asn Pro Gly Pro Ala Met Ala Ser
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Glu Glu Lys Phe Phe Pro Gln Ser Gly Val
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Asn Pro Val Ala Thr Glu Gln Tyr Gly Ser
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Ser Thr Asn Leu Gln Arg Gly Asn Arg Gln
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Leu Gln Arg Gly Asn Arg Gln Ala Ala Thr
1               5                   10

<210> SEQ ID NO 34
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 34

Gln Arg Gly Asn Arg Gln Ala Ala Thr Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Asn Arg Gln Ala Ala Thr Ala Asp Val Asn
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Val Pro Ala Asn Pro Ser Thr Thr Phe Ser
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Thr Phe Ser Ala Ala Lys Phe Ala Ser Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Asn Val Asp Phe Thr Val Asp Thr Asn Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Phe Thr Val Asp Thr Asn Gly Val Tyr Ser
1               5                   10

<210> SEQ ID NO 40
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 40

Ser Ser Ser Thr Asp Pro Ala Thr Gly Asp
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Asn Asn Leu Gln Ser Ser Asn Thr Ala Pro
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Gly Asp Gln Ser Asn Ser Asn Leu Pro
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Thr Asn Asn Gln Ser Ser Thr Thr Ala Pro
1               5                   10

<210> SEQ ID NO 44
<211> LENGTH: 27
<212> TYPE: DNA
<213> ORGANISM: Artificial Sequence
<220> FEATURE:
<223> OTHER INFORMATION: Synthetic Construct

<400> SEQUENCE: 44
gagtcgaccc gggcagccgc ttcgagc                                          27

<210> SEQ ID NO 45
<211> LENGTH: 27
<212> TYPE: DNA
<213> ORGANISM: Artificial Sequence
<220> FEATURE:
<223> OTHER INFORMATION: Synthetic Construct

<400> SEQUENCE: 45
gctcgaagcg gctgcccggg tcgactc                                          27

<210> SEQ ID NO 46
<211> LENGTH: 43
<212> TYPE: DNA
<213> ORGANISM: Artificial Sequence
<220> FEATURE:
<223> OTHER INFORMATION: Synthetic Construct

<400> SEQUENCE: 46
```
caaacactcc aagtggaggg cgcgccgcta ccaccacgca gtc    43

<210> SEQ ID NO 47
<211> LENGTH: 43
<212> TYPE: DNA
<213> ORGANISM: Artificial Sequence
<220> FEATURE:
<223> OTHER INFORMATION: Synthetic Construct

<400> SEQUENCE: 47
gactgcgtgg tggtagcggc gcgccctcca cttggagtgt ttg    43

<210> SEQ ID NO 48
<211> LENGTH: 40
<212> TYPE: DNA
<213> ORGANISM: Artificial Sequence
<220> FEATURE:
<223> OTHER INFORMATION: Synthetic Construct

<400> SEQUENCE: 48
caaacactcc aagtggagcg gccgcagggc gcgccgctac    40

<210> SEQ ID NO 49
<211> LENGTH: 40
<212> TYPE: DNA
<213> ORGANISM: Artificial Sequence
<220> FEATURE:
<223> OTHER INFORMATION: Synthetic Construct

<400> SEQUENCE: 49
gtagcggcgc gccctgcggc cgctccactt ggagtgtttg    40

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Val Asn Leu Thr Trp Ser Arg Ala Ser Gly
1               5                   10

<210> SEQ ID NO 51
<211> LENGTH: 37
<212> TYPE: DNA
<213> ORGANISM: Artificial Sequence
<220> FEATURE:
<223> OTHER INFORMATION: Synthetic Construct

<400> SEQUENCE: 51
ggccgcagtg aacctgacct ggagcagagc ctccggc    37

<210> SEQ ID NO 52
<211> LENGTH: 37
<212> TYPE: DNA
<213> ORGANISM: Artificial Sequence
<220> FEATURE:
<223> OTHER INFORMATION: Synthetic Construct

<400> SEQUENCE: 52
cgcggccgga ggctctgctc caggtcaggt tcactgc    37

<210> SEQ ID NO 53
<211> LENGTH: 49

```
<212> TYPE: DNA
<213> ORGANISM: Artificial Sequence
<220> FEATURE:
<223> OTHER INFORMATION: Synthetic Construct

<400> SEQUENCE: 53
ggccgcagcc gcagtgaacc tgacctggag cagagcctcc ggcgcggca                 49

<210> SEQ ID NO 54
<211> LENGTH: 49
<212> TYPE: DNA
<213> ORGANISM: Artificial Sequence
<220> FEATURE:
<223> OTHER INFORMATION: Synthetic Construct

<400> SEQUENCE: 54
cgcgtgccgc gccggaggct ctgctccagg tcaggttcac tgcggctgc                 49

<210> SEQ ID NO 55
<211> LENGTH: 14
<212> TYPE: PRT
<213> ORGANISM: Artificial Sequence
<220> FEATURE:
<223> OTHER INFORMATION: Synthetic Construct

<400> SEQUENCE: 55

Glu Phe Cys Ile Asn His Arg Gly Tyr Trp Val Cys Gly Asp
1               5                   10

<210> SEQ ID NO 56
<211> LENGTH: 49
<212> TYPE: DNA
<213> ORGANISM: Artificial Sequence
<220> FEATURE:
<223> OTHER INFORMATION: Synthetic Construct

<400> SEQUENCE: 56
ggccgcagaa ttctgcataa accacagggg atactgggtg tgcggagac                 49

<210> SEQ ID NO 57
<211> LENGTH: 49
<212> TYPE: DNA
<213> ORGANISM: Artificial Sequence
<220> FEATURE:
<223> OTHER INFORMATION: Synthetic Construct

<400> SEQUENCE: 57
cgcggtctcc gcacacccag tatcccctgt ggtttatgca gaattctgc                 49

<210> SEQ ID NO 58
<211> LENGTH: 61
<212> TYPE: DNA
<213> ORGANISM: Artificial Sequence
<220> FEATURE:
<223> OTHER INFORMATION: Synthetic Construct

<400> SEQUENCE: 58
ggccgcagcc gcagaattct gcataaacca caggggatac tgggtgtgcg gagacgcggc     60
a                                                                    61

<210> SEQ ID NO 59
<211> LENGTH: 61
<212> TYPE: DNA
<213> ORGANISM: Artificial Sequence
<220> FEATURE:
<223> OTHER INFORMATION: Synthetic Construct
```

<400> SEQUENCE: 59
cgcgtgccgc gtctccgcac acccagtatc ccctgtggtt tatgcagaat tctgcggctg    60
c                                                                    61

<210> SEQ ID NO 60
<211> LENGTH: 12
<212> TYPE: PRT
<213> ORGANISM: Artificial Sequence
<220> FEATURE:
<223> OTHER INFORMATION: Synthetic Construct

<400> SEQUENCE: 60

Cys Asp Ala Gly Ser Val Arg Thr Asn Ala Pro Asp
1               5                   10

<210> SEQ ID NO 61
<211> LENGTH: 43
<212> TYPE: DNA
<213> ORGANISM: Artificial Sequence
<220> FEATURE:
<223> OTHER INFORMATION: Synthetic Construct

<400> SEQUENCE: 61
ggccgcatgc gacgctggca gtgtgcgcac caatgcacca gac                      43

<210> SEQ ID NO 62
<211> LENGTH: 43
<212> TYPE: DNA
<213> ORGANISM: Artificial Sequence
<220> FEATURE:
<223> OTHER INFORMATION: Synthetic Construct

<400> SEQUENCE: 62
cgcggtctgg tgcattggtg cgcacactgc cagcgtcgca tgc                      43

<210> SEQ ID NO 63
<211> LENGTH: 55
<212> TYPE: DNA
<213> ORGANISM: Artificial Sequence
<220> FEATURE:
<223> OTHER INFORMATION: Synthetic Construct

<400> SEQUENCE: 63
ggccgcagcc gcatgcgacg ctggcagtgt gcgcaccaat gcaccagacg cggca         55

<210> SEQ ID NO 64
<211> LENGTH: 55
<212> TYPE: DNA
<213> ORGANISM: Artificial Sequence
<220> FEATURE:
<223> OTHER INFORMATION: Synthetic Construct

<400> SEQUENCE: 64
cgcgtgccgc gtctggtgca ttggtgcgca cactgccagc gtcgcatgcg gctgc         55

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Asp Ala Glu Phe Arg His Asp Ser Gly

<210> SEQ ID NO 66
<211> LENGTH: 61
<212> TYPE: DNA
<213> ORGANISM: Artificial Sequence
<220> FEATURE:
<223> OTHER INFORMATION: Synthetic Construct

<400> SEQUENCE: 66
ggccggcgga ggcggtgggg acgccgaatt cagacacgac agcggcggag gcggtggagg    60
g    61

<210> SEQ ID NO 67
<211> LENGTH: 61
<212> TYPE: DNA
<213> ORGANISM: Artificial Sequence
<220> FEATURE:
<223> OTHER INFORMATION: Synthetic Construct

<400> SEQUENCE: 67
cgcgccctcc accgcctccg ccgctgtcgt gtctgaattc ggcgtcccca ccgcctccgc    60
c    61

<210> SEQ ID NO 68
<211> LENGTH: 33
<212> TYPE: DNA
<213> ORGANISM: Artificial Sequence
<220> FEATURE:
<223> OTHER INFORMATION: Synthetic Construct

<400> SEQUENCE: 68
gtagccctgg aaactagaac cggtgcctgc gcc    33

<210> SEQ ID NO 69
<211> LENGTH: 33
<212> TYPE: DNA
<213> ORGANISM: Artificial Sequence
<220> FEATURE:
<223> OTHER INFORMATION: Synthetic Construct

<400> SEQUENCE: 69
ggcgcaggca ccggttctag tttccagggc tac    33

<210> SEQ ID NO 70
<211> LENGTH: 53
<212> TYPE: DNA
<213> ORGANISM: Artificial Sequence
<220> FEATURE:
<223> OTHER INFORMATION: Synthetic Construct

<400> SEQUENCE: 70
ccaacctcca gagaggcaac gcggccgcaa ggcgcgccaa gcagctaccg cag    53

<210> SEQ ID NO 71
<211> LENGTH: 53
<212> TYPE: DNA
<213> ORGANISM: Artificial Sequence
<220> FEATURE:
<223> OTHER INFORMATION: Synthetic Construct

<400> SEQUENCE: 71
ctgcggtagc tgcttggcgc gccttgcggc cgcgttgcct ctctggaggt tgg    53

```
<210> SEQ ID NO 72
<211> LENGTH: 47
<212> TYPE: DNA
<213> ORGANISM: Artificial Sequence
<220> FEATURE:
<223> OTHER INFORMATION: Synthetic Construct

<400> SEQUENCE: 72
ggccgcatgc gacgctggca gtgtgcgcac caatgcacca gacgcgg         47

<210> SEQ ID NO 73
<211> LENGTH: 47
<212> TYPE: DNA
<213> ORGANISM: Artificial Sequence
<220> FEATURE:
<223> OTHER INFORMATION: Synthetic Construct

<400> SEQUENCE: 73
cgcgccgcgt ctggtgcatt ggtgcgcaca ctgccagcgt cgcatgc         47

<210> SEQ ID NO 74
<211> LENGTH: 62
<212> TYPE: DNA
<213> ORGANISM: Artificial Sequence
<220> FEATURE:
<223> OTHER INFORMATION: Synthetic Construct

<400> SEQUENCE: 74
ggccgcagcg gcgtgcgacg ctggcagtgt gcgcaccaat gcaccagacg cggcggcggc    60
gg                                                                  62

<210> SEQ ID NO 75
<211> LENGTH: 62
<212> TYPE: DNA
<213> ORGANISM: Artificial Sequence
<220> FEATURE:
<223> OTHER INFORMATION: Synthetic Construct

<400> SEQUENCE: 75
cgcgccgccg ccgccgcgtc tggtgcattg gtgcgcacac tgccagcgtc gcacgccgct    60
gc                                                                  62

<210> SEQ ID NO 76
<211> LENGTH: 68
<212> TYPE: DNA
<213> ORGANISM: Artificial Sequence
<220> FEATURE:
<223> OTHER INFORMATION: Synthetic Construct

<400> SEQUENCE: 76
ggccgcaggc ggaggggag gcgacgccga gttcagacac gacagcggcg gcggaggggg     60
aggcgcgg                                                            68

<210> SEQ ID NO 77
<211> LENGTH: 68
<212> TYPE: DNA
<213> ORGANISM: Artificial Sequence
<220> FEATURE:
<223> OTHER INFORMATION: Synthetic Construct

<400> SEQUENCE: 77
cgcgccgcgc ctcccctcc gccgccgctg tcgtgtctga actcggcgtc gcctcccct      60 ccgcctgc                                                            68
```

<210> SEQ ID NO 78
<211> LENGTH: 30
<212> TYPE: DNA
<213> ORGANISM: Artificial Sequence
<220> FEATURE:
<223> OTHER INFORMATION: Synthetic Construct

<400> SEQUENCE: 78
tctagagggc actcttccgt ggtctggtgg                              30

<210> SEQ ID NO 79
<211> LENGTH: 33
<212> TYPE: DNA
<213> ORGANISM: Artificial Sequence
<220> FEATURE:
<223> OTHER INFORMATION: Synthetic Construct

<400> SEQUENCE: 79
tctagagcaa aaagggggct cgtccctgtt tcc                          33

<210> SEQ ID NO 80
<211> LENGTH: 28
<212> TYPE: DNA
<213> ORGANISM: Artificial Sequence
<220> FEATURE:
<223> OTHER INFORMATION: Synthetic Construct

<400> SEQUENCE: 80
ggtgaatccg gggccggcca tggcaagc                                28

<210> SEQ ID NO 81
<211> LENGTH: 28
<212> TYPE: DNA
<213> ORGANISM: Artificial Sequence
<220> FEATURE:
<223> OTHER INFORMATION: Synthetic Construct

<400> SEQUENCE: 81
gcttgccatg gccggccccg gattcacc                                28

<210> SEQ ID NO 82
<211> LENGTH: 24
<212> TYPE: PRT
<213> ORGANISM: Artificial Sequence
<220> FEATURE:
<223> OTHER INFORMATION: Synthetic Construct

<400> SEQUENCE: 82

Ala Ala Ala Gly Gly Gly Gly Gly Asp Ala Glu Phe Arg His Asp Ser
1               5                   10                  15

Gly Gly Gly Gly Gly Gly Ala Ala
            20

<210> SEQ ID NO 83
<211> LENGTH: 24
<212> TYPE: PRT
<213> ORGANISM: Artificial Sequence
<220> FEATURE:
<223> OTHER INFORMATION: Synthetic Construct

<400> SEQUENCE: 83

Ala Ala Gly Gly Gly Gly Gly Asp Ala Glu Phe Arg His Asp Ser Gly
1               5                   10                  15

Gly Gly Gly Gly Gly Arg Ala Ala
            20

<210> SEQ ID NO 84
<211> LENGTH: 11
<212> TYPE: PRT
<213> ORGANISM: Artificial Sequence
<220> FEATURE:
<223> OTHER INFORMATION: Synthetic Construct

<400> SEQUENCE: 84

Ala Cys Asp Cys Arg Gly Asp Cys Phe Cys Ala
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct

<400> SEQUENCE: 85

Glu Asp Gly Gln Val Met Asp Val Asp Leu Ser
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Synthetic Construct

<400> SEQUENCE: 86

Glu Lys Gln Arg Asn Gly Thr Leu Thr
1               5

<210> SEQ ID NO 87
<211> LENGTH: 17
<212> TYPE: PRT
<213> ORGANISM: Artificial Sequence
<220> FEATURE:
<223> OTHER INFORMATION: Synthetic Construct

<400> SEQUENCE: 87

Thr Tyr Gln Cys Arg Val Thr His Pro His Leu Pro Arg Ala Leu Met
1               5                   10                  15

Arg

<210> SEQ ID NO 88
<211> LENGTH: 14
<212> TYPE: PRT
<213> ORGANISM: Artificial Sequence
<220> FEATURE:
<223> OTHER INFORMATION: Synthetic Construct

<400> SEQUENCE: 88

Arg His Ser Thr Thr Gln Pro Arg Lys Thr Lys Gly Ser Gly
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic Construct

<400> SEQUENCE: 89

Asp Ser Asn Pro Arg Gly Val Ser Ala Tyr Leu Ser Arg

```
<210> SEQ ID NO 90
<211> LENGTH: 13
<212> TYPE: PRT
<213> ORGANISM: Artificial Sequence
<220> FEATURE:
<223> OTHER INFORMATION: Synthetic Construct

<400> SEQUENCE: 90

Thr Ile Thr Cys Leu Val Val Asp Leu Ala Pro Ser Lys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic Construct

<400> SEQUENCE: 91

Lys Thr Lys Gly Ser Gly Phe Phe Val Phe
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic Construct

<400> SEQUENCE: 92

Thr His Pro His Leu Pro Arg Ala Leu Met Arg Ser
1               5                   10

<210> SEQ ID NO 93
<211> LENGTH: 23
<212> TYPE: PRT
<213> ORGANISM: Artificial Sequence
<220> FEATURE:
<223> OTHER INFORMATION: Synthetic Construct

<400> SEQUENCE: 93

Gly Glu Thr Tyr Gln Cys Arg Val Thr His Pro His Leu Pro Arg Ala
1               5                   10                  15

Leu Met Arg Ser Thr Thr Lys
            20

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Leu Pro Arg Ala Leu Met Arg Ser
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct

<400> SEQUENCE: 95
```

```
Ile Asn His Arg Gly Tyr Trp Val
1               5

<210> SEQ ID NO 96
<211> LENGTH: 17
<212> TYPE: PRT
<213> ORGANISM: Artificial Sequence
<220> FEATURE:
<223> OTHER INFORMATION: Synthetic Construct

<400> SEQUENCE: 96

Ala Lys Ala Val Ser Asn Leu Thr Glu Ser Arg Ser Glu Ser Leu Gln
1               5                   10                  15

Ser

<210> SEQ ID NO 97
<211> LENGTH: 13
<212> TYPE: PRT
<213> ORGANISM: Artificial Sequence
<220> FEATURE:
<223> OTHER INFORMATION: Synthetic Construct

<400> SEQUENCE: 97

Ser Leu Thr Gly Asp Glu Phe Lys Lys Val Leu Glu Thr
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic Construct

<400> SEQUENCE: 98

Arg Glu Ala Val Ala Tyr Arg Phe Glu Glu Asp
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic Construct

<400> SEQUENCE: 99

Ile Asn Pro Glu Ile Ile Thr Leu Asp Gly
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Synthetic Construct

<400> SEQUENCE: 100

Asp Ile Ser Val Thr Gly Ala Pro Val Ile Thr Ala Thr Tyr Leu
1               5                   10                  15

<210> SEQ ID NO 101
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 101

Asp Ile Ser Val Thr Gly Ala Pro Val Ile Thr Ala
1               5                   10

<210> SEQ ID NO 102
<211> LENGTH: 17
<212> TYPE: PRT
<213> ORGANISM: Artificial Sequence
<220> FEATURE:
<223> OTHER INFORMATION: Synthetic Construct

<400> SEQUENCE: 102

Pro Lys Thr Val Ser Asn Leu Thr Glu Ser Ser Ser Glu Ser Val Gln
1               5                   10                  15

Ser

<210> SEQ ID NO 103
<211> LENGTH: 13
<212> TYPE: PRT
<213> ORGANISM: Artificial Sequence
<220> FEATURE:
<223> OTHER INFORMATION: Synthetic Construct

<400> SEQUENCE: 103

Ser Leu Met Gly Asp Glu Phe Lys Ala Val Leu Glu Thr
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic Construct

<400> SEQUENCE: 104

Gln His Ser Val Ala Tyr Thr Phe Glu Glu Asp
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic Construct

<400> SEQUENCE: 105

Ile Asn Pro Glu Ile Ile Thr Arg Asp Gly
1               5                   10

<210> SEQ ID NO 106
<211> LENGTH: 15
<212> TYPE: PRT
<213> ORGANISM: Artificial Sequence
<220> FEATURE:
<223> OTHER INFORMATION: Synthetic Construct

<400> SEQUENCE: 106

Asp Ile Ser Leu Thr Gly Asp Pro Val Ile Thr Ala Ser Tyr Leu
1               5                   10                  15

<210> SEQ ID NO 107
<211> LENGTH: 12
<212> TYPE: PRT
<213> ORGANISM: Artificial Sequence
<220> FEATURE:
<223> OTHER INFORMATION: Synthetic Construct
```

<400> SEQUENCE: 107

Asp Ile Ser Leu Thr Gly Asp Pro Val Ile Thr Ala
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic Construct

<400> SEQUENCE: 108

Asp Gln Ser Ile Asp Phe Glu Ile Asp Ser Ala
1               5                   10

<210> SEQ ID NO 109
<211> LENGTH: 20
<212> TYPE: PRT
<213> ORGANISM: Artificial Sequence
<220> FEATURE:
<223> OTHER INFORMATION: Synthetic Construct

<400> SEQUENCE: 109

Lys Asn Val Ser Glu Asp Leu Pro Leu Pro Thr Phe Ser Pro Thr Leu
1               5                   10                  15

Leu Gly Asp Ser
            20

<210> SEQ ID NO 110
<211> LENGTH: 11
<212> TYPE: PRT
<213> ORGANISM: Artificial Sequence
<220> FEATURE:
<223> OTHER INFORMATION: Synthetic Construct

<400> SEQUENCE: 110

Lys Asn Val Ser Glu Asp Leu Pro Leu Pro Thr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Construct

<400> SEQUENCE: 111

Cys Asp Ser Gly Arg Val Arg Thr Asp Ala Pro Asp
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthetic Construct

<400> SEQUENCE: 112

Phe Pro Glu His Leu Leu Val Asp Phe Leu Gln Ser Leu Ser
1               5                   10

<210> SEQ ID NO 113
<211> LENGTH: 16
<212> TYPE: PRT
<213> ORGANISM: Artificial Sequence

```
<220> FEATURE:
<223> OTHER INFORMATION: Synthetic Construct

<400> SEQUENCE: 113

His Tyr Ala Ala Ala Gln Trp Asp Phe Gly Asn Thr Met Cys Gln Leu
1               5                   10                  15

<210> SEQ ID NO 114
<211> LENGTH: 13
<212> TYPE: PRT
<213> ORGANISM: Artificial Sequence
<220> FEATURE:
<223> OTHER INFORMATION: Synthetic Construct

<400> SEQUENCE: 114

Tyr Ala Ala Gln Trp Asp Phe Gly Asn Thr Met Cys Gln
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct

<400> SEQUENCE: 115

Arg Ser Gln Lys Glu Gly Leu His Tyr Thr
1               5                   10

<210> SEQ ID NO 116
<211> LENGTH: 20
<212> TYPE: PRT
<213> ORGANISM: Artificial Sequence
<220> FEATURE:
<223> OTHER INFORMATION: Synthetic Construct

<400> SEQUENCE: 116

Ser Ser Arg Thr Pro Ser Asp Lys Pro Val Ala His Val Val Ala Asn
1               5                   10                  15

Pro Gln Ala Glu
            20

<210> SEQ ID NO 117
<211> LENGTH: 16
<212> TYPE: PRT
<213> ORGANISM: Artificial Sequence
<220> FEATURE:
<223> OTHER INFORMATION: Synthetic Construct

<400> SEQUENCE: 117

Ser Arg Thr Pro Ser Asp Lys Pro Val Ala His Val Val Ala Asn Pro
1               5                   10                  15

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct

<400> SEQUENCE: 118

Ser Ser Arg Thr Pro Ser Asp Lys Pro
1               5

<210> SEQ ID NO 119
<211> LENGTH: 14
```

```
<212> TYPE: PRT
<213> ORGANISM: Artificial Sequence
<220> FEATURE:
<223> OTHER INFORMATION: Synthetic Construct

<400> SEQUENCE: 119

Asn Ala Asp Gly Asn Val Asp Tyr His Met Asn Ser Val Pro
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic Construct

<400> SEQUENCE: 120

Asp Gly Asn Val Asp Tyr His Met Asn Ser Val
1               5                   10

<210> SEQ ID NO 121
<211> LENGTH: 16
<212> TYPE: PRT
<213> ORGANISM: Artificial Sequence
<220> FEATURE:
<223> OTHER INFORMATION: Synthetic Construct

<400> SEQUENCE: 121

Arg Ser Phe Lys Glu Phe Leu Gln Ser Ser Leu Arg Ala Leu Arg Gln
1               5                   10                  15

<210> SEQ ID NO 122
<211> LENGTH: 11
<212> TYPE: PRT
<213> ORGANISM: Artificial Sequence
<220> FEATURE:
<223> OTHER INFORMATION: Synthetic Construct

<400> SEQUENCE: 122

Phe Lys Glu Phe Leu Gln Ser Ser Leu Arg Ala
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic Construct

<400> SEQUENCE: 123

Gln Met Trp Ala Pro Gln Trp Gly Pro Asp
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic Construct

<400> SEQUENCE: 124

Arg Thr Thr Asn Pro Val Ala Thr Glu Gln
1               5                   10

<210> SEQ ID NO 125
<211> LENGTH: 10
<212> TYPE: PRT
```

<213> ORGANISM: Artificial Sequence
<220> FEATURE:
<223> OTHER INFORMATION: Synthetic Construct

<400> SEQUENCE: 125

Phe Gln Ser Ser Ser Thr Asp Pro Ala Thr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic Construct

<400> SEQUENCE: 126

Lys Leu Lys Leu Leu Leu Leu Leu Lys Leu Lys
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic Construct

<400> SEQUENCE: 127

Asp Gln Ser Val Asp Phe Glu Ile Asp Ser Ala
1               5                   10

<210> SEQ ID NO 128
<211> LENGTH: 76
<212> TYPE: DNA
<213> ORGANISM: Artificial Sequence
<220> FEATURE:
<223> OTHER INFORMATION: Synthetic Construct

<400> SEQUENCE: 128
ggccggcggt ggagccaagg ccgtgagcaa cctgaccgag agcagaagcg agagcctgca    60
gagcggtggc ggtgga                                                   76

<210> SEQ ID NO 129
<211> LENGTH: 76
<212> TYPE: DNA
<213> ORGANISM: Artificial Sequence
<220> FEATURE:
<223> OTHER INFORMATION: Synthetic Construct

<400> SEQUENCE: 129
cgcgtccacc gccaccgctc tgcaggctct cgcttctgct ctcggtcagg ttgctcacgg    60
ccttggctcc accgcc                                                   76

<210> SEQ ID NO 130
<211> LENGTH: 64
<212> TYPE: DNA
<213> ORGANISM: Artificial Sequence
<220> FEATURE:
<223> OTHER INFORMATION: Synthetic Construct

<400> SEQUENCE: 130
ggccggcggt ggaagcctga ccggcgacga attcaagaag gtgctggaga ccggtggcgg    60
tgga                                                                64

<210> SEQ ID NO 131

```
<211> LENGTH: 64
<212> TYPE: DNA
<213> ORGANISM: Artificial Sequence
<220> FEATURE:
<223> OTHER INFORMATION: Synthetic Construct

<400> SEQUENCE: 131
cgcgtccacc gccaccggtc tccagcacct tcttgaattc gtcgccggtc aggcttccac    60
cgcc                                                                 64

<210> SEQ ID NO 132
<211> LENGTH: 58
<212> TYPE: DNA
<213> ORGANISM: Artificial Sequence
<220> FEATURE:
<223> OTHER INFORMATION: Synthetic Construct

<400> SEQUENCE: 132
ggccggcggt ggaagagagg ccgtggccta cagattcgaa gaggacggtg gcggtgga     58

<210> SEQ ID NO 133
<211> LENGTH: 58
<212> TYPE: DNA
<213> ORGANISM: Artificial Sequence
<220> FEATURE:
<223> OTHER INFORMATION: Synthetic Construct

<400> SEQUENCE: 133
cgcgtccacc gccaccgtcc tcttcgaatc tgtaggccac ggcctctctt ccaccgcc     58

<210> SEQ ID NO 134
<211> LENGTH: 55
<212> TYPE: DNA
<213> ORGANISM: Artificial Sequence
<220> FEATURE:
<223> OTHER INFORMATION: Synthetic Construct

<400> SEQUENCE: 134
ggccggcggt ggaatcaacc ccgagatcat caccctggac ggcggtggcg gtgga        55

<210> SEQ ID NO 135
<211> LENGTH: 55
<212> TYPE: DNA
<213> ORGANISM: Artificial Sequence
<220> FEATURE:
<223> OTHER INFORMATION: Synthetic Construct

<400> SEQUENCE: 135
cgcgtccacc gccaccgccg tccagggtga tgatctcggg gttgattcca ccgcc        55

<210> SEQ ID NO 136
<211> LENGTH: 70
<212> TYPE: DNA
<213> ORGANISM: Artificial Sequence
<220> FEATURE:
<223> OTHER INFORMATION: Synthetic Construct

<400> SEQUENCE: 136
ggccggcggt ggagacatca gcgtgaccgg tgcacccgtg atcaccgcca cctacctggg    60
tggcggtgga                                                           70

<210> SEQ ID NO 137
<211> LENGTH: 70
<212> TYPE: DNA
<213> ORGANISM: Artificial Sequence
```

```
<220> FEATURE:
<223> OTHER INFORMATION: Synthetic Construct

<400> SEQUENCE: 137
cgcgtccacc gccacccagg taggtggcgg tgatcacggg tgcaccggtc acgctgatgt    60
ctccaccgcc                                                            70

<210> SEQ ID NO 138
<211> LENGTH: 61
<212> TYPE: DNA
<213> ORGANISM: Artificial Sequence
<220> FEATURE:
<223> OTHER INFORMATION: Synthetic Construct

<400> SEQUENCE: 138
ggccggcggt ggagacatca gcgtgaccgg tgcaccgtg atcaccgccg gtggcggtgg     60
a                                                                     61

<210> SEQ ID NO 139
<211> LENGTH: 61
<212> TYPE: DNA
<213> ORGANISM: Artificial Sequence
<220> FEATURE:
<223> OTHER INFORMATION: Synthetic Construct

<400> SEQUENCE: 139
cgcgtccacc gccaccggcg gtgatcacgg gtgcaccggt cacgctgatg tctccaccgc    60
c                                                                     61

<210> SEQ ID NO 140
<211> LENGTH: 58
<212> TYPE: DNA
<213> ORGANISM: Artificial Sequence
<220> FEATURE:
<223> OTHER INFORMATION: Synthetic Construct

<400> SEQUENCE: 140
ggccggcggt ggagaccaga gcgtggactt cgagatcgac agcgccggtg cggtgga       58

<210> SEQ ID NO 141
<211> LENGTH: 58
<212> TYPE: DNA
<213> ORGANISM: Artificial Sequence
<220> FEATURE:
<223> OTHER INFORMATION: Synthetic Construct

<400> SEQUENCE: 141
cgcgtccacc gccaccggcg ctgtcgatct cgaagtccac gctctggtct ccaccgcc      58

<210> SEQ ID NO 142
<211> LENGTH: 20
<212> TYPE: PRT
<213> ORGANISM: Artificial Sequence
<220> FEATURE:
<223> OTHER INFORMATION: Synthetic Construct

<400> SEQUENCE: 142

Ser Ser Gln Asn Ser Ser Asp Lys Pro Val Ala His Val Val Ala Asn
1               5                   10                  15

His Gln Val Glu
            20

<210> SEQ ID NO 143
```

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 143

Asn Ala Glu Gly Lys Leu Asp His His Met Asn Ser Val Leu
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Synthetic Construct

<400> SEQUENCE: 144

Leu Glu Glu Phe Leu Lys Val Thr Leu Arg Ser
1               5                   10

<210> SEQ ID NO 145
<211> LENGTH: 88
<212> TYPE: DNA
<213> ORGANISM: Artificial Sequence
<220> FEATURE:
<223> OTHER INFORMATION: Synthetic Construct

<400> SEQUENCE: 145
ggccgccggt ggaggcagca gccagaacag cagcgacaag cccgtggccc acgtggtggc     60
taaccaccag gtggagggcg gtggaggg                                       88

<210> SEQ ID NO 146
<211> LENGTH: 70
<212> TYPE: DNA
<213> ORGANISM: Artificial Sequence
<220> FEATURE:
<223> OTHER INFORMATION: Synthetic Construct

<400> SEQUENCE: 146
ggccgccggt ggaggcaacg ccgagggcaa gcttgaccac cacatgaaca gcgtgctggg     60
cggtggaggg                                                           70

<210> SEQ ID NO 147
<211> LENGTH: 61
<212> TYPE: DNA
<213> ORGANISM: Artificial Sequence
<220> FEATURE:
<223> OTHER INFORMATION: Synthetic Construct

<400> SEQUENCE: 147
ggccgccggt ggaggcctgg aggaattcct gaaggtgacc ctgagaagcg gcggtggagg     60
g                                                                    61

<210> SEQ ID NO 148
<211> LENGTH: 88
<212> TYPE: DNA
<213> ORGANISM: Artificial Sequence
<220> FEATURE:
<223> OTHER INFORMATION: Synthetic Construct

<400> SEQUENCE: 148
cgcgccctcc accgccctcc acctggtggt tagccaccac gtgggccacg gcttgtcgc      60 tgctgttctg gctgctgcct ccaccggc                                       88
```

<210> SEQ ID NO 149
<211> LENGTH: 70
<212> TYPE: DNA
<213> ORGANISM: Artificial Sequence
<220> FEATURE:
<223> OTHER INFORMATION: Synthetic Construct

<400> SEQUENCE: 149
cgcgccctcc accgcccagc acgctgttca tgtggtggtc aagcttgccc tcggcgttgc    60
ctccaccggc                                                            70

<210> SEQ ID NO 150
<211> LENGTH: 61
<212> TYPE: DNA
<213> ORGANISM: Artificial Sequence
<220> FEATURE:
<223> OTHER INFORMATION: Synthetic Construct

<400> SEQUENCE: 150
cgcgccctcc accgccgctt ctcagggtca ccttcaggaa ttcctccagg cctccaccgg    60
c                                                                     61

<210> SEQ ID NO 151
<211> LENGTH: 16
<212> TYPE: PRT
<213> ORGANISM: Artificial Sequence
<220> FEATURE:
<223> OTHER INFORMATION: Synthetic Construct

<400> SEQUENCE: 151

Ser Gln Asn Ser Ser Asp Lys Pro Val Ala His Val Val Ala Asn His
1               5                   10                  15

<210> SEQ ID NO 152
<211> LENGTH: 9
<212> TYPE: PRT
<213> ORGANISM: Artificial Sequence
<220> FEATURE:
<223> OTHER INFORMATION: Synthetic Construct

<400> SEQUENCE: 152

Ser Ser Gln Asn Ser Ser Asp Lys Pro
1               5

<210> SEQ ID NO 153
<211> LENGTH: 11
<212> TYPE: PRT
<213> ORGANISM: Artificial Sequence
<220> FEATURE:
<223> OTHER INFORMATION: Synthetic Construct

<400> SEQUENCE: 153

Glu Gly Lys Leu Asp His His Met Asn Ser Val
1               5                   10

<210> SEQ ID NO 154
<211> LENGTH: 16
<212> TYPE: PRT
<213> ORGANISM: Artificial Sequence
<220> FEATURE:
<223> OTHER INFORMATION: Synthetic Construct

<400> SEQUENCE: 154

Lys Ser Leu Glu Glu Phe Leu Lys Val Thr Leu Arg Ser Thr Arg Gln

<210> SEQ ID NO 155
<211> LENGTH: 14
<212> TYPE: PRT
<213> ORGANISM: Artificial Sequence
<220> FEATURE:
<223> OTHER INFORMATION: Synthetic Construct

<400> SEQUENCE: 155

Cys Ser Leu Thr Gly Asp Glu Phe Lys Lys Val Leu Glu Thr
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Synthetic Construct

<400> SEQUENCE: 156

Cys Arg Glu Ala Val Ala Tyr Arg Phe Glu Glu Asp
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Synthetic Construct

<400> SEQUENCE: 157

Cys Ile Asn Pro Glu Ile Ile Thr Leu Asp Gly
1               5                   10

<210> SEQ ID NO 158
<211> LENGTH: 16
<212> TYPE: PRT
<213> ORGANISM: Artificial Sequence
<220> FEATURE:
<223> OTHER INFORMATION: Synthetic Construct

<400> SEQUENCE: 158

Cys Asp Ile Ser Val Thr Gly Ala Pro Val Ile Thr Ala Thr Tyr Leu
1               5                   10                  15

<210> SEQ ID NO 159
<211> LENGTH: 32
<212> TYPE: DNA
<213> ORGANISM: Artificial Sequence
<220> FEATURE:
<223> OTHER INFORMATION: Synthetic Construct

<400> SEQUENCE: 159
ggggaattca tgtcccaaag gcgcctccta cg                                    32

<210> SEQ ID NO 160
<211> LENGTH: 34
<212> TYPE: DNA
<213> ORGANISM: Artificial Sequence
<220> FEATURE:
<223> OTHER INFORMATION: Synthetic Construct

<400> SEQUENCE: 160
gggggatccc tagctcaggc tctggaggaa atcc                                  34

```
<210> SEQ ID NO 161
<211> LENGTH: 11
<212> TYPE: PRT
<213> ORGANISM: Artificial Sequence
<220> FEATURE:
<223> OTHER INFORMATION: Synthetic Construct

<400> SEQUENCE: 161

Val Asn Leu Thr Trp Ser Arg Ala Ser Gly Cys
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Synthetic Construct

<400> SEQUENCE: 162

Cys Asp Ser Asn Pro Arg Gly Val Ser Ala Tyr Leu Ser Arg
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Synthetic Construct

<400> SEQUENCE: 163

Cys Glu Asp Gly Gln Val Met Asp Val Asp Leu Ser
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Synthetic Construct

<400> SEQUENCE: 164

Cys Glu Lys Gln Arg Asn Gly Thr Leu Thr
1               5                   10

<210> SEQ ID NO 165
<211> LENGTH: 31
<212> TYPE: PRT
<213> ORGANISM: Artificial Sequence
<220> FEATURE:
<223> OTHER INFORMATION: Synthetic Construct

<400> SEQUENCE: 165

Ile Asp Gln Tyr Leu Tyr Tyr Leu Ser Arg Thr Asn Thr Pro Ser Gly
1               5                   10                  15

Thr Thr Thr Gln Ser Arg Leu Gln Phe Ser Gln Ala Gly Ala Ser
            20                  25                  30

<210> SEQ ID NO 166
<211> LENGTH: 31
<212> TYPE: PRT
<213> ORGANISM: Artificial Sequence
<220> FEATURE:
<223> OTHER INFORMATION: Synthetic Construct

<400> SEQUENCE: 166

Leu Val Asp Gln Tyr Leu Tyr Arg Phe Val Ser Thr Asn Asn Thr Gly
1               5                   10                  15
```

```
Gly Val Gln Phe Asn Lys Asn Leu Ala Gly Arg Tyr Ala Asn Thr
            20                  25                  30
```

<210> SEQ ID NO 167
<211> LENGTH: 31
<212> TYPE: PRT
<213> ORGANISM: Artificial Sequence
<220> FEATURE:
<223> OTHER INFORMATION: Synthetic Construct

<400> SEQUENCE: 167

```
Ile Asp Gln Tyr Leu Tyr Tyr Leu Asn Arg Thr Gln Asn Gln Ser Gly
1               5                   10                  15

Ser Ala Gln Asn Lys Asp Leu Leu Phe Ser Arg Gly Ser Pro Ala
            20                  25                  30
```

<210> SEQ ID NO 168
<211> LENGTH: 31
<212> TYPE: PRT
<213> ORGANISM: Artificial Sequence
<220> FEATURE:
<223> OTHER INFORMATION: Synthetic Construct

<400> SEQUENCE: 168

```
Ile Asp Gln Tyr Leu Tyr Tyr Leu Asn Arg Thr Gln Asn Gln Ser Gly
1               5                   10                  15

Ser Ala Gln Asn Lys Asp Leu Leu Phe Ser Arg Gly Ser Pro Ala
            20                  25                  30
```

<210> SEQ ID NO 169
<211> LENGTH: 31
<212> TYPE: PRT
<213> ORGANISM: Artificial Sequence
<220> FEATURE:
<223> OTHER INFORMATION: Synthetic Construct

<400> SEQUENCE: 169

```
Ile Asp Gln Tyr Leu Tyr Tyr Leu Ser Arg Thr Gln Thr Thr Gly Gly
1               5                   10                  15

Thr Ala Asn Thr Gln Thr Leu Gly Phe Ser Gly Gly Pro Asn
            20                  25                  30
```

<210> SEQ ID NO 170
<211> LENGTH: 31
<212> TYPE: PRT
<213> ORGANISM: Artificial Sequence
<220> FEATURE:
<223> OTHER INFORMATION: Synthetic Construct

<400> SEQUENCE: 170

```
Ile Asp Gln Tyr Leu Tyr Tyr Leu Ser Arg Thr Gln Ser Thr Gly Gly
1               5                   10                  15

Thr Gln Gly Thr Gln Gln Leu Leu Phe Ser Gln Ala Gly Pro Ala
            20                  25                  30
```

<210> SEQ ID NO 171
<211> LENGTH: 31
<212> TYPE: PRT
<213> ORGANISM: Artificial Sequence
<220> FEATURE:
<223> OTHER INFORMATION: Synthetic Construct

<400> SEQUENCE: 171

```
Asp Gln Tyr Leu Tyr Tyr Leu Asn Arg Thr Gln Gly Thr Thr Ser Gly
```

```
                1               5                  10                  15
Thr Thr Asn Gln Ser Arg Leu Leu Phe Ser Gln Ala Gly Pro Gln
                20                  25                  30

<210> SEQ ID NO 172
<211> LENGTH: 31
<212> TYPE: PRT
<213> ORGANISM: Artificial Sequence
<220> FEATURE:
<223> OTHER INFORMATION: Synthetic Construct

<400> SEQUENCE: 172

Asp Gln Tyr Leu Tyr Tyr Leu Ala Arg Thr Gln Ser Asn Pro Gly Gly
1               5                  10                  15

Thr Ala Gly Asn Arg Glu Leu Gln Phe Tyr Gln Gly Gly Pro Ser
                20                  25                  30

<210> SEQ ID NO 173
<211> LENGTH: 31
<212> TYPE: PRT
<213> ORGANISM: Artificial Sequence
<220> FEATURE:
<223> OTHER INFORMATION: Synthetic Construct

<400> SEQUENCE: 173

Pro Leu Ile Asp Gln Tyr Leu Trp Gly Leu Gln Ser Thr Thr Gly
1               5                  10                  15

Thr Thr Leu Asn Ala Gly Thr Ala Thr Thr Asn Phe Thr Lys Leu
                20                  25                  30

<210> SEQ ID NO 174
<211> LENGTH: 31
<212> TYPE: PRT
<213> ORGANISM: Artificial Sequence
<220> FEATURE:
<223> OTHER INFORMATION: Synthetic Construct

<400> SEQUENCE: 174

Pro Leu Leu Asp Gln Tyr Leu Trp His Leu Gln Ser Thr Thr Ser Gly
1               5                  10                  15

Glu Thr Leu Asn Gln Gly Asn Ala Ala Thr Thr Phe Gly Lys Ile
                20                  25                  30

<210> SEQ ID NO 175
<211> LENGTH: 31
<212> TYPE: PRT
<213> ORGANISM: Artificial Sequence
<220> FEATURE:
<223> OTHER INFORMATION: Synthetic Construct

<400> SEQUENCE: 175

Pro Leu Leu Asp Gln Tyr Leu Trp Glu Leu Gln Ser Thr Thr Ser Gly
1               5                  10                  15

Gly Thr Leu Asn Gln Gly Asn Ser Ala Thr Asn Phe Ala Lys Leu
                20                  25                  30

<210> SEQ ID NO 176
<211> LENGTH: 34
<212> TYPE: PRT
<213> ORGANISM: Artificial Sequence
<220> FEATURE:
<223> OTHER INFORMATION: Synthetic Construct

<400> SEQUENCE: 176
```

```
Pro Phe Leu Asn Ser Leu Pro Gln Ser Glu Gly Ala Thr Asn Phe Gly
1               5                   10                  15

Asp Ile Gly Val Gln Gln Asp Lys Arg Arg Gly Val Thr Gln Met Gly
            20                  25                  30

Asn Thr
```

<210> SEQ ID NO 177
<211> LENGTH: 34
<212> TYPE: PRT
<213> ORGANISM: Artificial Sequence
<220> FEATURE:
<223> OTHER INFORMATION: Synthetic Construct

<400> SEQUENCE: 177

```
Pro Phe Leu Asn Ser Leu Pro Gln Ser Glu Gly Ala Thr Asn Phe Gly
1               5                   10                  15

Asp Ile Gly Val Gln Gln Asp Lys Arg Arg Gly Val Thr Gln Met Gly
            20                  25                  30

Asn Thr
```

<210> SEQ ID NO 178
<211> LENGTH: 31
<212> TYPE: PRT
<213> ORGANISM: Artificial Sequence
<220> FEATURE:
<223> OTHER INFORMATION: Synthetic Construct

<400> SEQUENCE: 178

```
Asn Pro Leu Tyr Gly Ser Arg Leu Gly Val Pro Asp Thr Leu Gly Gly
1               5                   10                  15

Asp Pro Lys Phe Arg Ser Leu Thr His Glu Asp His Ala Ile Gln
            20                  25                  30
```

<210> SEQ ID NO 179
<211> LENGTH: 31
<212> TYPE: PRT
<213> ORGANISM: Artificial Sequence
<220> FEATURE:
<223> OTHER INFORMATION: Synthetic Construct

<400> SEQUENCE: 179

```
Leu Lys Asp Arg Gln Tyr Leu Leu Gln Pro Gly Pro Val Ser Ala Thr
1               5                   10                  15

Tyr Thr Glu Gly Glu Ala Ser Ser Leu Pro Ala Gln Asn Ile Leu
            20                  25                  30
```

<210> SEQ ID NO 180
<211> LENGTH: 34
<212> TYPE: PRT
<213> ORGANISM: Artificial Sequence
<220> FEATURE:
<223> OTHER INFORMATION: Synthetic Construct

<400> SEQUENCE: 180

```
Gln Pro Pro Leu Leu Ser Thr Phe Pro Glu Ala Asp Thr Asp Ala Gly
1               5                   10                  15

Thr Leu Thr Ala Gln Gly Ser Arg His Gly Ala Thr Gln Met Glu Val
            20                  25                  30

Asn Trp
```

<210> SEQ ID NO 181
<211> LENGTH: 736

```
<212> TYPE: PRT
<213> ORGANISM: adeno-associated virus 1

<400> SEQUENCE: 181

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

```
Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 182
<211> LENGTH: 736
<212> TYPE: PRT
<213> ORGANISM: adeno-associated virus 6

<400> SEQUENCE: 182

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
```

```
            35                  40                  45
Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70              75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
         115                 120                 125

Phe Gly Leu Val Glu Glu Gly Ala Lys Thr Ala Pro Gly Lys Lys Arg
     130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                 165                 170                 175

Gly Asp Ser Glu Ser Val Pro Asp Pro Gln Pro Leu Gly Glu Pro Pro
             180                 185                 190

Ala Thr Pro Ala Ala Val Gly Pro Thr Thr Met Ala Ser Gly Gly Gly
         195                 200                 205

Ala Pro Met Ala Asp Asn Asn Glu Gly Ala Asp Gly Val Gly Asn Ala
     210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Ser Ala Ser Thr Gly Ala Ser Asn Asp Asn His
             260                 265                 270

Tyr Phe Gly Tyr Ser Thr Pro Trp Gly Tyr Phe Asp Phe Asn Arg Phe
         275                 280                 285

His Cys His Phe Ser Pro Arg Asp Trp Gln Arg Leu Ile Asn Asn Asn
     290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                 325                 330                 335

Leu Thr Ser Thr Val Gln Val Phe Ser Asp Ser Glu Tyr Gln Leu Pro
             340                 345                 350

Tyr Val Leu Gly Ser Ala His Gln Gly Cys Leu Pro Pro Phe Pro Ala
         355                 360                 365

Asp Val Phe Met Ile Pro Gln Tyr Gly Tyr Leu Thr Leu Asn Asn Gly
     370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                 405                 410                 415

Glu Asp Val Pro Phe His Ser Ser Tyr Ala His Ser Gln Ser Leu Asp
             420                 425                 430

Arg Leu Met Asn Pro Leu Ile Asp Gln Tyr Leu Tyr Tyr Leu Asn Arg
         435                 440                 445

Thr Gln Asn Gln Ser Gly Ser Ala Gln Asn Lys Asp Leu Leu Phe Ser
     450                 455                 460
```

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 183
<211> LENGTH: 735
<212> TYPE: PRT
<213> ORGANISM: adeno-associated virus 2

<400> SEQUENCE: 183

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly

```
                100                 105                 110
Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
            450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525
```

-continued

```
Asp Glu Glu Lys Phe Phe Pro Gln Ser Gly Val Leu Ile Phe Gly Lys
            530                 535                 540
Gln Gly Ser Glu Lys Thr Asn Val Asp Ile Glu Lys Val Met Ile Thr
545                 550                 555                 560
Asp Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
            595                 600                 605
Arg Asp Val Tyr Leu Gln Gly Pro Ile Trp Ala Lys Ile Pro His Thr
            610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 184
<211> LENGTH: 736
<212> TYPE: PRT
<213> ORGANISM: adeno-associated virus 3b

<400> SEQUENCE: 184

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Val Pro Gln Pro
            20                  25                  30
Lys Ala Asn Gln Gln His Gln Asp Asn Arg Arg Gly Leu Val Leu Pro
        35                  40                  45
Gly Tyr Lys Tyr Leu Gly Pro Gly Asn Gly Leu Asp Lys Gly Glu Pro
50                  55                  60
Val Asn Glu Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Ile Leu Glu Pro
        115                 120                 125
Leu Gly Leu Val Glu Glu Ala Lys Thr Ala Pro Gly Lys Lys Arg
        130                 135                 140
Pro Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
```

-continued

```
            165                 170                 175
Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
            290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
            485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
            565                 570                 575

Tyr Gly Thr Val Ala Asn Asn Leu Gln Ser Ser Asn Thr Ala Pro Thr
            580                 585                 590
```

-continued

```
Thr Arg Thr Val Asn Asp Gln Gly Ala Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly His Phe His Pro Ser Pro Leu Met Gly Gly Phe Gly Leu
625                 630                 635                 640
Lys His Pro Pro Gln Ile Met Ile Lys Asn Thr Pro Val Pro Ala
            645                 650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 185
<211> LENGTH: 737
<212> TYPE: PRT
<213> ORGANISM: adeno-associated virus 7

<400> SEQUENCE: 185

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asn Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Ala Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Ser Val Gly Ser Gly Thr Val Ala Ala Gly Gly
        195                 200                 205
Gly Ala Pro Met Ala Asp Asn Asn Glu Gly Ala Asp Gly Val Gly Asn
    210                 215                 220
Ala Ser Gly Asn Trp His Cys Asp Ser Thr Trp Leu Gly Asp Arg Val
```

-continued

```
            225                 230                 235                 240
        Ile Thr Thr Ser Thr Arg Thr Trp Ala Leu Pro Thr Tyr Asn Asn His
                            245                 250                 255
        Leu Tyr Lys Gln Ile Ser Ser Glu Thr Ala Gly Ser Thr Asn Asp Asn
                            260                 265                 270
        Thr Tyr Phe Gly Tyr Ser Thr Pro Trp Gly Tyr Phe Asp Phe Asn Arg
                            275                 280                 285
        Phe His Cys His Phe Ser Pro Arg Asp Trp Gln Arg Leu Ile Asn Asn
                            290                 295                 300
        Asn Trp Gly Phe Arg Pro Lys Lys Leu Arg Phe Lys Leu Phe Asn Ile
        305                 310                 315                 320
        Gln Val Lys Glu Val Thr Thr Asn Asp Gly Val Thr Ile Ala Asn
                            325                 330                 335
        Asn Leu Thr Ser Thr Ile Gln Val Phe Ser Asp Ser Glu Tyr Gln Leu
                            340                 345                 350
        Pro Tyr Val Leu Gly Ser Ala His Gln Gly Cys Leu Pro Pro Phe Pro
                            355                 360                 365
        Ala Asp Val Phe Met Ile Pro Gln Tyr Gly Tyr Leu Thr Leu Asn Asn
                            370                 375                 380
        Gly Ser Gln Ser Val Gly Arg Ser Ser Phe Tyr Cys Leu Glu Tyr Phe
        385                 390                 395                 400
        Pro Ser Gln Met Leu Arg Thr Gly Asn Asn Phe Glu Phe Ser Tyr Ser
                            405                 410                 415
        Phe Glu Asp Val Pro Phe His Ser Ser Tyr Ala His Ser Gln Ser Leu
                            420                 425                 430
        Asp Arg Leu Met Asn Pro Leu Ile Asp Gln Tyr Leu Tyr Tyr Leu Ala
                            435                 440                 445
        Arg Thr Gln Ser Asn Pro Gly Gly Thr Ala Gly Asn Arg Glu Leu Gln
                            450                 455                 460
        Phe Tyr Gln Gly Gly Pro Ser Thr Met Ala Glu Gln Ala Lys Asn Trp
        465                 470                 475                 480
        Leu Pro Gly Pro Cys Phe Arg Gln Gln Arg Val Ser Lys Thr Leu Asp
                            485                 490                 495
        Gln Asn Asn Asn Ser Asn Phe Ala Trp Thr Gly Ala Thr Lys Tyr His
                            500                 505                 510
        Leu Asn Gly Arg Asn Ser Leu Val Asn Pro Gly Val Ala Met Ala Thr
                            515                 520                 525
        His Lys Asp Asp Glu Asp Arg Phe Phe Pro Ser Ser Gly Val Leu Ile
                            530                 535                 540
        Phe Gly Lys Thr Gly Ala Thr Asn Lys Thr Thr Leu Glu Asn Val Leu
        545                 550                 555                 560
        Met Thr Asn Glu Glu Ile Arg Pro Thr Asn Pro Val Ala Thr Glu
                            565                 570                 575
        Glu Tyr Gly Ile Val Ser Ser Asn Leu Gln Ala Ala Asn Thr Ala Ala
                            580                 585                 590
        Gln Thr Gln Val Val Asn Asn Gln Gly Ala Leu Pro Gly Met Val Trp
                            595                 600                 605
        Gln Asn Arg Asp Val Tyr Leu Gln Gly Pro Ile Trp Ala Lys Ile Pro
                            610                 615                 620
        His Thr Asp Gly Asn Phe His Pro Ser Pro Leu Met Gly Gly Phe Gly
        625                 630                 635                 640
        Leu Lys His Pro Pro Pro Gln Ile Leu Ile Lys Asn Thr Pro Val Pro
                            645                 650                 655
```

```
Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 186
<211> LENGTH: 738
<212> TYPE: PRT
<213> ORGANISM: adeno-associated virus 8

<400> SEQUENCE: 186

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285
```

-continued

```
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
        370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
            435                 440                 445
Ser Arg Thr Gln Thr Thr Gly Gly Thr Ala Asn Thr Gln Thr Leu Gly
    450                 455                 460
Phe Ser Gln Gly Gly Pro Asn Thr Met Ala Asn Gln Ala Lys Asn Trp
465                 470                 475                 480
Leu Pro Gly Pro Cys Tyr Arg Gln Gln Arg Val Ser Thr Thr Thr Gly
                485                 490                 495
Gln Asn Asn Asn Ser Asn Phe Ala Trp Thr Ala Gly Thr Lys Tyr His
                500                 505                 510
Leu Asn Gly Arg Asn Ser Leu Ala Asn Pro Gly Ile Ala Met Ala Thr
            515                 520                 525
His Lys Asp Asp Glu Glu Arg Phe Phe Pro Ser Asn Gly Ile Leu Ile
    530                 535                 540
Phe Gly Lys Gln Asn Ala Ala Arg Asp Asn Ala Asp Tyr Ser Asp Val
545                 550                 555                 560
Met Leu Thr Ser Glu Glu Glu Ile Lys Thr Thr Asn Pro Val Ala Thr
                565                 570                 575
Glu Glu Tyr Gly Ile Val Ala Asp Asn Leu Gln Gln Gln Asn Thr Ala
            580                 585                 590
Pro Gln Ile Gly Thr Val Asn Ser Gln Gly Ala Leu Pro Gly Met Val
        595                 600                 605
Trp Gln Asn Arg Asp Val Tyr Leu Gln Gly Pro Ile Trp Ala Lys Ile
    610                 615                 620
Pro His Thr Asp Gly Asn Phe His Pro Ser Pro Leu Met Gly Gly Phe
625                 630                 635                 640
Gly Leu Lys His Pro Pro Pro Gln Ile Leu Ile Lys Asn Thr Pro Val
                645                 650                 655
Pro Ala Asp Pro Pro Thr Thr Phe Asn Gln Ser Lys Leu Asn Ser Phe
                660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
    690                 695                 700
```

```
Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 187
<211> LENGTH: 738
<212> TYPE: PRT
<213> ORGANISM: adeno-associated virus 10

<400> SEQUENCE: 187

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Ala Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Glu Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335
```

-continued

```
Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 188
```

```
<211> LENGTH: 734
<212> TYPE: PRT
<213> ORGANISM: adeno-associated virus 4

<400> SEQUENCE: 188

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
 50                  55                  60

Asn Ala Asp Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
370                 375                 380

Ala Phe Tyr Cys Leu Glu Tyr Phe Pro Ser Gln Met Leu Arg Thr Gly
```

```
            385                 390                 395                 400
Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
                435                 440                 445

Asn Ala Gly Thr Ala Thr Thr Asn Phe Thr Lys Leu Arg Pro Thr Asn
            450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
            610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
        690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
            725                 730

<210> SEQ ID NO 189
<211> LENGTH: 733
<212> TYPE: PRT
<213> ORGANISM: adeno-associated virus 11

<400> SEQUENCE: 189

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30
```

-continued

```
Lys Ala Asn Gln Gln Lys Gln Asp Gly Arg Gly Leu Val Leu Pro
         35                  40                  45
Gly Tyr Lys Tyr Leu Gly Pro Phe Asn Gly Leu Asp Lys Gly Glu Pro
 50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
            130                 135                 140
Pro Leu Glu Ser Pro Gln Glu Pro Asp Ser Ser Ser Gly Ile Gly Lys
145                 150                 155                 160
Lys Gly Lys Gln Pro Ala Arg Lys Arg Leu Asn Phe Glu Glu Asp Thr
                165                 170                 175
Gly Ala Gly Asp Gly Pro Pro Glu Gly Ser Asp Thr Ser Ala Met Ser
            180                 185                 190
Ser Asp Ile Glu Met Arg Ala Ala Pro Gly Gly Asn Ala Val Asp Ala
            195                 200                 205
Gly Gln Gly Ser Asp Gly Val Gly Asn Ala Ser Gly Asp Trp His Cys
            210                 215                 220
Asp Ser Thr Trp Ser Glu Gly Lys Val Thr Thr Thr Ser Thr Arg Thr
225                 230                 235                 240
Trp Val Leu Pro Thr Tyr Asn Asn His Leu Tyr Leu Arg Leu Gly Thr
                245                 250                 255
Thr Ser Ser Ser Asn Thr Tyr Asn Gly Phe Ser Thr Pro Trp Gly Tyr
            260                 265                 270
Phe Asp Phe Asn Arg Phe His Cys His Phe Ser Pro Arg Asp Trp Gln
            275                 280                 285
Arg Leu Ile Asn Asn Asn Trp Gly Leu Arg Pro Lys Ala Met Arg Val
            290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
            340                 345                 350
Leu Pro Pro Phe Pro Asn Asp Val Phe Met Val Pro Gln Tyr Gly Tyr
            355                 360                 365
Cys Gly Ile Val Thr Gly Glu Asn Gln Asn Gln Thr Asp Arg Asn Ala
            370                 375                 380
Phe Tyr Cys Leu Glu Tyr Phe Pro Ser Gln Met Leu Arg Thr Gly Asn
385                 390                 395                 400
Asn Phe Glu Met Ala Tyr Asn Phe Glu Lys Val Pro Phe His Ser Met
                405                 410                 415
Tyr Ala His Ser Gln Ser Leu Asp Arg Leu Met Asn Pro Leu Leu Asp
            420                 425                 430
Gln Tyr Leu Trp His Leu Gln Ser Thr Thr Ser Gly Glu Thr Leu Asn
            435                 440                 445
Gln Gly Asn Ala Ala Thr Thr Phe Gly Lys Ile Arg Ser Gly Asp Phe
```

```
            450                 455                 460
Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
                500                 505                 510

Trp Ser Asn Ile Ala Pro Gly Pro Met Ala Thr Ala Gly Pro Ser
            515                 520                 525

Asp Gly Asp Phe Ser Asn Ala Gln Leu Ile Phe Pro Gly Pro Ser Val
            530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
                580                 585                 590

Val Thr Ala Met Gly Val Leu Pro Gly Met Val Trp Gln Asn Arg Asp
                595                 600                 605

Ile Tyr Tyr Gln Gly Pro Ile Trp Ala Lys Ile Pro His Ala Asp Gly
                610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
                675                 680                 685

Ser Lys Arg Trp Asn Pro Glu Val Gln Phe Thr Ser Asn Tyr Gly Asn
                690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 190
<211> LENGTH: 736
<212> TYPE: PRT
<213> ORGANISM: bovine adeno-associated virus

<400> SEQUENCE: 190

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
                20                  25                  30

Ala Asn Gln Gln Lys Gln Asp Asn Ala Arg Gly Leu Val Leu Pro Gly
            35                  40                  45

Tyr Lys Tyr Leu Gly Pro Gly Asn Gly Leu Asp Lys Gly Asp Pro Val
        50                  55                  60

Asn Phe Ala Asp Glu Val Ala Arg Glu His Asp Leu Ser Tyr Gln Lys
65                  70                  75                  80

Gln Leu Glu Ala Gly Asp Asn Pro Tyr Leu Lys Tyr Asn His Ala Asp
                85                  90                  95
```

-continued

```
Ala Glu Phe Gln Glu Lys Leu Ala Ser Asp Thr Ser Phe Gly Gly Asn
            100                 105                 110
Leu Gly Lys Ala Val Phe Gln Ala Lys Lys Arg Ile Leu Glu Pro Leu
        115                 120                 125
Gly Leu Val Glu Thr Pro Asp Lys Thr Ala Pro Ala Lys Lys Arg
    130                 135                 140
Pro Leu Glu Gln Ser Pro Gln Glu Pro Asp Ser Ser Ser Gly Val Gly
145                 150                 155                 160
Lys Lys Gly Lys Gln Pro Ala Arg Lys Arg Leu Asn Phe Asp Asp Glu
                165                 170                 175
Pro Gly Ala Gly Asp Gly Pro Pro Glu Gly Pro Ser Ser Gly Ala
            180                 185                 190
Met Ser Thr Glu Thr Glu Met Arg Ala Ala Gly Gly Asn Gly Gly
            195                 200                 205
Asp Ala Gly Gln Gly Ala Glu Gly Val Gly Asn Ala Ser Gly Asp Trp
    210                 215                 220
His Cys Asp Ser Thr Trp Ser Glu Ser His Val Thr Thr Ser Thr
225                 230                 235                 240
Arg Thr Trp Val Leu Pro Thr Tyr Asn Asn His Leu Tyr Leu Arg Leu
                245                 250                 255
Gly Ser Ser Asn Ala Ser Asp Thr Phe Asn Gly Phe Ser Thr Pro Trp
            260                 265                 270
Gly Tyr Phe Asp Phe Asn Arg Phe His Cys His Phe Ser Pro Arg Asp
        275                 280                 285
Trp Gln Arg Leu Ile Asn Asn His Trp Gly Leu Arg Pro Lys Ser Met
    290                 295                 300
Gln Val Arg Ile Phe Asn Ile Gln Val Lys Glu Val Thr Thr Ser Asn
305                 310                 315                 320
Gly Glu Thr Thr Val Ser Asn Asn Leu Thr Ser Thr Val Gln Ile Phe
                325                 330                 335
Ala Asp Ser Thr Tyr Glu Leu Pro Tyr Val Met Asp Ala Gly Gln Glu
            340                 345                 350
Gly Ser Leu Pro Pro Phe Pro Asn Asp Val Phe Met Val Pro Gln Tyr
        355                 360                 365
Gly Tyr Cys Gly Leu Val Thr Gly Ser Ser Gln Asn Gln Thr Asp
    370                 375                 380
Arg Asn Ala Phe Tyr Cys Leu Glu Tyr Phe Pro Ser Gln Met Leu Arg
385                 390                 395                 400
Thr Gly Asn Asn Phe Glu Met Val Tyr Lys Phe Glu Asn Val Pro Phe
                405                 410                 415
His Ser Met Tyr Ala His Ser Gln Ser Leu Asp Arg Leu Met Asn Pro
            420                 425                 430
Leu Leu Asp Gln Tyr Leu Trp Glu Leu Gln Ser Thr Thr Ser Gly Gly
        435                 440                 445
Thr Leu Asn Gln Gly Asn Ser Ala Thr Asn Phe Ala Lys Leu Thr Lys
    450                 455                 460
Thr Asn Phe Ser Gly Tyr Arg Lys Asn Trp Leu Pro Gly Pro Met Met
465                 470                 475                 480
Lys Gln Gln Arg Phe Ser Lys Thr Ala Ser Gln Asn Tyr Lys Ile Pro
                485                 490                 495
Gln Gly Arg Asn Asn Ser Leu Leu His Tyr Glu Thr Arg Thr Thr Leu
            500                 505                 510
Asp Gly Arg Trp Ser Asn Phe Ala Pro Gly Thr Ala Met Ala Thr Ala
```

```
                515                 520                 525
Ala Asn Asp Ala Thr Asp Phe Ser Gln Ala Gln Leu Ile Phe Ala Gly
        530                 535                 540

Pro Asn Ile Thr Gly Asn Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575

Phe Gly His Leu Ala Thr Asn Gln Gln Asn Ala Thr Thr Val Pro Thr
            580                 585                 590

Val Asp Asp Val Asp Gly Val Gly Val Tyr Pro Gly Met Val Trp Gln
            595                 600                 605

Asp Arg Asp Ile Tyr Tyr Gln Gly Pro Ile Trp Ala Lys Ile Pro His
            610                 615                 620

Thr Asp Gly His Phe His Pro Ser Pro Leu Ile Gly Gly Phe Gly Leu
625                 630                 635                 640

Lys Ser Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
            660                 665                 670

Gln Tyr Ser Thr Gly Gln Val Ala Val Lys Ile Glu Trp Glu Ile Gln
            675                 680                 685

Lys Glu Arg Ser Lys Arg Trp Asn Pro Glu Val Gln Phe Thr Ser Asn
690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735

<210> SEQ ID NO 191
<211> LENGTH: 724
<212> TYPE: PRT
<213> ORGANISM: adeno-associated virus 5

<400> SEQUENCE: 191

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160
```

-continued

```
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Pro Leu Gly Asp Asn Asn Gln Gly Ala
        195                 200                 205
Asp Gly Val Gly Asn Ala Ser Gly Asp Trp His Cys Asp Ser Thr Trp
    210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
        275                 280                 285
Arg Leu Ile Asn Asn Tyr Trp Gly Phe Arg Pro Arg Ser Leu Arg Val
    290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
        355                 360                 365
Ala Thr Leu Asn Arg Asp Asn Thr Glu Asn Pro Thr Glu Arg Ser Ser
    370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
        435                 440                 445
Phe Asn Lys Asn Leu Ala Gly Arg Tyr Ala Asn Thr Tyr Lys Asn Trp
    450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
            500                 505                 510
Asn Asn Leu Gln Gly Ser Asn Thr Tyr Ala Leu Glu Asn Thr Met Ile
        515                 520                 525
Phe Asn Ser Gln Pro Ala Asn Pro Gly Thr Thr Ala Thr Tyr Leu Glu
    530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
```

```
              580                 585                 590
Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
            610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                    645                 650                 655

Ser Phe Ile Thr Gln Tyr Ser Thr Gly Gln Val Thr Val Glu Met Glu
                        660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 192
<211> LENGTH: 534
<212> TYPE: PRT
<213> ORGANISM: goose parvovirus

<400> SEQUENCE: 192

Met Ala Glu Gly Gly Gly Gly Ala Met Gly Asp Ser Ser Gly Gly Ala
1               5                   10                  15

Asp Gly Val Gly Asn Ala Ser Gly Asn Trp His Cys Asp Ser Gln Trp
                20                  25                  30

Met Gly Asn Thr Val Ile Thr Lys Thr Thr Arg Thr Trp Val Leu Pro
            35                  40                  45

Ser Tyr Asn Asn His Ile Tyr Lys Ala Ile Thr Ser Gly Thr Ser Gln
    50                  55                  60

Asp Ala Asn Val Gln Tyr Ala Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn His Trp Gly Ile Arg Pro Lys Ser Leu Lys Phe Lys
            100                 105                 110

Ile Phe Asn Val Gln Val Lys Glu Val Thr Thr Gln Asp Gln Thr Lys
        115                 120                 125

Thr Ile Ala Asn Asn Leu Thr Ser Thr Ile Gln Val Phe Thr Asp Asp
    130                 135                 140

Glu His Gln Leu Pro Tyr Val Leu Gly Ser Ala Thr Glu Gly Thr Met
145                 150                 155                 160

Pro Pro Phe Pro Ser Asp Val Tyr Ala Leu Pro Gln Tyr Gly Tyr Cys
                165                 170                 175

Thr Met His Thr Asn Gln Asn Gly Ala Arg Phe Asn Asp Arg Ser Ala
            180                 185                 190

Phe Tyr Cys Leu Glu Tyr Phe Pro Ser Gln Met Leu Arg Thr Gly Asn
        195                 200                 205

Asn Phe Glu Phe Thr Phe Asp Phe Glu Glu Val Pro Phe His Ser Met
    210                 215                 220

Phe Ala His Ser Gln Asp Leu Asp Arg Leu Met Asn Pro Leu Val Asp
```

|   |   |   |   |   |   |   |   |   |   |   |   |   |   |   |
|---|---|---|---|---|---|---|---|---|---|---|---|---|---|---|
| 225 | | | | | 230 | | | | | 235 | | | | 240 |

Gln Tyr Leu Trp Asn Phe Asn Glu Val Asp Ser Ser Arg Asn Ala Gln
                        245                      250                      255

Phe Lys Lys Ala Val Lys Gly Ala Tyr Gly Thr Met Gly Arg Asn Trp
                      260                      265                      270

Leu Pro Gly Pro Lys Phe Leu Asp Gln Arg Val Arg Ala Tyr Thr Gly
                      275                      280                      285

Gly Thr Asp Asn Tyr Ala Asn Trp Asn Ile Trp Ser Asn Gly Asn Lys
                      290                      295                      300

Val Asn Leu Lys Asp Arg Gln Tyr Leu Leu Gln Pro Gly Pro Val Ser
305                      310                      315                      320

Ala Thr Tyr Thr Glu Gly Ala Ser Ser Leu Pro Ala Gln Asn Ile
                      325                      330                      335

Leu Gly Ile Ala Lys Asp Pro Tyr Arg Ser Gly Ser Thr Thr Ala Gly
                      340                      345                      350

Ile Ser Asp Ile Met Val Thr Glu Glu Gln Glu Val Ala Pro Thr Asn
                      355                      360                      365

Gly Val Gly Trp Lys Pro Tyr Gly Arg Thr Val Thr Asn Glu Gln Asn
                      370                      375                      380

Thr Thr Thr Ala Pro Thr Ser Ser Asp Leu Asp Val Leu Gly Ala Leu
385                      390                      395                      400

Pro Gly Met Val Trp Gln Asn Arg Asp Ile Tyr Leu Gln Gly Pro Ile
                      405                      410                      415

Gly Ala Lys Ile Pro Lys Thr Asp Gly Lys Phe His Pro Ser Pro Asn
                      420                      425                      430

Leu Gly Gly Phe Gly Leu His Asn Pro Pro Pro Gln Val Phe Ile Lys
                      435                      440                      445

Asn Thr Pro Val Pro Ala Asp Pro Pro Val Glu Tyr Val His Gln Lys
                      450                      455                      460

Trp Asn Ser Tyr Ile Thr Gln Tyr Ser Thr Gly Gln Cys Thr Val Glu
465                      470                      475                      480

Met Val Trp Glu Leu Arg Lys Glu Asn Ser Lys Arg Trp Asn Pro Glu
                      485                      490                      495

Ile Gln Phe Thr Ser Asn Phe Ser Asn Arg Thr Ser Ile Met Phe Ala
                      500                      505                      510

Pro Asn Glu Thr Gly Gly Tyr Val Glu Asp Arg Leu Ile Gly Thr Arg
                      515                      520                      525

Tyr Leu Thr Gln Asn Leu
                      530

<210> SEQ ID NO 193
<211> LENGTH: 554
<212> TYPE: PRT
<213> ORGANISM: parvovirus B19

<400> SEQUENCE: 193

Met Thr Ser Val Asn Ser Ala Glu Ala Ser Thr Gly Ala Gly Gly Gly
1                  5                      10                      15

Gly Ser Asn Pro Val Lys Ser Met Trp Ser Glu Gly Ala Thr Phe Ser
                      20                      25                      30

Ala Asn Ser Val Thr Cys Thr Phe Ser Arg Gln Phe Leu Ile Pro Tyr
                      35                      40                      45

Asp Pro Glu His His Tyr Lys Val Phe Ser Pro Ala Ala Ser Ser Cys
                      50                      55                      60

His Asn Ala Ser Gly Lys Glu Ala Lys Val Cys Thr Ile Ser Pro Ile
 65                  70                  75                  80

Met Gly Tyr Ser Thr Pro Trp Arg Tyr Leu Asp Phe Asn Ala Leu Asn
                 85                  90                  95

Leu Phe Phe Ser Pro Leu Glu Phe Gln His Leu Ile Glu Asn Tyr Gly
            100                 105                 110

Ser Ile Ala Pro Asp Ala Leu Thr Val Thr Ile Ser Glu Ile Ala Val
        115                 120                 125

Lys Asp Val Thr Asp Lys Thr Gly Gly Val Gln Val Thr Asp Ser
130                 135                 140

Thr Thr Gly Arg Leu Cys Met Leu Val Asp His Glu Tyr Lys Tyr Pro
145                 150                 155                 160

Tyr Val Leu Gly Gln Gly Gln Asp Thr Leu Ala Pro Glu Leu Pro Ile
                165                 170                 175

Trp Val Tyr Phe Pro Pro Gln Tyr Ala Tyr Leu Thr Val Gly Asp Val
            180                 185                 190

Asn Thr Gln Gly Ile Ser Gly Asp Ser Lys Lys Leu Ala Ser Glu Glu
        195                 200                 205

Ser Ala Phe Tyr Val Leu Glu His Ser Ser Phe Gln Leu Leu Gly Thr
210                 215                 220

Gly Gly Thr Ala Thr Met Ser Tyr Lys Phe Pro Pro Val Pro Pro Glu
225                 230                 235                 240

Asn Leu Glu Gly Cys Ser Gln His Phe Tyr Glu Met Tyr Asn Pro Leu
                245                 250                 255

Tyr Gly Ser Arg Leu Gly Val Pro Asp Thr Leu Gly Gly Asp Pro Lys
            260                 265                 270

Phe Arg Ser Leu Thr His Glu Asp His Ala Ile Gln Pro Gln Asn Phe
        275                 280                 285

Met Pro Gly Pro Leu Val Asn Ser Val Ser Thr Lys Glu Gly Asp Ser
290                 295                 300

Phe Asn Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
            340                 345                 350

Ser His Gly Gln Thr Thr Tyr Gly Asn Ala Glu Asp Lys Glu Tyr Gln
        355                 360                 365

Gln Gly Val Gly Arg Phe Pro Asn Glu Lys Glu Gln Leu Lys Gln Leu
370                 375                 380

Gln Gly Leu Asn Met His Thr Tyr Phe Pro Asn Lys Gly Thr Gln Gln
385                 390                 395                 400

Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
            420                 425                 430

Leu Asp Asp Ser Phe Lys Thr Gln Phe Ala Ala Leu Gly Gly Trp Gly
        435                 440                 445

Leu His Gln Pro Pro Pro Gln Ile Phe Leu Lys Ile Leu Pro Gln Ser
450                 455                 460

Gly Pro Ile Gly Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro

```
                        485                 490                 495
Arg Lys Ala Thr Gly Arg Trp Asn Pro Gln Pro Gly Val Tyr Pro Pro
            500                 505                 510

His Ala Ala Gly His Leu Pro Tyr Val Leu Tyr Asp Pro Thr Ala Thr
            515                 520                 525

Asp Ala Lys Gln His His Arg His Gly Tyr Glu Lys Pro Glu Glu Leu
            530                 535                 540

Trp Thr Ala Lys Ser Arg Val His Pro Leu
545                 550

<210> SEQ ID NO 194
<211> LENGTH: 587
<212> TYPE: PRT
<213> ORGANISM: minute virus of mice

<400> SEQUENCE: 194

Met Ser Asp Gly Thr Ser Gln Pro Asp Gly Gly Asn Ala Val His Ser
1               5                   10                  15

Ala Ala Arg Val Glu Arg Ala Ala Asp Gly Pro Gly Gly Ser Gly Gly
            20                  25                  30

Gly Gly Ser Gly Gly Gly Val Gly Val Ser Thr Gly Ser Tyr Asp
            35                  40                  45

Asn Gln Thr His Tyr Arg Phe Leu Gly Asp Gly Trp Val Glu Ile Thr
50                  55                  60

Ala Leu Ala Thr Arg Leu Val His Leu Asn Met Pro Lys Ser Glu Asn
65                  70                  75                  80

Tyr Cys Arg Ile Arg Val His Asn Thr Thr Asp Thr Ser Val Lys Gly
            85                  90                  95

Asn Met Ala Lys Asp Asp Ala His Glu Gln Ile Trp Thr Pro Trp Ser
            100                 105                 110

Leu Val Asp Ala Asn Ala Trp Gly Val Trp Leu Gln Pro Ser Asp Trp
            115                 120                 125

Gln Tyr Ile Cys Asn Thr Met Ser Gln Leu Asn Leu Val Ser Leu Asp
            130                 135                 140

Gln Glu Ile Phe Asn Val Val Leu Lys Thr Val Thr Glu Gln Asp Ser
145                 150                 155                 160

Gly Gly Gln Ala Ile Lys Ile Tyr Asn Asn Asp Leu Thr Ala Cys Met
            165                 170                 175

Met Val Ala Val Asp Ser Asn Asn Ile Leu Pro Tyr Thr Pro Ala Ala
            180                 185                 190

Asn Ser Met Glu Thr Leu Gly Phe Tyr Pro Trp Lys Pro Thr Ile Ala
            195                 200                 205

Ser Pro Tyr Arg Tyr Tyr Phe Cys Val Asp Arg Asp Leu Ser Val Thr
            210                 215                 220

Tyr Glu Asn Gln Glu Gly Thr Ile Glu His Asn Val Met Gly Thr Pro
225                 230                 235                 240

Lys Gly Met Asn Ser Gln Phe Phe Thr Ile Glu Asn Thr Gln Gln Ile
            245                 250                 255

Thr Leu Leu Arg Thr Gly Asp Glu Phe Ala Thr Gly Thr Tyr Tyr Phe
            260                 265                 270

Asp Thr Asn Pro Val Lys Leu Thr His Thr Trp Gln Thr Asn Arg Gln
            275                 280                 285

Leu Gly Gln Pro Pro Leu Leu Ser Thr Phe Pro Glu Ala Asp Thr Asp
            290                 295                 300
```

```
Ala Gly Thr Leu Thr Ala Gln Gly Ser Arg His Gly Ala Thr Gln Met
305                 310                 315                 320

Glu Val Asn Trp Val Ser Glu Ala Ile Arg Thr Arg Pro Ala Gln Val
            325                 330                 335

Gly Phe Cys Gln Pro His Asn Asp Phe Glu Ala Ser Arg Ala Gly Pro
        340                 345                 350

Phe Ala Ala Pro Lys Val Pro Ala Asp Val Thr Gln Gly Met Asp Arg
            355                 360                 365

Glu Ala Asn Gly Ser Val Arg Tyr Ser Tyr Gly Lys Gln His Gly Glu
        370                 375                 380

Asn Trp Ala Ala His Gly Pro Ala Pro Glu Arg Tyr Thr Trp Asp Glu
385                 390                 395                 400

Thr Asn Phe Gly Ser Gly Arg Asp Thr Arg Asp Gly Phe Ile Gln Ser
            405                 410                 415

Ala Pro Leu Val Val Pro Pro Leu Asn Gly Ile Leu Thr Asn Ala
        420                 425                 430

Asn Pro Ile Gly Thr Lys Asn Asp Ile His Phe Ser Asn Val Phe Asn
            435                 440                 445

Ser Tyr Gly Pro Leu Thr Thr Phe Ser His Pro Ser Pro Val Tyr Pro
        450                 455                 460

Gln Gly Gln Ile Trp Asp Lys Glu Leu Asp Leu Glu His Lys Pro Arg
465                 470                 475                 480

Leu His Ile Thr Ala Pro Phe Val Cys Lys Asn Asn Ala Pro Gly Gln
            485                 490                 495

Met Leu Val Arg Leu Gly Pro Asn Leu Thr Asp Gln Tyr Asp Pro Asn
            500                 505                 510

Gly Ala Thr Leu Ser Arg Ile Val Thr Tyr Gly Thr Phe Phe Trp Lys
        515                 520                 525

Gly Lys Leu Thr Met Arg Ala Lys Leu Arg Ala Asn Thr Thr Trp Asn
        530                 535                 540

Pro Val Tyr Gln Val Ser Val Glu Asp Asn Gly Asn Ser Tyr Met Ser
545                 550                 555                 560

Val Thr Lys Trp Leu Pro Thr Ala Thr Gly Asn Met Gln Ser Val Pro
            565                 570                 575

Leu Ile Thr Arg Pro Val Ala Arg Asn Thr Tyr
            580                 585

<210> SEQ ID NO 195
<211> LENGTH: 584
<212> TYPE: PRT
<213> ORGANISM: feline panleukopenia virus

<400> SEQUENCE: 195

Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Lys
65                  70                  75                  80

Arg Val Val Val Asn Asn Met Asp Lys Thr Ala Val Lys Gly Asn Met
                85                  90                  95
```

```
Ala Leu Asp Asp Ile His Val Glu Ile Val Thr Pro Trp Ser Leu Val
            100                 105                 110

Asp Ala Asn Ala Trp Gly Val Trp Phe Asn Pro Gly Asp Trp Gln Leu
            115                 120                 125

Ile Val Asn Thr Met Ser Glu Leu His Leu Val Ser Phe Glu Gln Glu
            130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
            195                 200                 205

Arg Tyr Tyr Phe Gln Trp Asp Arg Thr Leu Ile Pro Ser His Thr Gly
            210                 215                 220

Thr Ser Gly Thr Pro Thr Asn Val Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Asp Cys Lys Pro
            260                 265                 270

Cys Arg Leu Thr His Thr Trp Gln Thr Asn Arg Ala Leu Gly Leu Pro
            275                 280                 285

Pro Phe Leu Asn Ser Leu Pro Gln Ser Glu Gly Ala Thr Asn Phe Gly
            290                 295                 300

Asp Ile Gly Val Gln Gln Asp Lys Arg Arg Gly Val Thr Gln Met Gly
305                 310                 315                 320

Asn Thr Asp Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
            355                 360                 365

Asn Gln Ala Ala Asp Gly Asp Pro Arg Tyr Ala Phe Gly Arg Gln His
            370                 375                 380

Gly Gln Lys Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Thr Asn Asp Asn Val Leu Leu Pro
            420                 425                 430

Thr Asp Pro Ile Gly Gly Lys Thr Gly Ile Asn Tyr Thr Asn Ile Phe
            435                 440                 445

Asn Thr Tyr Gly Pro Leu Thr Ala Leu Asn Asn Val Pro Pro Val Tyr
            450                 455                 460

Pro Asn Gly Gln Ile Trp Asp Lys Glu Phe Asp Thr Asp Leu Lys Pro
465                 470                 475                 480

Arg Leu His Ile Asn Ala Pro Phe Val Cys Gln Asn Cys Pro Gly
                485                 490                 495

Gln Leu Phe Val Lys Val Ala Pro Asn Leu Thr Asn Gln Tyr Asp Pro
            500                 505                 510
```

```
Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Asn Asn Ile Gly Ala Met Lys Ile Val Tyr Glu Lys Ser
                565                 570                 575

Gln Leu Ala Pro Arg Lys Leu Tyr
            580

<210> SEQ ID NO 196
<211> LENGTH: 548
<212> TYPE: PRT
<213> ORGANISM: canine parvovirus

<400> SEQUENCE: 196

Gly Val Gly Ile Ser Thr Gly Thr Phe Asn Asn Gln Thr Glu Phe Lys
1               5                   10                  15

Phe Leu Glu Asn Gly Trp Val Glu Ile Thr Ala Asn Ser Ser Arg Leu
            20                  25                  30

Val His Leu Asn Met Pro Glu Ser Glu Asn Tyr Arg Arg Val Val Val
        35                  40                  45

Asn Asn Met Asp Lys Thr Ala Val Asn Gly Asn Met Ala Leu Asp Asp
    50                  55                  60

Ile His Ala Gln Ile Val Thr Pro Trp Ser Leu Val Asp Ala Asn Ala
65                  70                  75                  80

Trp Gly Val Trp Phe Asn Pro Gly Asp Trp Gln Leu Ile Val Asn Thr
                85                  90                  95

Met Ser Glu Leu His Leu Val Ser Phe Glu Gln Glu Ile Phe Asn Val
            100                 105                 110

Val Leu Lys Thr Val Ser Glu Ser Ala Thr Gln Pro Pro Thr Lys Val
        115                 120                 125

Tyr Asn Asn Asp Leu Thr Ala Ser Leu Met Val Ala Leu Asp Ser Asn
    130                 135                 140

Asn Thr Met Pro Phe Thr Pro Ala Ala Met Arg Ser Glu Thr Leu Gly
145                 150                 155                 160

Phe Tyr Pro Trp Lys Pro Thr Ile Pro Thr Pro Trp Arg Tyr Tyr Phe
                165                 170                 175

Gln Trp Asp Arg Thr Leu Ile Pro Ser His Thr Gly Thr Ser Gly Thr
            180                 185                 190

Pro Thr Asn Ile Tyr His Gly Thr Asp Pro Asp Asp Val Gln Phe Tyr
        195                 200                 205

Thr Ile Glu Asn Ser Val Pro Val His Leu Leu Arg Thr Gly Asp Glu
    210                 215                 220

Phe Ala Thr Gly Thr Phe Phe Phe Asp Cys Lys Pro Cys Arg Leu Thr
225                 230                 235                 240

His Thr Trp Gln Thr Asn Arg Ala Leu Gly Leu Pro Pro Phe Leu Asn
                245                 250                 255

Ser Leu Pro Gln Ser Glu Gly Ala Thr Asn Phe Gly Asp Ile Gly Val
            260                 265                 270

Gln Gln Asp Lys Arg Arg Gly Val Thr Gln Met Gly Asn Thr Asn Tyr
        275                 280                 285

Ile Thr Glu Ala Thr Ile Met Arg Pro Ala Glu Val Gly Tyr Ser Ala
    290                 295                 300

Pro Tyr Tyr Ser Phe Glu Ala Ser Thr Gln Gly Pro Phe Lys Thr Pro
305                 310                 315                 320

Ile Ala Ala Gly Arg Gly Gly Ala Gln Thr Asp Glu Asn Gln Ala Ala
            325                 330                 335

Asp Gly Asn Pro Arg Tyr Ala Phe Gly Arg Gln His Gly Gln Lys Thr
            340                 345                 350

Thr Thr Thr Gly Glu Thr Pro Glu Arg Phe Thr Tyr Ile Ala His Gln
        355                 360                 365

Asp Thr Gly Arg Tyr Pro Glu Gly Asp Trp Ile Gln Asn Ile Asn Phe
    370                 375                 380

Asn Leu Pro Val Thr Asn Asp Asn Val Leu Leu Pro Thr Asp Pro Ile
385                 390                 395                 400

Gly Gly Lys Thr Gly Ile Asn Tyr Thr Asn Ile Phe Asn Thr Tyr Gly
            405                 410                 415

Pro Leu Thr Ala Leu Asn Asn Val Pro Pro Val Tyr Pro Asn Gly Gln
            420                 425                 430

Ile Trp Asp Lys Glu Phe Asp Thr Asp Leu Lys Pro Arg Leu His Val
        435                 440                 445

Asn Ala Pro Phe Val Cys Gln Asn Asn Cys Pro Gly Gln Leu Phe Val
    450                 455                 460

Lys Val Ala Pro Asn Leu Thr Asn Glu Tyr Asp Pro Asp Ala Ser Ala
465                 470                 475                 480

Asn Met Ser Arg Ile Val Thr Tyr Ser Asp Phe Trp Trp Lys Gly Lys
            485                 490                 495

Leu Val Phe Lys Ala Lys Leu Arg Ala Ser His Thr Trp Asn Pro Ile
            500                 505                 510

Gln Gln Met Ser Ile Asn Val Asp Asn Gln Phe Asn Tyr Val Pro Ser
        515                 520                 525

Asn Ile Gly Gly Met Lys Ile Val Tyr Glu Lys Ser Gln Leu Ala Pro
    530                 535                 540

Arg Lys Leu Tyr
545

The invention claimed is:

1. A structural protein of a parvovirus which comprises a first amino acid insertion of one or more amino acids into I-453, and a second amino acid insertion of one or more amino acids into I-587, wherein the first amino acid insertion is directly C-terminal of amino acid $G_{453}$ and the second amino acid insertion is directly C-terminal of amino acid N587 in the sequence of AAV-2 or the corresponding amino acids of any other parvovirus, wherein the first amino acid insertion and the second amino acid insertion are each a tolerogen-derived epitope.

2. The structural protein of claim 1, wherein the insertion is located on the surface of the capsid formed by the structural proteins.

3. The structural protein of claim 1, wherein the structural protein with the insertion is capable of particle formation.

4. The structural protein of claim 1, wherein the parvovirus is an adeno-associated virus.

5. The structural protein of claim 1, wherein the parvovirus is selected from the group consisting of AAV-1, AAV-2, AAV-3b, AAV-4, AAV-5, AAV-6, AAV-7, AAV-8, AAV-9, AAV-10, AAV-11, AAV-12, b-AAV, feline panleukopenia virus (FPV), canine parvovirus (CPV), B19, goose parvovirus (GPV) and minute virus of mice (MVM).

6. The structural protein of claim 1, wherein the amino acid insertion has a length of about 4 to about 30 amino acids.

7. The structural protein of claim 1, wherein the tolerogen-derived epitope is derived from a protein from the group consisting of CETP, CD20, acetylcholine receptors, IL13R, EGFR, IgE, Melan A, HMW MAA, CA125, Her2/NEU, CCR5, L1 cell adhesion molecule, VEGF, EGFR, CD20, TNF-α, IL-6, IL9, IL-13, IL-17, and β-amyloid.

8. The structural protein of claim 7, wherein the tolerogen-derived epitope is selected from the group consisting of VNLTWSRASG (SEQ ID NO: 50), EFCINHRGYWVCGD (SEQ ID NO:55), EDGQVMDVDLS (SEQ ID NO: 85), EKQRNGTLT (SEQ ID NO: 86), TYQCRVTHPHLPRALMR (SEQ ID NO: 87), RHSTTQPRKTKGSG (SEQ ID NO: 88), DSNPRGVSAYLSR (SEQ ID NO: 89), TITCLWDLAPSK (SEQ ID NO: 90), KTKGSGFFVF (SEQ ID NO: 91), THPHLPRALMRS (SEQ ID NO: 92), GETYQCRVTHPHLPRALMRSTTK (SEQ ID NO: 93), LPRALMRS (SEQ ID NO: 94), INHRGYWV (SEQ ID NO: 95), CDAGSVRTNAPD (SEQ ID NO: 60), AKAVSNLTESRSESLQS (SEQ ID NO: 96), SLTGDEFKKVLET (SEQ ID NO: 97), REAVAYRFEED (SEQ ID NO: 98), INPEIITLDG (SEQ ID NO: 99), DISVTGAPVITATYL (SEQ ID NO: 100), DISVTGAPVITA (SEQ ID NO: 101), PKTVSNLTESSSESVQS (SEQ ID NO: 102), SLMGDEFKAVLET (SEQ ID NO: 103), QHSVAYTFEED (SEQ ID NO: 104), INPEIITRDG (SEQ ID NO: 105), DISLTGDPVITASYL (SEQ ID NO: 106), DISLTGDPVITA (SEQ ID NO: 107), DQSIDFEIDSA (SEQ ID NO: 108), KNVSEDLPLPTFSPTLLGDS (SEQ ID NO: 109), KNVSEDLPLPT (SEQ ID NO: 110), CDSGRVRTDAPD (SEQ ID NO: 111), FPEHLLVDFLQSLS (SEQ ID NO: 112), DAEFRHDSG (SEQ ID NO: 65), HYAAAQWDFGNTMCQL (SEQ ID NO: 113), YAAQWDFGNTMCQ (SEQ ID NO: 114), RSQKEGLHYT (SEQ ID NO: 115), SSRTPSDKPVAHWANPQAE (SEQ ID NO: 116), SRTPSDKPVAHWANP (SEQ ID NO: 117), SSRTPSDKP (SEQ ID NO: 118), NADGNVDYHMNSVP (SEQ ID NO: 119), DGNVDYHMNSV (SEQ ID NO: 120), RSFKEFLQSSLRALRQ (SEQ ID NO: 121); FKEFLQSSLRA (SEQ ID NO: 122), and QMWAPQWGPD (SEQ ID NO: 123).

9. The structural protein of claim 1, wherein the amino acid insertion brings about an alteration in a chromatographic property of the structural protein.

10. The structural protein of claim 5, wherein the parvovirus structural protein comprises one or more further mutation(s) at a site different to I-453 and I-587 independently selected from a point mutation, an internal deletion, an N-terminal deletion, an insertion and a substitution.

11. The structural protein of claim 10, wherein the further mutation is an insertion of a B-cell epitope or a cytotoxic T-cell epitope.

12. The structural protein of claim 10, wherein the further mutation reduces the transducing activity of the particle for a given target cell by at least 50%.

13. The structural protein of claim 10, wherein the further mutation reduces the ability to induce a B-cell response against a parvovirus-specific epitope and/or mimotope.

14. An isolated nucleic acid molecule encoding a structural protein of claim 1.

15. A vector comprising the nucleic acid molecule of claim 14.

16. A composition comprising at least one parvovirus structural protein according to claim 1 or a nucleic acid molecule according to claim 14.

* * * * *